US011077131B2

(12) United States Patent
Van Brempt

(10) Patent No.: US 11,077,131 B2
(45) Date of Patent: Aug. 3, 2021

(54) MODULATION OF CILIOGENESIS

(71) Applicant: Academisch Ziekenhuis Leiden a/u Leiden University Medical Center, Leiden (NL)

(72) Inventor: Ronald Karel Louisa Van Brempt, Leiden (NL)

(73) Assignee: Academisch Ziekenhuis Leiden a/u Leiden University Medical Center, Leiden (NL)

( * ) Notice: Subject to any disclaimer, the term of this patent is extended or adjusted under 35 U.S.C. 154(b) by 13 days.

(21) Appl. No.: 15/776,668

(22) PCT Filed: Nov. 17, 2016

(86) PCT No.: PCT/EP2016/078075
§ 371 (c)(1),
(2) Date: May 16, 2018

(87) PCT Pub. No.: WO2017/085225
PCT Pub. Date: May 26, 2017

(65) Prior Publication Data
US 2018/0325937 A1    Nov. 15, 2018

(30) Foreign Application Priority Data
Nov. 17, 2015 (GB) .................................. 1520258.3

(51) Int. Cl.
| | |
|---|---|
| *A61K 38/00* | (2006.01) |
| *A61K 39/00* | (2006.01) |
| *A61K 45/00* | (2006.01) |
| *A61K 31/7088* | (2006.01) |
| *A61K 38/17* | (2006.01) |
| *C12N 15/113* | (2010.01) |
| *A61P 9/00* | (2006.01) |
| *A61P 11/00* | (2006.01) |
| *A61K 45/06* | (2006.01) |

(52) U.S. Cl.
CPC ...... *A61K 31/7088* (2013.01); *A61K 38/1709* (2013.01); *A61K 45/00* (2013.01); *A61K 45/06* (2013.01); *A61P 9/00* (2018.01); *A61P 11/00* (2018.01); *C12N 15/113* (2013.01); *C12N 2310/14* (2013.01); *C12N 2310/531* (2013.01)

(58) Field of Classification Search
None
See application file for complete search history.

(56) References Cited

U.S. PATENT DOCUMENTS 4,376,110 A    3/1983 David et al.

FOREIGN PATENT DOCUMENTS

WO    2012127289    9/2012

OTHER PUBLICATIONS

Gascue et al., Direct role of Bardet-Biedl syndrome proteins in transcriptional regulation. 2012, Journal of Cell Science 125, 1-14 (Year: 2012).*
Altschul et al. "Basic Local Alignment Search Tool" Journal of Molecular Biology, 215:403-410 (1990).
Cote et al. "Generation of human monoclonal antibodies reactive with cellular antigens" Proceedings of the National Academy of Sciences USA, 80:2026-2030 (1983).
International Search Report and the Written Opinion of the International Searching Authority corresponding to International Patent Application No. PCT/EP2016/078075 (14 pages) (dated Jan. 30, 2017).
Kohler et al. "Continuous cultures of fused cells secreting antibody of predefined specificity" Nature, 256:495-497 (1975).
Kozbor et al. "The production of monoclonal antibodies from human lymphocytes" Immunology Today, 4(3):72-79 (1983) (Abstract only).
Tilley et al. "Cilia Dysfunction in Lung Disease" Annual Review of Physiology, 77:379-406 (2015).
United Kingdom Search Report corresponding to British Patent Application No. GB1520258.3 (5 pages) (dated Aug. 23, 2016).
Cao, Qi et al. "The central role of EED in the orchestration ofpolycomb group complexes" Nature Communications, 5 (3127), 13 pages (2014).
Zencak, D. "The Bmi1 polycomb gene as a target for therapies against retinal degeneration" Society for Neuroscience Abstract Viewer and Itinerary Planner, Abstract, vol. 38 (2008).
Zencak, Dusan et al. "Retinal degeneration depends on Bmi1 function and reactivation of cell cycle proteins" Proceedings of theN ational Academy of Sciences of the United States of America, 110(7):E593-601 (2013).
Waters, Aoife M. et al. "Ciliopathies: an expanding disease spectrum" Pediatric Nephrology, 26(7):1039-1056 (2011).
Ullius, Andrea et al. "The interaction ofMYC with the trithorax protein ASH2L promotes gene transcription by regulating H3K27 modification" Nucleic Acids Research, 42(11):6901-6020 (2014).

* cited by examiner

*Primary Examiner* — Arthur S Leonard
(74) *Attorney, Agent, or Firm* — Myers Bigel, P.A.

(57) ABSTRACT

The disclosure is based on the finding that compounds capable of binding to (or interacting with) chromatin binding/remodelling complexes (for example Polycomb group PRC1 and Trithorax group MLL) and/or modulation of the same can be used to modulate (for example switch on/off) ciliogenesis as may occur, for example, in the human pulmonary bronchial epithelium. Provided are compounds, compositions, methods and medicaments which may be used to treat and/or prevent diseases and/or conditions associated with aberrant or defective ciliogenesis.

Figure 1:
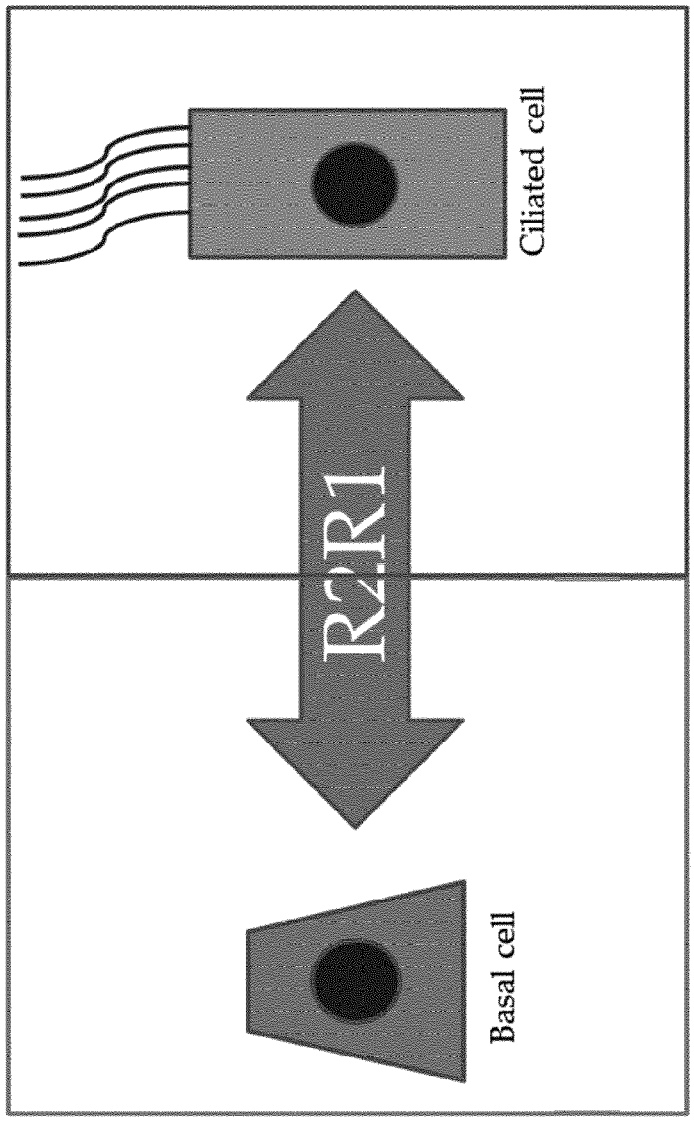

5 Claims, 46 Drawing Sheets
Specification includes a Sequence Listing.

MODULATION OF CILIOGENESIS

FIELD OF THE INVENTION

The present invention concerns ciliogenesis in cells and provides compounds, compositions, uses, medicaments and methods to be exploited in the modulation of ciliogenesis and in the prevention and/or treatment of diseases associated with the same.

BACKGROUND OF THE INVENTION

The protein designated R2R1 belongs to the FAM25 protein family and is essential for maintenance and regeneration of the pulmonary epithelium, more particular the basal cell program. Experiments in submerged Primary Bronchial Epithelial Cells (PBECs) uncovered this function. The submerged culture conditions are characterized by rapid cell proliferation of undifferentiated PBECs. Hence, submerged culture conditions are ideal for the study of basal cells ('the stem cells of the human bronchial pulmonary ('airway') epithelium.

Loss of ciliated cells leads to inefficient mucociliary clearance, in particular in patients suffering from COPD. This is in fact the pathological hallmark of COPD: the abnormal bronchial epithelium (loss of ciliated cells, squamous differentiation and basal cell hyperplasia) is unable to clear the airways of mucus, bacteria, viruses and debris. This ineffective clearance mechanism will cause severe symptoms (including coughing, bronchopulmonary infections and inefficient gas exchange in the lung), resulting in a high mortality rate.

The present invention aims to provide compounds, compositions, uses, medicaments and methods which exploit R2R1's role in ciliogenesis to provide treatments for disorders and diseases associated with the same.

SUMMARY OF THE INVENTION

The present invention stems from the finding compounds capable of binding to (or interacting with) chromatin binding/remodelling complexes (for example Polycomb group PRC1 and Trithorax group MLL) and/or modulation of the same can be used to modulate (for example switch on/off switch) ciliogenesis as may occur, for example, in the human pulmonary bronchial epithelium Specifically, a gene designated regenerative gene for respiratory cells 1 (R2R1) encodes a protein which has now been identified as a binding partner for components of the Polycomb Repressor Complex 1 (PRC1) and the Trithorax group-MLL (TrxG-MLL) complex. The PRC1 complex consists of a set of defined Polycomb group (PcG) proteins. The TrxG-MLL complex, also called COMPASS-like complex, consists of a set of defined Trithorax group (TrxG) proteins. Interaction between the R2R1 protein and the PRC1/trxG-MLL complexes and/or PcG or TrxG proteins, results in modulation of ciliogenesis in the human bronchial epithelium.

In a first aspect, the invention provides compounds which bind, associate or interact with chromatin binding/remodelling complexes for use in treating and/or preventing diseases and/or conditions associated with aberrant or defective ciliogenesis.

Further provided is the use of a compound which binds, associates or interacts with chromatin binding/remodelling complexes in the manufacture of a medicament for treating and/or preventing diseases and/or conditions associated with aberrant or defective ciliogenesis.

Also provided is a method of treating and/or preventing diseases and/or conditions associated with aberrant or defective ciliogenesis, said method comprising the step administering a subject in need thereof, a therapeutically effective amount of a compound which binds, associates or interacts with chromatin binding/remodelling complexes. PRC1-class complexes compact chromatin and inhibit chromatin remodelling. Likewise the Trithorax group-MLL (TrxG-MLL) complex is also involved in chromatin binding/remodelling.

Thus a further aspect of this invention provides compounds which bind, associate or interact with PRC1 and/or TrxG-MLL, for use in treating and/or preventing diseases and/or conditions associated with aberrant or defective ciliogenesis.

A yet further aspect provides the use of a compound which binds, associates or interacts with PRC1 and/or TrxG-MLL, in the manufacture of a medicament for the treatment and/or prevention of diseases and/or conditions associated with aberrant or defective ciliogenesis.

The invention further provides a method of treating or preventing diseases or conditions associated with aberrant or defective ciliogenesis, said method comprising administering a subject in need thereof, a therapeutically effective amount of a compound which binds, associates or interacts with PRC1 and/or TrxG-MLL.

Without wishing to be bound by theory and as explained in more detail below, the inventors have discovered that the R2R1 protein may bind to or associated/interact with components (for example protein or peptide components) of chromatin binding/remodelling complexes, including, for example, PRC1 and the TrxG-MLL complex; in doing so, the R2R1 protein may act as an "on/off" switch for ciliogenesis in the human bronchial epithelium. As such, compounds which modulate or mimic the expression, function and/or activity of R2R1 may be used as a means to modulate (for example restore, enhance or inhibit (i.e. switch "on/off")) ciliogenesis in cells and/or as the basis of treatments for diseases, conditions and/or syndromes caused or contributed to by aberrant or defective ciliogenesis. Compounds which modulate or mimic the expression, function and/or activity of R2R1 may bind to or otherwise associate with R2R1 binding sites present within chromatin binding/remodelling complexes, including the PRC1/TrxG-MLL complexes or within certain (or specific) components thereof. The effect of any binding to, or association with, R2R1 binding sites within these (PRC1/TrxG-MLL) complexes (or components thereof), may be the modulation of ciliogenesis in cells. Thus, compounds which bind to and/or associate with R2R1 binding sites within these complexes (for example PRC1/TrxG-MLL R2R1 binding sites) may be used or exploited in order to modulate ciliogenesis and/or in the treatment and/or prevention of diseases, conditions and/or syndromes associated with or caused or contributed to by, aberrant or defective ciliogenesis.

In view of the above, this disclosure relates to compounds for use (which compounds are capable of binding, associating or interacting with chromatin binding/remodelling complexes, PRC1, TrxG-MLL and/or R2R1 binding sites thereof), compositions (comprising one or more compounds capable of binding, associating or interacting with chromatin binding/remodelling complexes, PRC1, TrxG-MLL and/or R2R1 binding sites thereof) for use, uses of compositions/medicaments comprising compounds capable of binding, associating or interacting with chromatin binding/remodelling complexes, PRC1,TrxG-MLL and/or R2R1 binding sites thereof and methods exploiting the same. Additionally, the invention relates to compounds (for use), compositions (for use), medicaments (for use) and methods which exploit compounds which mimic or modulate the expression, function and/or activity of R2R1. Compounds which mimic the function of R2R1 may exhibit one or more properties and/or functions of a wild type R2R1 protein. For example, an R2R1 mimic might bind to or associate with PRC1,TrxG-MLL or a component or subunit thereof. R2R1 mimic type compounds may, for example, bind to or associate with chromatin binding/remodelling complexes, PRC1, TrxG-MII or a component thereof via an R2R1 binding site—in other words, an R2R1 mimic type compound may bind to or associate/interact with a chromatin binding/remodelling complex, PRC1 and/or TrxG-MII R2R1 binding site. A compound which modulates the expression, function and/or activity of R2R1 might enhance or inhibit the expression, function and/or activity thereof. A compound for use in this invention may interfere with, prevent or inhibit binding between native or wild type R2R1 and PRC1TrxG-MLL and/or a component or subunit of either.

Throughout this disclosure, these aspects and embodiments will be referred to as "compounds, compositions, uses, medicaments and methods". Further, the disclosure regularly refers to the terms "PRC1" and "TrxG-MII"—these are exemplary (but not necessarily limiting) examples of "chromatin binding/remodelling" complexes.

It should be understood that throughout this specification, the term "comprising" is used to denote that aspects and embodiments of this disclosure "comprise" a particular feature or features. It should be understood that the term "comprising" may also encompass aspects and/or embodiments which "consist essentially of" or "consist of" the relevant feature or features.

Polycomb Repressive Complex 1 (PRC1) is a multi-protein complex and compounds useful in the various aspects and embodiments of this invention (namely the uses, compositions, medicaments and methods) may include those that bind or associate with one or more of the PRC1 subunits or any R2R1 binding site thereof. PRC1 is known to interchange its components, resulting in canonical and non-canonical complexes. The effect of PRC1 on chromatin (H2A ubiquitylation, recruiting PRC2 and aiding PRC2 in its repressive form) is determined by its different component proteins. However, it is noted that the Ring Finger Protein 2 (RNF2) subunit of PRC1 is always present. In the context of this invention, the various compositions, uses, medicaments and methods may exploit a compound capable of binding the Ring Finger Protein 2 (RNF2) subunit of PRC1. A compound capable of binding or associating with RNF2 may target an R2R1 binding site thereof.

Compounds useful in the various aspects and embodiments of this invention (namely the uses, compositions, medicaments and methods) may include those that bind or associate with a component of the chromatin modifying TrxG-MLL (Trithorax Group-Mixed Lineage Leukemia) complex. In contrast to PRC1, TrxG-MLL maintains active gene expression by H3K4 methylation. In fact, the function of TrxG-MLL is complementary to the function of PRC1. PRC1 is responsible for repressive chromatin modifications and as a consequence is involved in heavy crosstalk with TrxG-MLL, the complex in control of chromatin modifications that activate transcription. TrxG-MLL comprises a core structure which itself comprises a number of sub-unit proteins, including, for example, the proteins designated DPY-30 and ASH2L. DPY-30 and ASH2L are always present in different TrxG-MLL complexes and are essential for the histone H3 Lys-4 (tri)methylation activity of TrxG-MLL. A compound of this invention may bind or associate with the TrxG-MLL complex via the DPY-30 and/or ASH2L component. In other words, a compound for use in this invention might bind or associate with DPY-30 and/or ASH2L. A compound capable of binding or associating with the DPY-30 and/or ASH2L component may target an R2R1 binding site of either (or both) of these components.

Compounds useful in the various aspects and embodiments of this invention (namely the uses, compositions, medicaments and methods) may further include those that bind the SF3B2 protein, a component of non-canonical PRC1 complexes. In the context of this invention, the various compositions, uses, medicaments and methods may exploit a compound capable the SF3B2 subunit of PRC1 A compound capable of targeting the R2R1 binding site of the SF3B2 subunit of PRC1 may target an R2R1 binding site thereof.

Compounds useful in the various aspects of this invention (which compounds bind to or associate with PRC1, TrxG-MLL (including components, subunits and/or R2R1 binding sites thereof) may take the form of nucleic acids (RNA, DNA and/or synthetic/artificial forms), antisense oligonucleotides, carbohydrates, proteins, peptides, small molecules, antibodies (including antigen or target binding fragments thereof).

A nucleic acid molecule for use in this invention (as an agent which expresses or encodes an R2R1 protein/peptide which binds (i) any of the complexes disclosed above (ii) to any R2R1 binding site thereof or (iii) which itself modulates the function, expression and/or activity of R2R1), may comprise or be derived from the sequence designated SEQ ID NO: 1 below.

SEQ ID NO: 1
acactgacacggaccgaaggagtggaaaaagctttacctgtcactgtctg ctgccatacgATGCTGGGAGGCCTGGGGAAGCTGGCGGCCGAGGGCCTGG

CCCACCGCACAGAGAAAGCCACTGGGGGAGCAGTTCACGCAGTGGAAGAG

GTGGTGAGCGAGGTGGTGGGCCACGCCAAGGAGGTTGGAGAGAAGACCAT

TAATGACGCCCTAAAGAAAGCCCAAGAATCAGGAGACAGGGTGGTGAAGG

AGGTCACTGAGAAGGTCACCCACACCATCACTGATGCTGTTACCCATGCG

GCAGAAGGCCTGGGAAGACTGGGACAGtgagcctgcctaccagcatggct ggccttcctgaaggtcaataaagagtgtgaaacgtgaaaaaaaaaaaaa aaataacaaaaaaaaaaaaaaaaaa SEQ ID NO: 1 represents an exemplary transcript of the murine R2R1 gene. The coding or translated part of this sequence is underlined and comprises some 267 nucleotides. This particular portion of SEQ ID NO: 1 shall be designated and referred to as SEQ ID NO: 2.

A nucleic acid molecule for use in this invention may comprise or be derived from the sequence designated SEQ ID NO: 3 below.

SEQ ID NO: 3
actgtctgctgccacacgATGCTGGGAGGCCTGGGGAAGCTGGCTGCCGA

AGGCCTGGCCCACCGCACCGAGAAGGCCACCGAGGGAGCCATTCATGCCG

TGGAAGAAGTGGTGAAGGAGGTGGTGGGACACGCCAAGGAGACTGGAGAG

-continued

```
AAAGCCATTGCTGAAGCCATAAAGAAAGCCCAAGAGTCAGGGGACAAAAA

GATGAAGGAAATCACTGAGACAGTGACCAACACAGTCACAAATGCCATCA

CCCATGCAGCAGAGAGTCTGGACAAACTTGGACAGtgagtgcacctgcta ccacggcccttccccagtctcaataaaaagccatgacatgtg
```

SEQ ID NO: 3 represents an exemplary transcript of the human R2R1 gene. The coding or translated part of this sequence is underlined and comprises some 267 nucleotides. This particular portion of SEQ ID NO: 3 shall be designated and referred to as SEQ ID NO: 4.

The 267 nucleotide residues of SEQ ID NO: 2 encode a protein/peptide comprising 89 amino acids and having the following sequence (designated SEQ ID NO: 5)

SEQ ID NO: 5
MLGGLGKLAAEGLAHRTEKATGGAVHAVEEVVSEVVGHAKEVGEKTINDA
LKKAQESGDRVVKEVTEKVTHTITDAVTHAAEGLGRLGQ

The 267 nucleotides of SEQ ID NO: 4 encode a protein/peptide comprising 89 amino acids and having the following sequence (designated SEQ ID NO: 6)

SEQ ID NO: 6
MLGGLGKLAAEGLAHRTEKATEGAIHAVEEVVKEVVGHAKETGEKAIAEA
IKKAQESGDKKMKEITETVINTVINAITHAAESLDKLGQ

Thus the invention concerns nucleic acid sequences comprising all or part (a portion or fragment) of SEQ ID NO: 1, SEQ ID NO: 2, SEQ ID NO: 3 or SEQ ID NO: 4, amino acid sequences encoded thereby as well as amino acid sequences comprising all or apart (a portion or fragment) of SEQ ID NO: 5 or SEQ ID NO: 6. The invention further concerns nucleic acid and/or amino sequences exhibiting some degree of identity and/or homology to all or a part (fragment) of SEQ ID NO: 1, SEQ ID NO 2, SEQ ID NO: 3, SEQ ID NO: 4, SEQ ID NO: 5 or SEQ ID NO: 6.

For convenience, the sequences of SEQ ID NOS: 1-6 (each of which encode or provide R2R$^1$ proteins) may be referred to hereinafter as "reference sequences".

A fragment of a reference sequence of this disclosure may comprise any number of nucleic acid/amino acid residues. For example, a fragment for use in this invention may comprise from about 5-10 residues to about n−1 residues, wherein "n" is the total number of (nucleic acid/amino acid) residues in the reference sequence. For example, a fragment or portion of a reference sequence of this invention may comprise at least about 5, 10, 15, 20, 25, 30, 35, 40, 45, 50, 75, 80, 85, 88, 90, 95, 100, 150, 200, 250, 265, 266, 267, 300, 341, 350, 400 or 424 residues—the upper limit (n−1) depending upon the size (n) of the nucleic acid sequence encoding the complete protein or the number (n) of amino acid residues comprising the complete primary sequence of the protein.

Homologous or identical sequences may be naturally occurring and found in mammalian animals such as rodents and/or humans. Using the nucleic acid and/or amino acid sequences described herein, one of skill in the art could readily identify related (for example homologous or identical) sequences within larger genomic sequences and in other species, such as other mammals etc. For example, a nucleic acid sequence derived from any of the nucleic acid sequences disclosed herein may be used as a probe to detect homologous/identical or closely related sequences within the genomes of other (non-murine or human) species.

Homologous or identical sequences may be constructed using, for example, molecular, sequencing, PCR and/or cloning techniques. One of skill in this field will readily understand that sequences homologous or identical to any of the sequences disclosed herein (referred to hereinafter as "reference sequences"), including (functional) fragments of such sequences, may exhibit as little as approximately 20 or 30% sequence homology or identity over all or part of the relevant sequence or fragment thereof. In other cases, homologous or identical sequences may exhibit at least 40, 50, 60, 65 70, 75, 80, 85, 90, 91, 92, 93, 94, 95, 96, 97, 98, 99% homology or identity to any of the sequences disclosed herein. For example, SEQ ID NOS 2 and 4—both of which provide nucleic acid sequences which are useful in the present invention (either as medicaments in their own right or as sequences which encode useful proteins or peptides) are 81.3% identical across the entire 267 amino acid length. Thus, with reference to sequence of SEQ ID NO: 2, for example, sequences which exhibit about 80% sequence homology identity may be useful. When one aligns the sequences of SEQ ID NOS: 1 and 3, the sequences are about 64% identical and as such, with reference to SEQ ID NO: 1, for example, sequences which exhibit about 64% sequence homology or identity may be useful.

The degree of (or percentage) "homology" between two or more (amino acid or nucleic acid) sequences may be determined by aligning the sequences and determining the number of aligned residues which are identical or which are not identical but which differ by redundant nucleotide substitutions (the redundant nucleotide substitution having no effect upon the amino acid encoded by a particular codon, or conservative amino acid substitutions). Homology may assessed by using the Basic Local Alignment Search Tool (BLAST: Altschul, S. F., Gish, W., Miller, W., Myers, E. W. & Lipman, D. J. (1990) "Basic local alignment search tool." J. Mol. Biol. 215:403-410).

A degree (or percentage) "identity" between two or more (amino acid or nucleic acid) sequences may also be determined by aligning the sequences and ascertaining the number of exact residue matches between the aligned sequences and dividing this number by the number of total residues compared—multiplying the resultant figure by 100 would yield the percentage identity between the sequences.

Each of the reference sequences encodes proteins or peptides which bind, interact or otherwise associate with (a component/components or R2R1 binding site of) PRC1 and/or TrxG-MLL; as such useful fragments of any one of the reference sequences described herein or indeed useful sequences which exhibit the required level of homology or identity to any of SEQ ID NOS 1-6 (or fragments thereof) may encode or provide a functional protein or peptide—that is a protein or peptide which exhibits an ability to bind, or an affinity for, PRC1 and/or TRXG-MLL and/or components or subunits of any of these. A protein or peptide which exhibits an ability to bind/associate to/with, or an affinity for, PRC1 and/or TRXG-MLL may bind/associate to/with or have affinity for, an R2R1 binding site thereof.

In view of the above, compounds useful in the various aspects of this invention may comprise, consist essentially of or consist of a nucleic acid disclosed herein (for example a nucleic acid provided by SEQ ID NO: 1, 2, 3 or 4), peptides/proteins encoded thereby as well as any of the proteins or peptides disclosed herein (for example a protein or peptide provided by SEQ ID NO: 5 or 6), nucleic acid or protein/peptide sequences comprising parts or fragments of the nucleic acid/amino acid sequences described herein, nucleic acid or protein/peptide sequences which exhibit some level of homology or identity to a nucleic acid or amino acid sequence disclosed herein.

Additionally, the invention may exploit variant nucleic acid or amino acid sequences. For example a variant nucleic acid or amino acid sequence may be a natural variant comprising (or harbouring or including), relative to a reference sequence of this invention, one or more polymorphisms or nucleic acid/amino acid additions, substitutions, inversions or deletions. Further, it is well known in the art, that the degeneracy of the genetic code permits substitution of one or more bases in a codon without alteration to the primary amino acid sequence. As such, genetic degeneracy may be exploited in order to yield variant nucleic acid sequences which encode peptide or protein sequences substantially identical to the reference sequences described herein. A useful variant sequence may also be generated through exploitation of one or more "conservative" residue substitutions. One of skill in this field will understand that the term "conservative substitution" is intended to embrace the act of, for example, replacing one or more amino acids of a reference protein or peptide sequence of this disclosure with an alternate amino acid with similar properties and which does not substantially alter the physico-chemical properties and/or structure or function of the native (or wild type) protein.

As such, it is to be understood that all such variants, especially those that are functional or display the desired activity or that encode functional peptides/proteins—that is to say, proteins/peptides which exhibit an ability to bind to or associate with the PRC1 and/or TrxG-MLL complexes and/or components or subunits of any of these, may be useful in the present invention The invention may exploit compounds (for example inhibitor compounds) which modulate the expression of R2R1 genes (exemplary sequences of which are provided as SEQ ID NOS: 1-4 above) and/or the activity, function and/or expression of the R2R1 proteins/peptides (exemplary sequences of which are provided as SEQ ID NOS: 5 and 6 above) in cells. For example, compounds for use in this invention may take the form of antisense oligonucleotides or RNAi type inhibitors. Compounds of this type are designed to interfere with the transcription/translation process by targeting specific DNA or RNA sequences. An antisense oligonucleotide/molecule may comprise DNA and/or RNA and may be used to significantly reduce or ablate the expression of the R2R1 gene or the proteinaceous product thereof. For example an antisense DNA sequence may comprise a short sequence complementary to a portion of any of the nucleic acid reference sequences disclosed herein. For example, an antisense sequence may comprise between about 5 and 50 contiguous nucleic acid residues of any of the sequences provided as SEQ ID NOS 1-4. An anti-sense RNA sequence for use in this invention may be complementary to some part of an R2R1 mRNA sequence. Other types of useful antisense or inhibitory RNA/DNA based molecules may include those known as microRNA (miRNA), small/short interfering RNA (siRNA) or shRNA. Such RNA oligonucleotides may be in the form of native RNA duplexes or duplexes which have been modified in some way (for example by chemical modification) to be nuclease resistant. Additionally, or alternatively, the RNA oligonucleotides may take the form of short hairpin RNA (shRNA) expression or plasmid constructs which correspond to or comprise siRNAs of the type described herein. Advantageously, potentially useful RNAi molecules may take the form of double-stranded RNA molecules. In all cases, the antisense DNA or RNA molecules may comprise sequences complementary to the R2R1 sequences disclosed herein. It should be noted that for all applications of the antisense technology described herein, techniques and protocols for achieving antisense control of gene expression are known and algorithms that computationally predict antisense sequences that have an optimal knockdown effect for a given gene may be used to design suitable antisense molecules/oligomers.

The invention may exploit recombinant compounds—in particular recombinant proteins/peptides and/or nucleic acid sequences. For example, using the reference sequences disclosed herein, one of skill may use molecular, cloning and PCR techniques to produce recombinant R2R1 sequences and/or proteins/peptides for use in this invention. Further information regarding the PCR and cloning based techniques for the production of recombinant sequences may be found in, for example, PCR Primer: A Laboratory Manual, Second Edition Edited by Carl W. Dieffenbach & Gabriela S. Dveksler: Cold Spring Harbour Laboratory Press and Molecular Cloning: A Laboratory Manual by Joseph Sambrook & David Russell: Cold Spring Harbour Laboratory Press.

The compounds for use in this invention may comprise antibodies (including antigen or target binding fragments thereof). The antibodies may bind R2R1 proteins/peptides (or epitopes thereof) or epitopes which correspond to, or are located within, the binding site occupied by R2R1 within the PRC1 and/or TrxG-MLL complex binding sites. The term "antibodies" may encompass polyclonal and/or monoclonal antibodies and, for example, IgG, IgM, IgD, IgE and/or IgA isotypes. Furthermore, the term "antibody fragments" should be construed as encompassing those comprising one or both lights chains and/or one or both heavy chains as well as those fragments known as Fab fragments, $Fab_2$ fragments and scfv fragments. Suitable antibodies and/or fragments thereof may be function and may include those that are capable of interfering with, blocking or neutralising the binding of R2R1 to the PRC1 and/or TrxG-MLL complexes. Alternatively, useful antibodies or fragments thereof may bind to the R2R1 binding site within the PRC1 and/or TrxG-MLL complexes. Antibodies or functional fragments thereof that bind to the R2R1 binding site within the PRC1 and/or TrxG-MLLcomplexes may be used to affect an R2R1 like function. In other words, antibodies (or functional fragments thereof) of this type may in the absence of R2R1 be used to replace R2R1 function.

As stated, the term antibody as used herein may include polyclonal and/or monoclonal antibodies. Polyclonal antibodies are heterogeneous populations of antibody molecules derived from the sera of animals immunised with an antigen, or an antigenic functional derivative thereof. Thus, in order to produce polyclonal antibodies with specificity or affinity for R2R1, host animals for example rabbits, sheep, pigs, etc., may be immunised (perhaps by injection) with an R2R1 protein/peptide (for example a protein or peptide encoded or provided by a sequence described herein or suitable (antigenic protein/peptide encoding) fragments thereof. The immunized animal would then produce antibodies with specificity and/or affinity to or for R2R1 and these could be harvested from the sera. Monoclonal antibodies are homogeneous populations of antibodies with specificity/affinity to or for a particular antigen or epitope thereof. They can be obtained by any technique which provides for the production of antibody molecules by continuous cell lines in culture. These include, but are not limited to, the hybridoma technique of Kohler and Milstein (1975), Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. U.S.A. 80:2026-2030), and the EBV-hybridoma technique (Cole et al., 1985, Monoclonal Anti-bodies and Cancer Therapy, Alan R. Liss, Inc., pp. 77-96). Monoclonal antibodies for use in this invention may be made using methods which exploit any of the nucleic acid, protein or peptide sequences disclosed herein (for example, proteins or peptides encoded by the nucleic acid sequences of any of SEQ ID NOS: 1-4 or the sequences of SEQ ID NOS: 5 or 6).

The compounds for use in this invention may further comprise small molecules (for example small organic compounds) that are able either to replace or inhibit the effects of R2R1. For example, small molecules that (i) interact or interfere with the binding of R2R1 to RNF2, DPY-30/ASH2L or SF3B2; (ii) inhibit the binding of R2R1 to RNF2, DPY-30/ASH2L or SF3B2; (iii) enhance the binding of R2R1 to RNF2, DPY-30/ASH2L or SF3B2 or (iv) modulate the binding of R2R1 to RNF2, DPY-30/ASH2L or SF3B2 may also find utility in this invention.

Compounds suitable for use in this invention (namely compounds which modulate ciliogenesis and/or are suitable for use in restoring ciliogenesis and/or treating or preventing disease) may be identified using methods which involve providing a test compound and contacting that compound with a cell and determining whether or not following contact with the test compound, there has been any modulation of ciliogenesis in the cell. Modulation of ciliogenesis may be detected by way of any observed increase or decrease in ciliogenesis and/or cilia formation, development or activity relative to the level of ciliogenesis or cilia formation, development or activity in a cell which has not been contacted with a (or the) test agent. A cell for use in a method of this type may be any cell capable of undergoing or executing ciliogenesis. The cell may be an undifferentiated, differentiating or a differentiated Primary Bronchial Epithelial Cell (PBEC) derived from human donors. The cell may also be an undifferentiated, differentiating or a differentiated iPS Cell (induced Pluripotent Stem Cell) with or without genetic modifications. For example, the iPS Cell may carry a genetic modification in the gene(s) coding for R2R1. The cells may be cultured under specific conditions, for example as a monolayer, in suspension or under air liquid interface conditions The term "aberrant or defective ciliogenesis" may embrace either excessive or inappropriate ciliogenesis or conditions in which the process of, or processes associated with, ciliogenesis have been ablated, are inhibited or have failed (or are failing). The term "aberrant or defective ciliogenesis" may include those diseases or conditions broadly classed as "ciliopathies". Loss of ciliogenesis may lead to an abnormal bronchial epithelium.

One of skill will appreciate that ciliogenesis is an important process leading to the formation of ciliated cells which play a crucial role in facilitating mucous clearance. The loss of ciliated cells (for example through some form of aberrant or defective ciliogenesis) may lead to inefficient mucociliary clearance in patients suffering from, for example, chronic obstructive pulmonary disease (COPD). In such cases, the abnormal bronchial epithelium (characterised by loss of ciliated cells, squamous differentiation and basal cell hyperplasia) is unable to clear the airways of mucus, bacteria, virus and other debris. This ineffective clearance mechanism may lead to severe symptoms including, for example, coughing, bronchopulmonary infections and inefficient gas exchange in the lung. Such complications are frequently associated with a high mortality rate.

As such, the various compounds described herein (which compounds are capable of binding to or interacting/associating with PRC1 and or TrxG-MLLand which may take the form of nucleic acids (sense/antisense DNA/RNA), proteins/peptides, small molecules and/or antibodies, may be useful be useful in the restoration or correction of ciliogenesis in cells exhibiting aberrant (for example reduced, inhibited, damaged, defective or ablated) ciliogenesis as described above. Other compounds (for example, nucleic acids (sense/antisense DNA/RNA), proteins/peptides, small molecules and/or antibodies) may be used to inhibit or reduce ciliogenesis in a cell.

One of skill will appreciate that aberrant ciliogenesis may be any ciliogenesis which, when compared to normal levels of ciliogenesis (as might occur in healthy cells) is increased or decreased. Aberrant ciliogenesis (whether increased or decreased) may be associated with a number of diseases including those referred to as ciliopathies (for example primary ciliary dyskinesia, hydrocephalus, polycystic liver and kidney disease and certain forms of retinal degeneration as well as nephronophthisis, Bardet-Biedl syndrome, Alstrom syndrome and Meckel-Gruber syndrome). Aberrant or defective ciliogenesis may also cause or contribute to diseases of the pulmonary system and airways, including, for example COPD and the like. As such, the various compounds described herein (which compounds are capable of binding to or interacting/associating with PRC1 and/or TrxG-MLL) may be useful in the treatment and/or prevention of ciliopathies and/or COPD. For example, the compounds of this invention may be used in order to restore ciliogenesis in patients suffering from or predisposed and/or susceptible to, COPD.

Compounds for use in this invention may be formulated as compositions for administration to subjects in need thereof. The compounds may be provided as pharmaceutical compositions. A composition for use may comprise a suitable (for example a pharmaceutically suitable) excipient, diluent and/or buffer. The compounds of this invention may be formulated together with one or more other compounds for administration—for example one or more other medicaments, which medicaments may be for the prevention and/or treatment of other diseases and/or diseases and/or conditions associated with ciliogenesis. Preferably, the pharmaceutical compositions provided by this invention are formulated as sterile pharmaceutical compositions.

Suitable excipients, carriers or diluents may include, for example, water, saline, phosphate buffered saline, dextrose, glycerol, ethanol, ion exchangers, alumina, aluminium stearate, lecithin, serum proteins, such as serum albumin, buffer substances such as phosphates, glycine, sorbic acid, potassium sorbate, partial glyceride mixtures of saturated vegetable fatty acids, water salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycon, sodium carboxymethylcellulose, polyacrylates, waxes, polyethylene-polypropylene-block polymers, polyethylene glycol and wool fat and the like, or combinations thereof.

A pharmaceutical formulation for use in this invention may be formulated, for example, in a form suitable for oral, parenteral, mucosal or topical administration. The composition may be formulated such that it can be inhaled. Compositions that are to be administered by inhalation may take the form of fine powders or solutions which can be aerosolised and inhaled as droplets. One of skill in this field will be familiar with devices that may be used to deliver compositions directly to the lung by, for example, inhalation. The droplet or particle size of the composition can be altered such that the drug can access different regions of the lung. For example, once inhaled, small particles or droplets may penetrate deep into the lung tissue and in some cases may reach the alveoli.

Compositions suitable for oral administration, wherein the carrier is a solid, are most preferably presented as unit dose formulations such as boluses, capsules or tablets each containing a predetermined amount of one or more of the PRC1 and/or TrxG-MLL binding compounds of this invention. A tablet may be made by compression or moulding, optionally with one or more accessory ingredients. Compressed tablets may be prepared by compressing in a suitable machine the active PRC1 and/or TrxG-MLL binding compound(s) in a free-flowing form such as a powder or granules optionally mixed with a binder, lubricant, inert diluent, lubricating agent, surface-active agent or dispersing agent. Moulded tablets may be made by moulding the active PRC1 and/or TrxG-MLL binding compound(s) with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. An active (for example a PRC1 and/or TRXG-MLL binding compounds of this invention) may also be formulated as dispersible granules, which may for example be suspended in water before administration, or sprinkled on food. The granules may be packaged, for example in a sachet. Formulations suitable for oral administration wherein the carrier is a liquid may be presented as a solution or a suspension in an aqueous or non-aqueous liquid, or as an oil-in-water liquid emulsion.

Compositions suitable for oral administration include controlled release dosage forms, for example tablets wherein the active PRC1 and/or TrxG-MLL binding compound(s) is/are formulated in an appropriate release-controlling matrix, or is coated with a suitable release-controlling film. Such compositions may be particularly convenient for prophylactic use.

Composition formulated for parenteral administration include sterile solutions or suspensions of active PRC1 and/or TrxG-MLL compounds of this invention in aqueous or oleaginous vehicles. Compositions of this invention, may comprise, or further comprise cryoprotectant compounds or compositions, preservative(s), antibiotics, adjuvants and the like. Injectable compositions and vaccines may be adapted for bolus injection or continuous infusion. Such preparations are conveniently presented in unit dose or multi-dose containers, which are sealed after introduction of the formulation until required for use. Alternatively, an active PRC1 and/or TrxG-MLL compound of this invention may be in powder form that is constituted with a suitable vehicle, such as sterile, pyrogen-free water or phosphate buffered saline PBS before use.

Compositions comprising one or more PRC1 and/or TrxG-MLL compounds of this invention may also be formulated as long-acting depot preparations, which may be administered by intramuscular injection or by implantation, e.g. subcutaneously or intramuscularly. Depot preparations may include, for example, suitable polymeric or hydrophobic materials, or ion-exchange resins. They may also include preparations or adjuvants known to enhance the affinity and/or longevity of an animal (for example bovine, ovine or caprine) immune response, such as single or double emulsions of oil in water. Such long-acting compositions are particularly convenient for prophylactic use.

Compositions suitable (or formulated) for mucosal administration include compositions comprising particles for aerosol dispersion, or dispensed in drinking water. When dispensed, such compositions should desirably have a particle diameter in the range 10 to 200 microns to enable retention in, for example, the nasal cavity; this may be achieved by, as appropriate, use of a powder of a suitable particle size or choice of an appropriate valve. Other suitable compositions include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that, in addition to the carrier ingredients mentioned above, the various compositions described herein may include an appropriate one or more additional (pharmaceutically acceptable) carrier ingredients such as diluents, buffers, flavouring agents, binders, surface active agents, thickeners, lubricants, preservatives (including antioxidants) and the like, and substances included for the purpose of rendering the formulation isotonic with the blood of the intended recipient. Pharmaceutically acceptable carriers are well known to those skilled in the art and include, but are not limited to, 0.1 M and preferably 0.05 M phosphate buffer or 0.8% saline. Additionally, pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringers or fixed oils. Preservatives and other additives may also be present, such as, for example, antimicrobials, antioxidants, chelating agents, inert gases and the like.

Compositions suitable for topical formulation may be provided, for example, as gels, creams or ointments.

Compositions for veterinary use may conveniently be in either powder or liquid concentrate form. In accordance with standard veterinary formulation practice, conventional water-soluble excipients, such as lactose or sucrose, may be incorporated in the powders to improve their physical properties. Thus, particularly suitable powders of this invention comprise 50 to 100% w/w and preferably 60 to 80% w/w of the active ingredient(s) (for example one or more PRC1 and/or TrxG-MLL compounds of this invention) and 0 to 50% w/w and preferably 20 to 40% w/w of conventional veterinary excipients. These powders may either be added to, for example, animal feed—perhaps by way of an intermediate premix, or diluted in animal drinking water.

Liquid concentrates of this invention suitably contain one or more PRC1 and/or TrxG-MLL compounds of this invention and may optionally further include an acceptable water-miscible solvent for veterinary use, for example polyethylene glycol, propylene glycol, glycerol, glycerol formal or such a solvent mixed with up to 30% v/v of ethanol. The liquid concentrates may be administered to the drinking water of animals.

DETAILED DESCRIPTION

The present invention will now be described in detail with reference to the following Figures which show:

FIG. 1: Illustration of the function of R2R1 in ciliogenesis.

Figure 2:
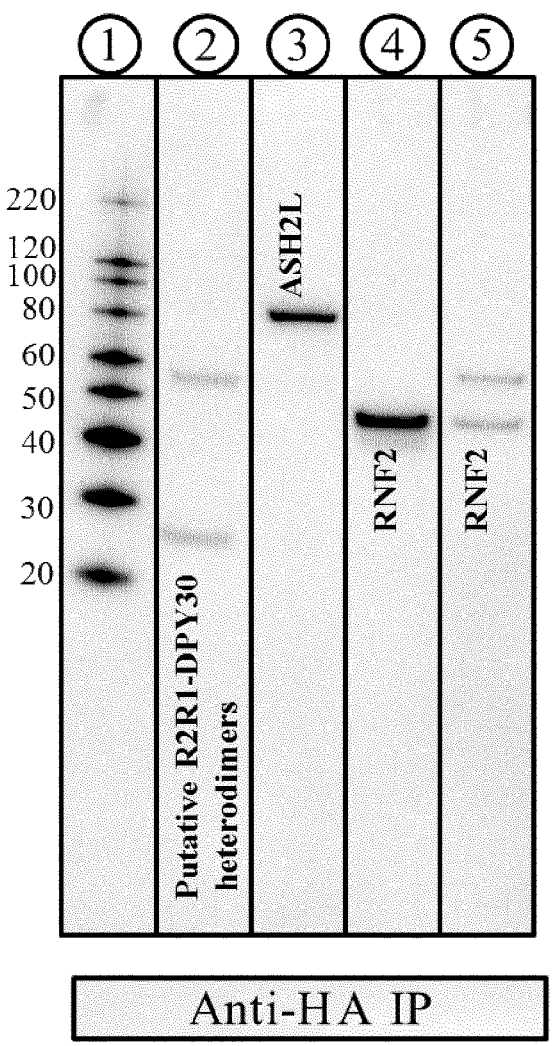

FIG. 2: illustration of Western Blot of R2R1 co-immunoprecipitation experiment.

Figure 3:
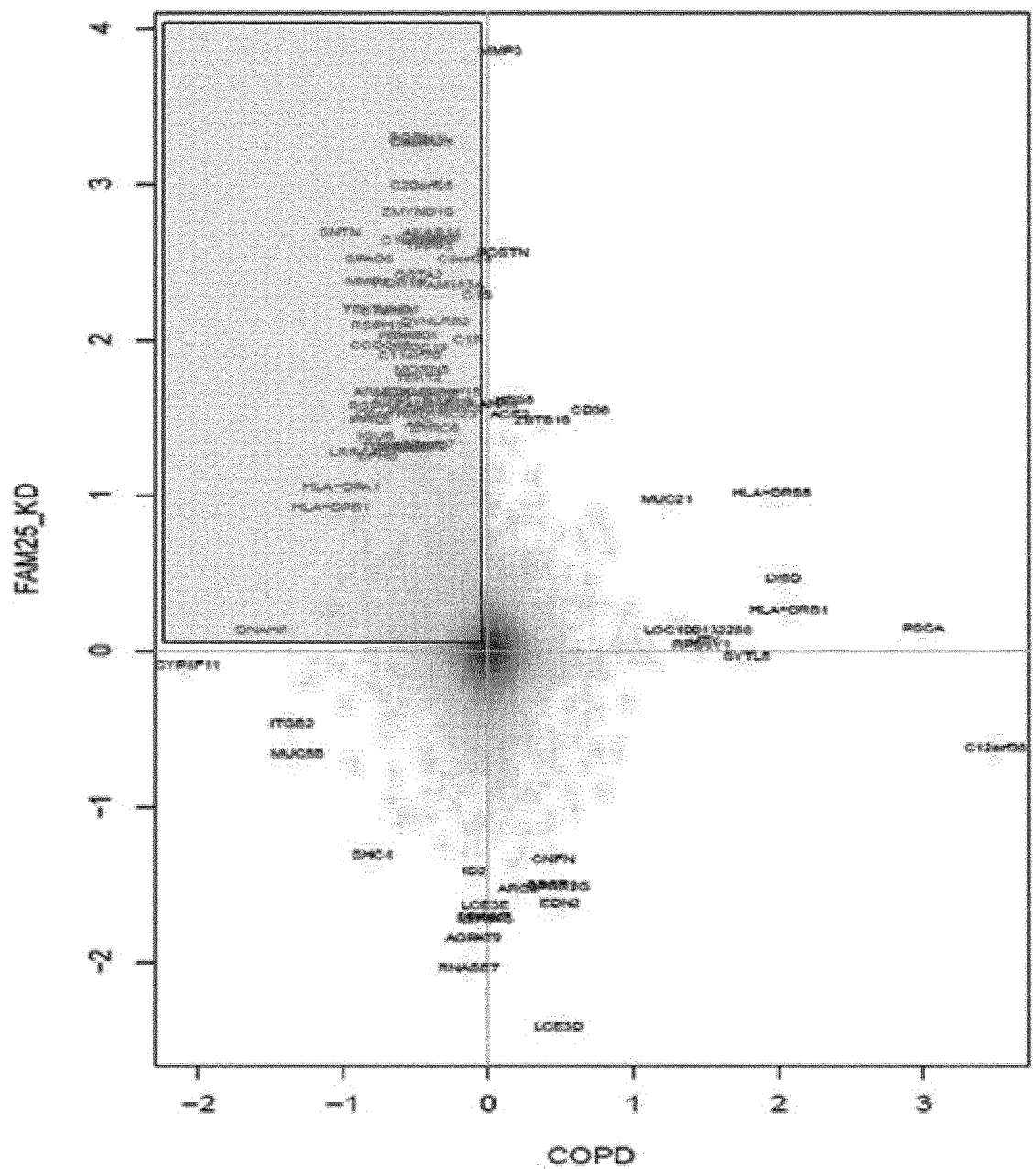

FIG. 3: Comparison of the logRatios representing differential expression for the transcriptional effect of R2R1 knockdown (FAM25_KD) and COPD disease status.

Figure 4:
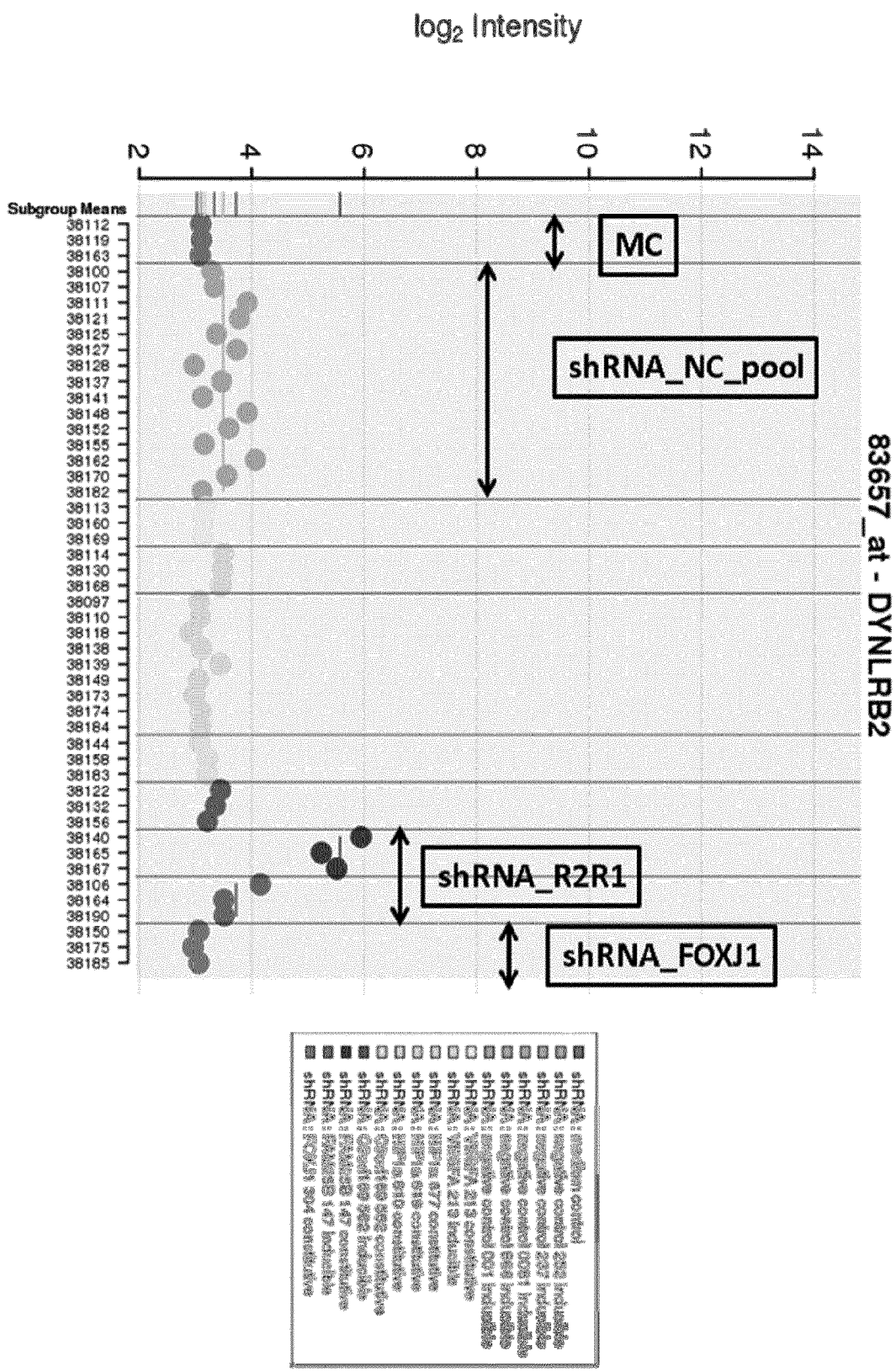
Figure 4:
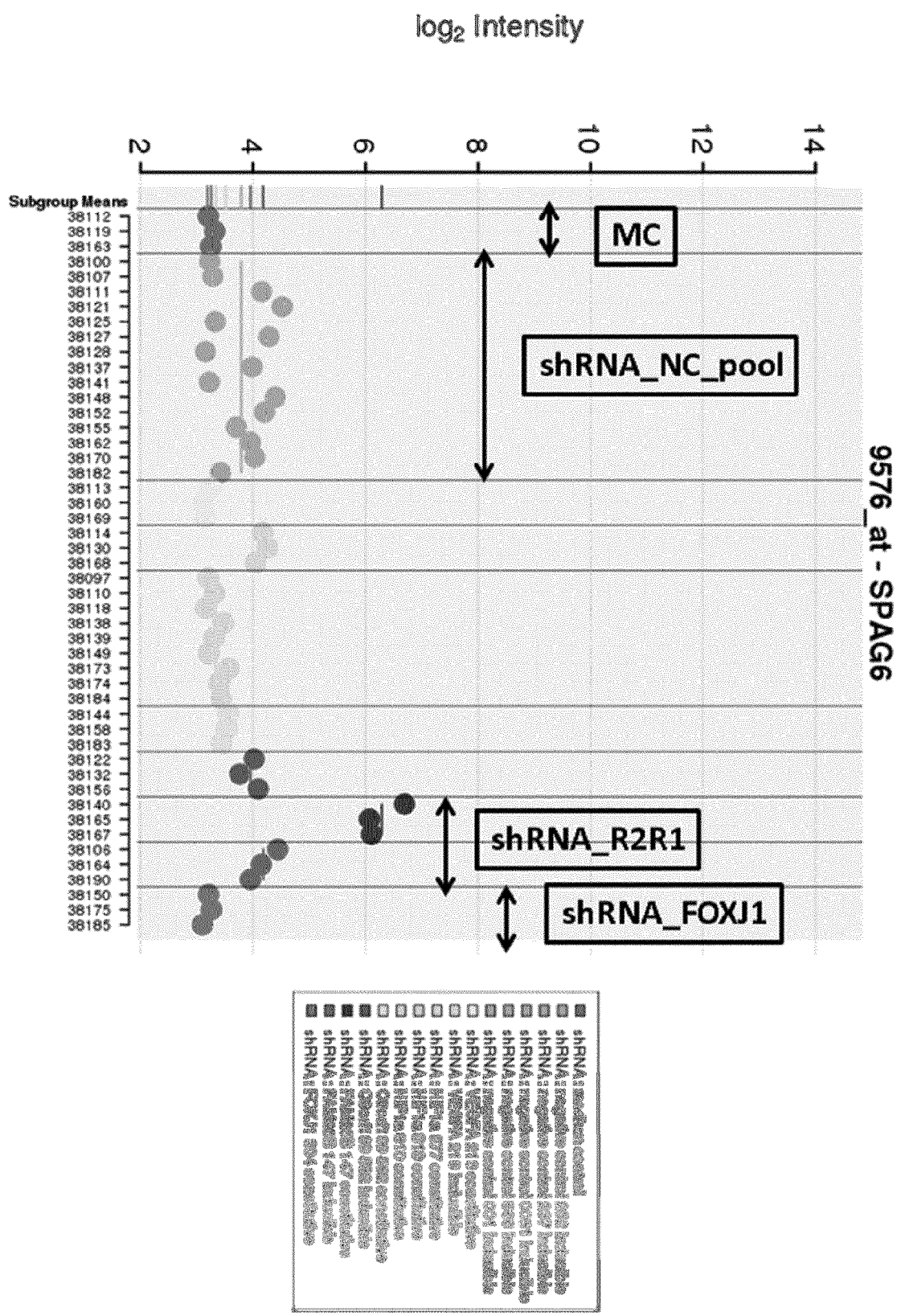
Figure 4:
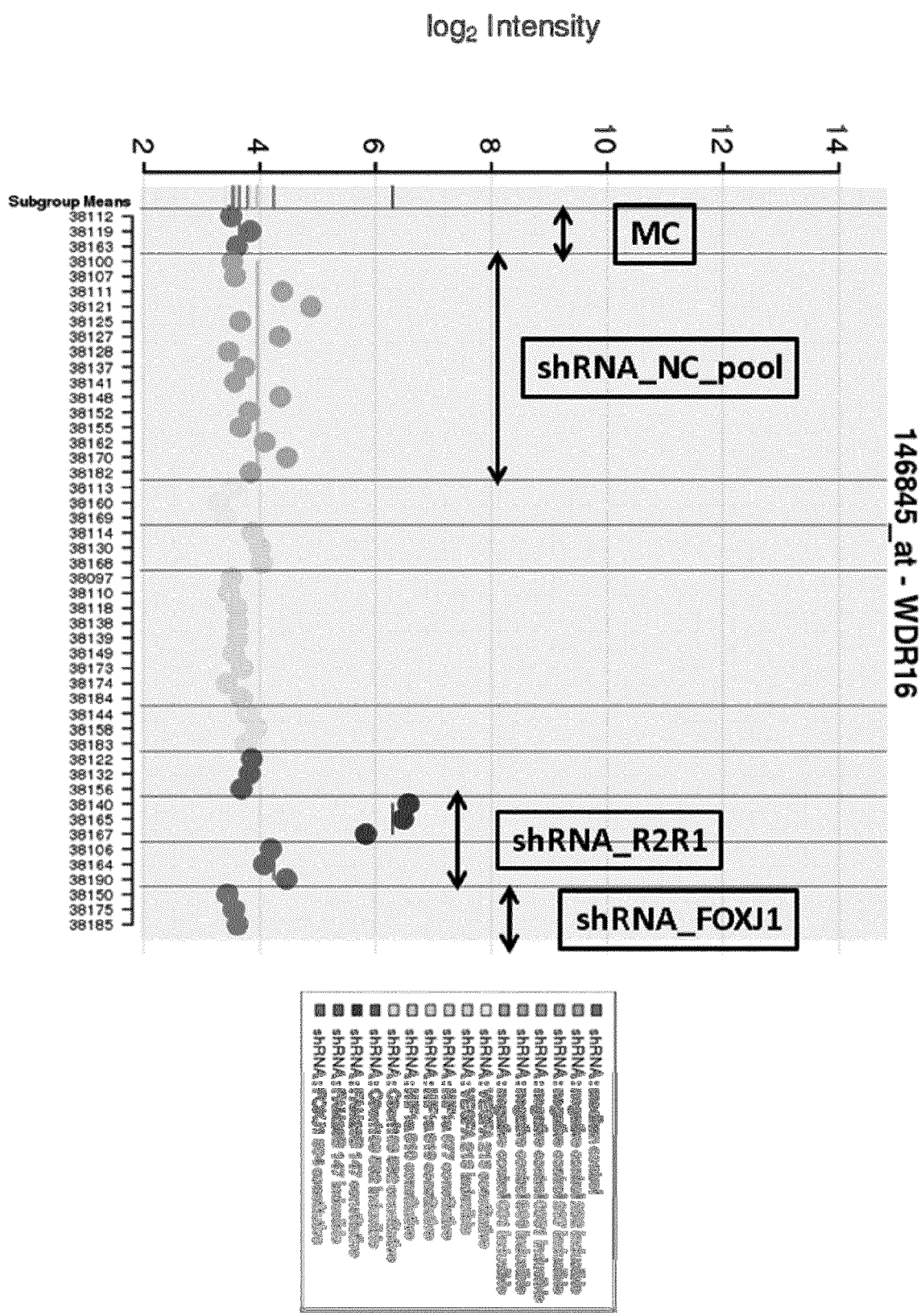
Figure 4:
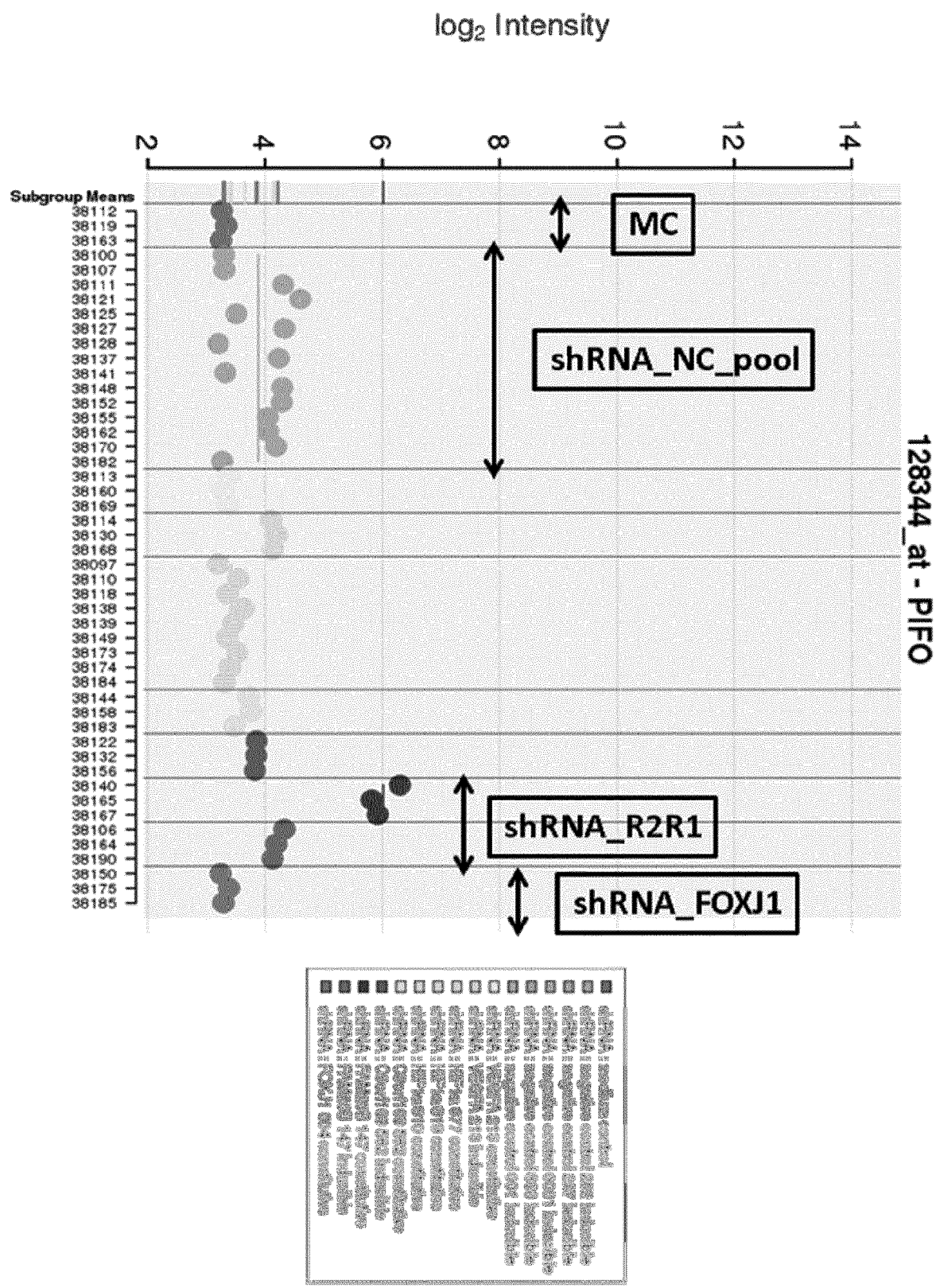
Figure 4:
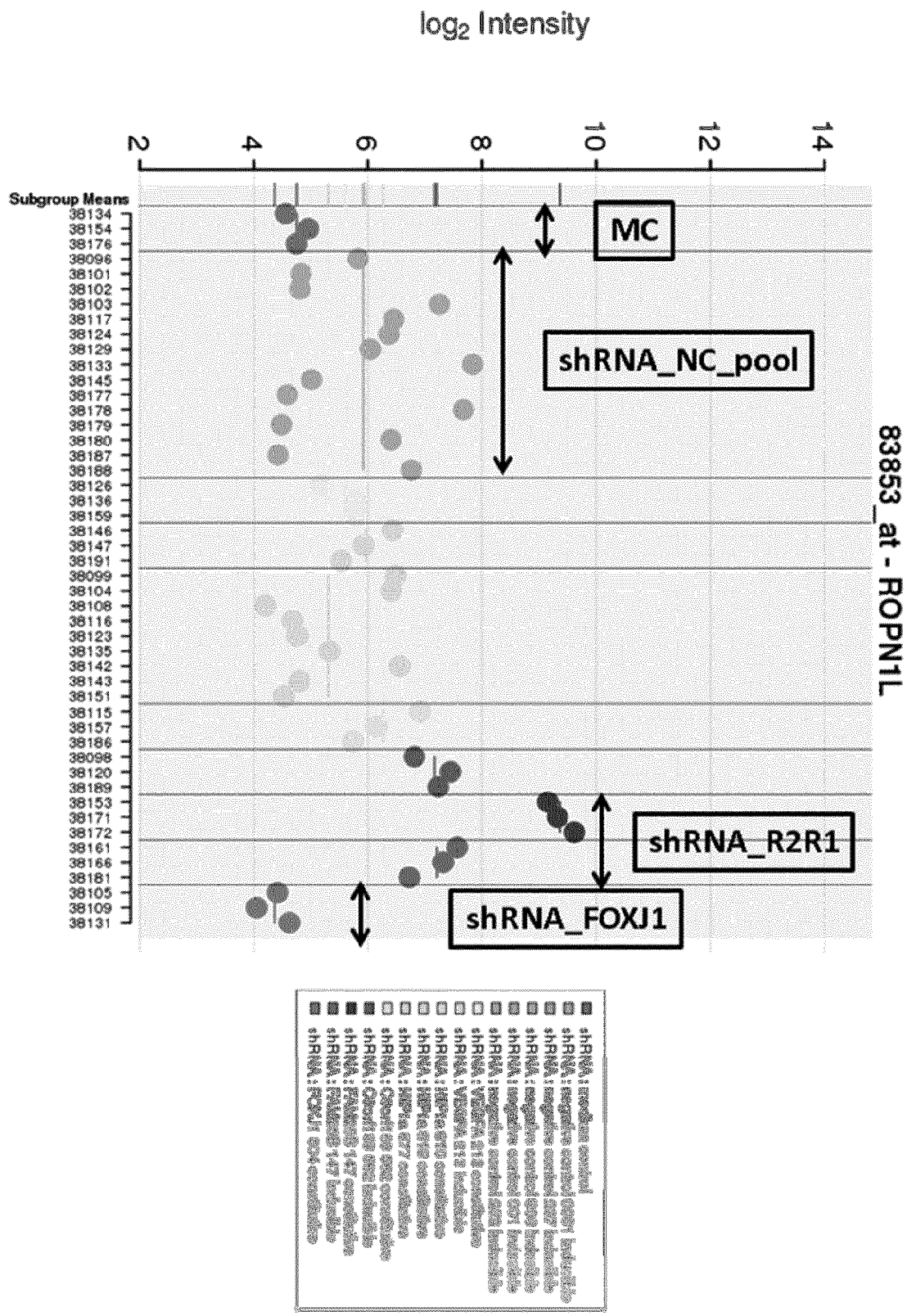

FIG. 4: $Log_2$ Intensity plots illustrating the upregulation of exemplary ciliary genes.

Figure 5:
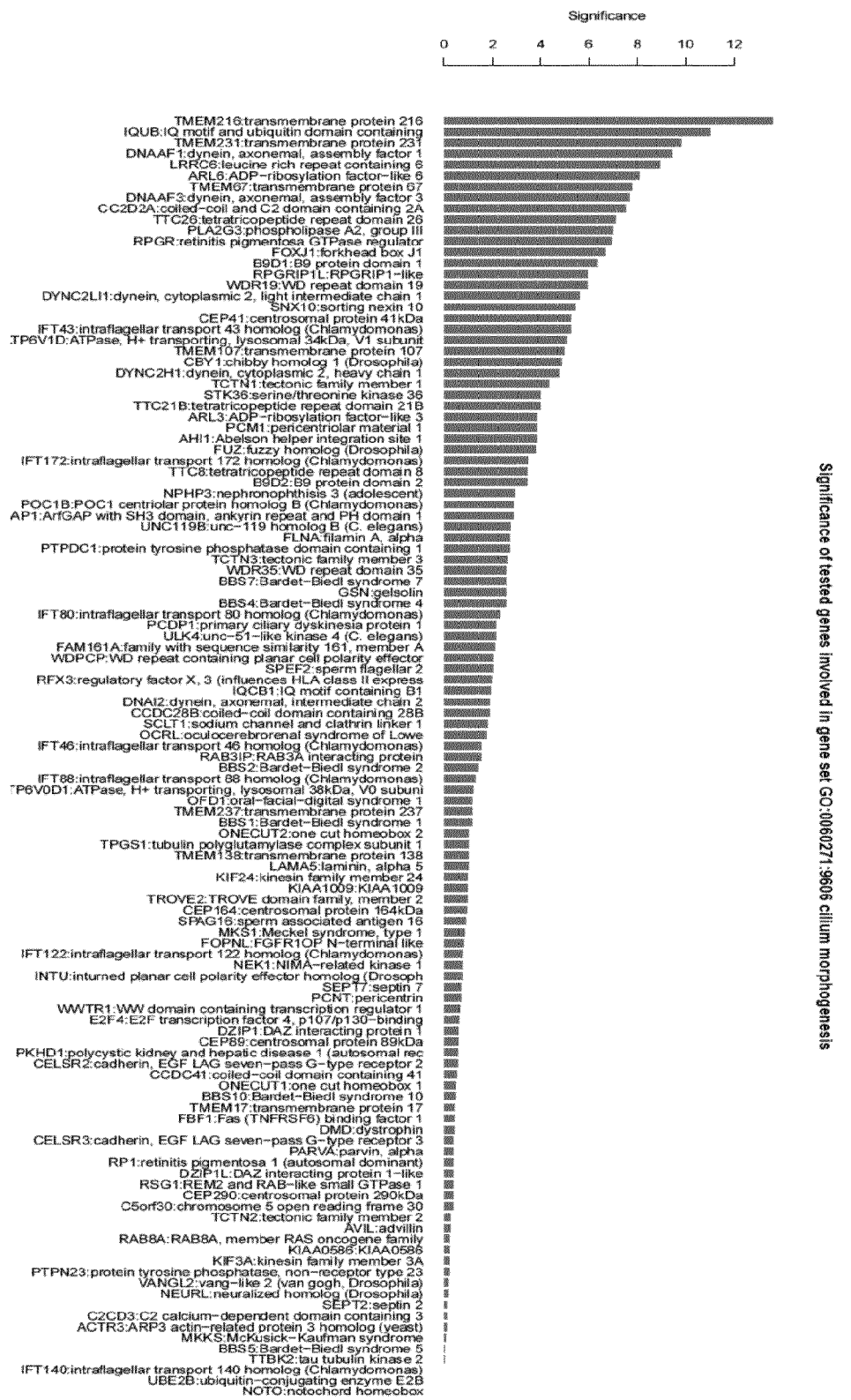
Figure 5:
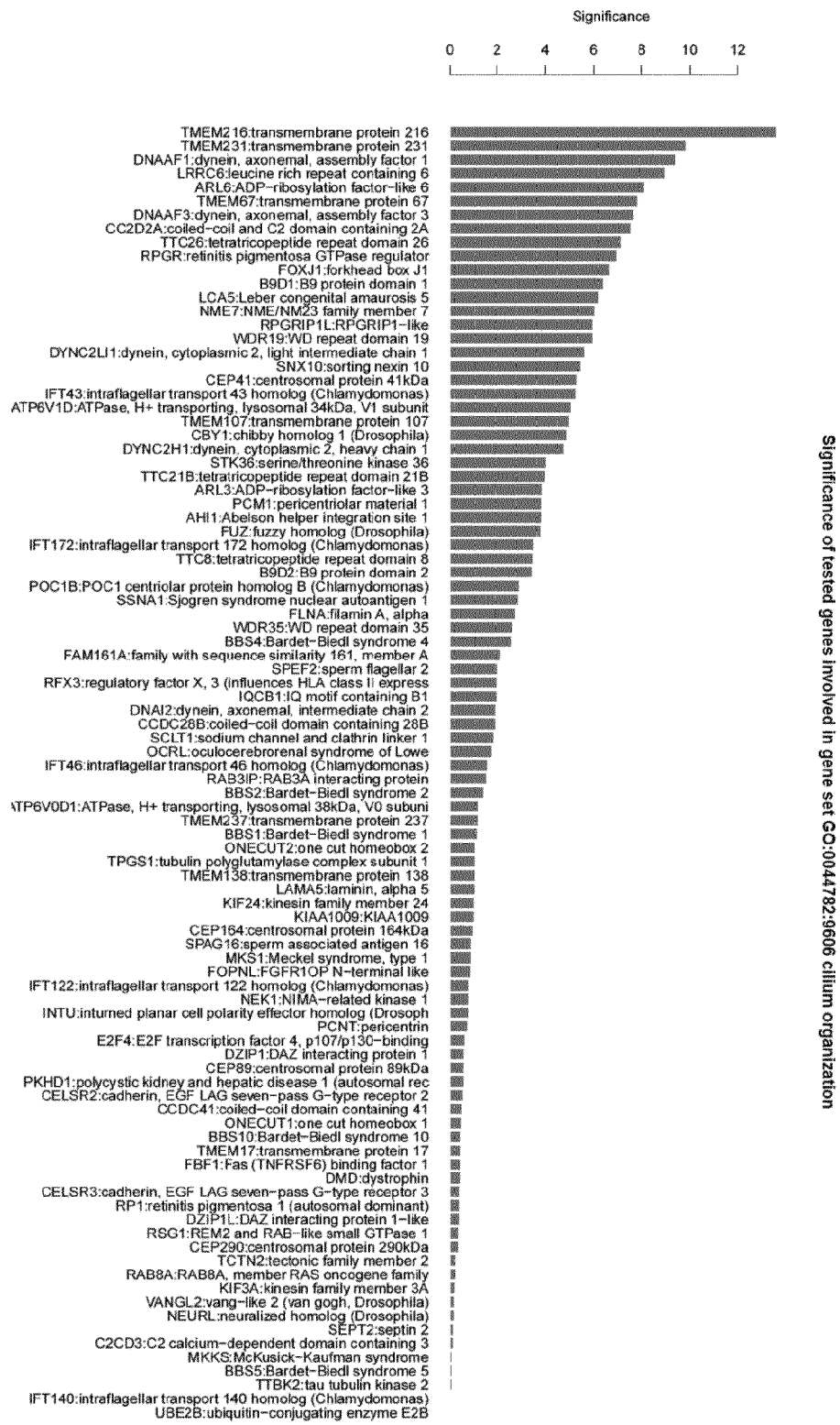
Figure 5:
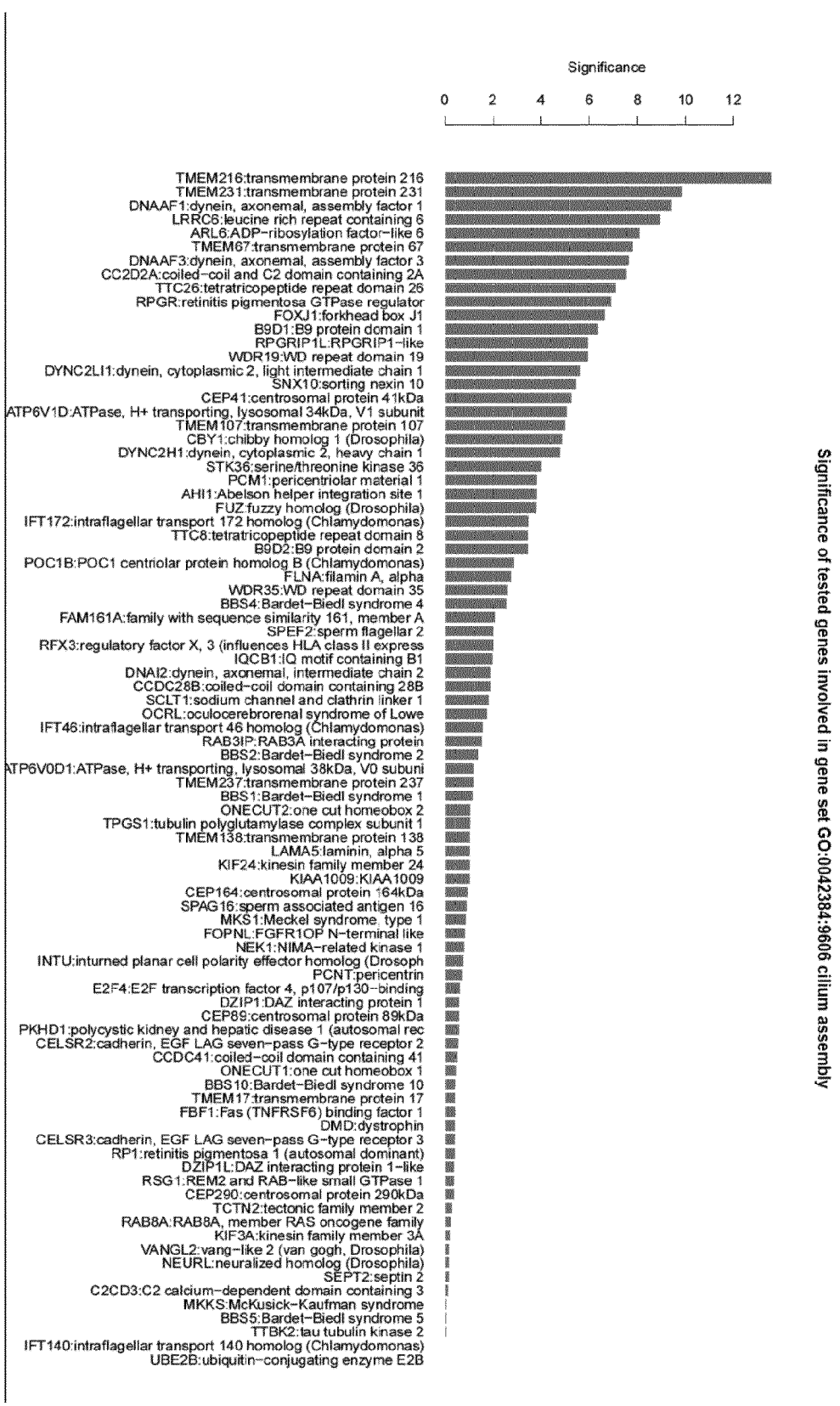
Figure 5:
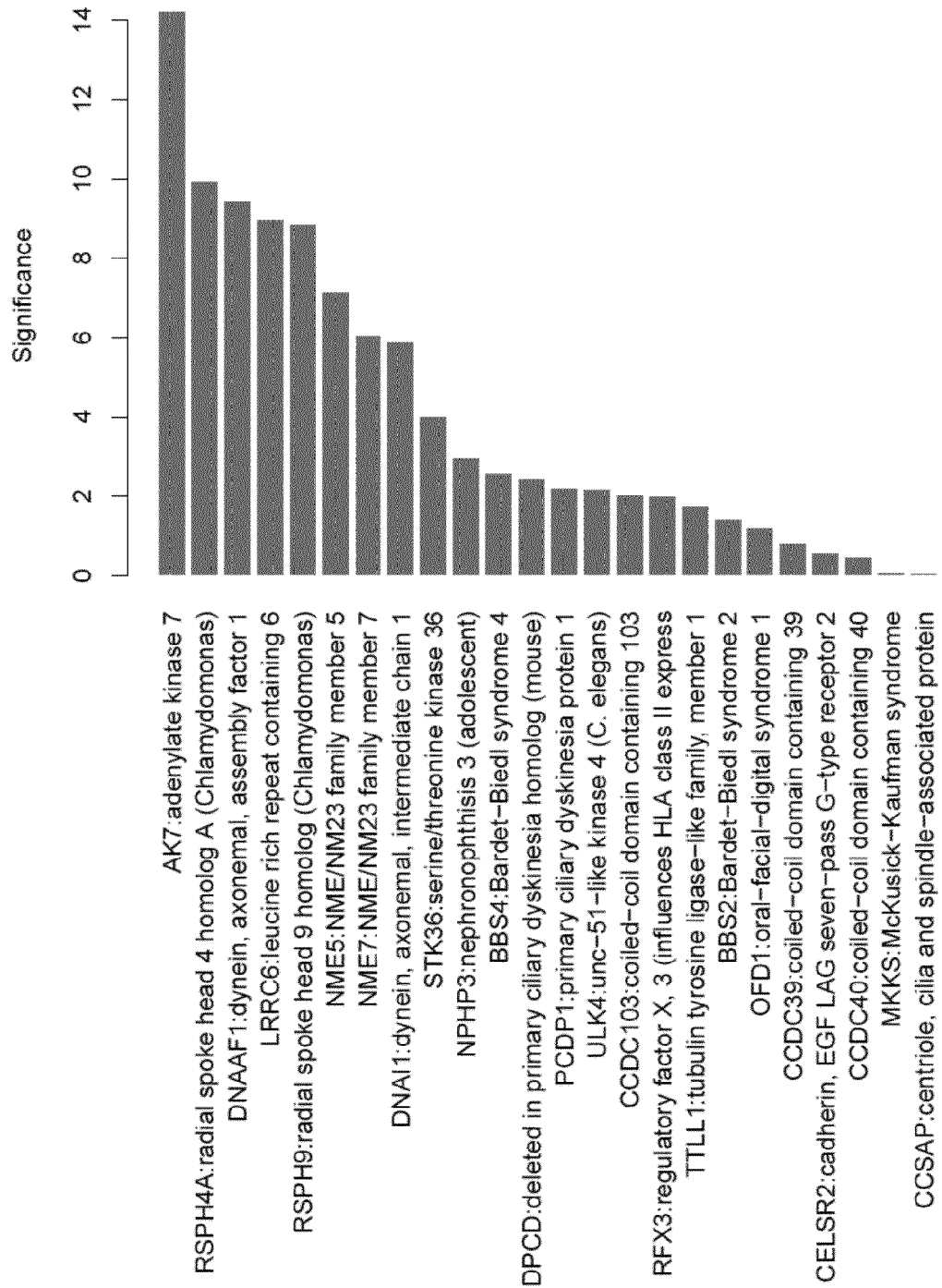
Figure 5:
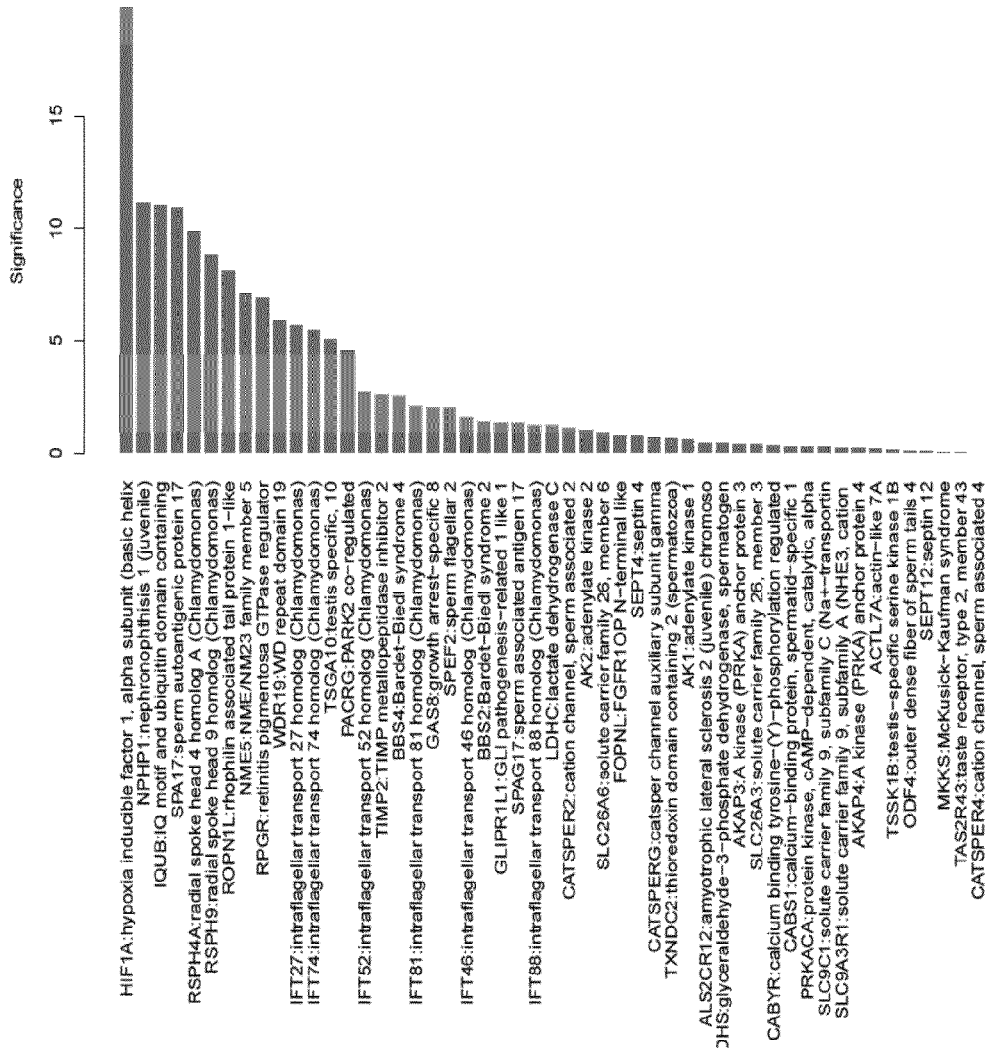
Figure 5:
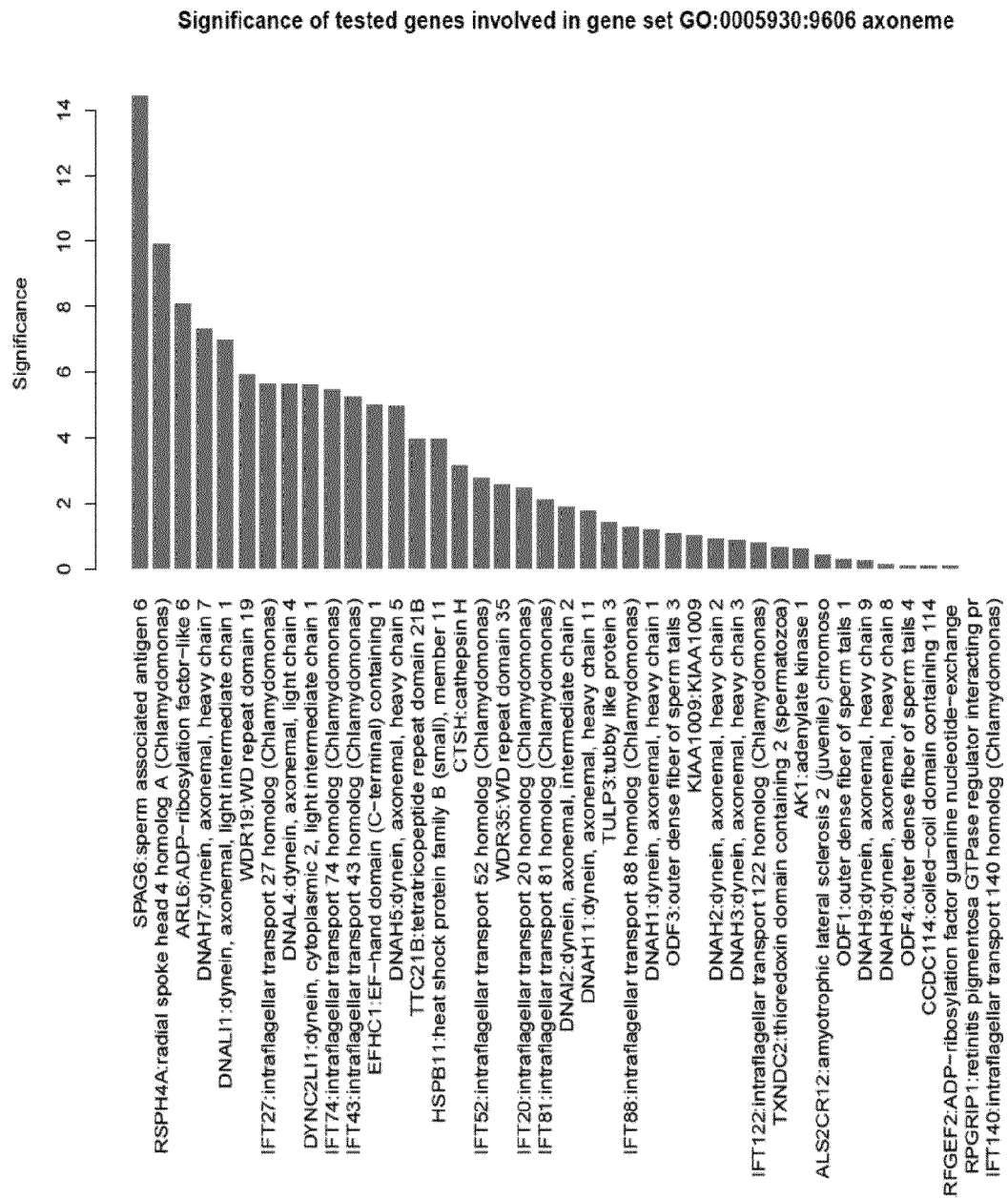
Figure 5:
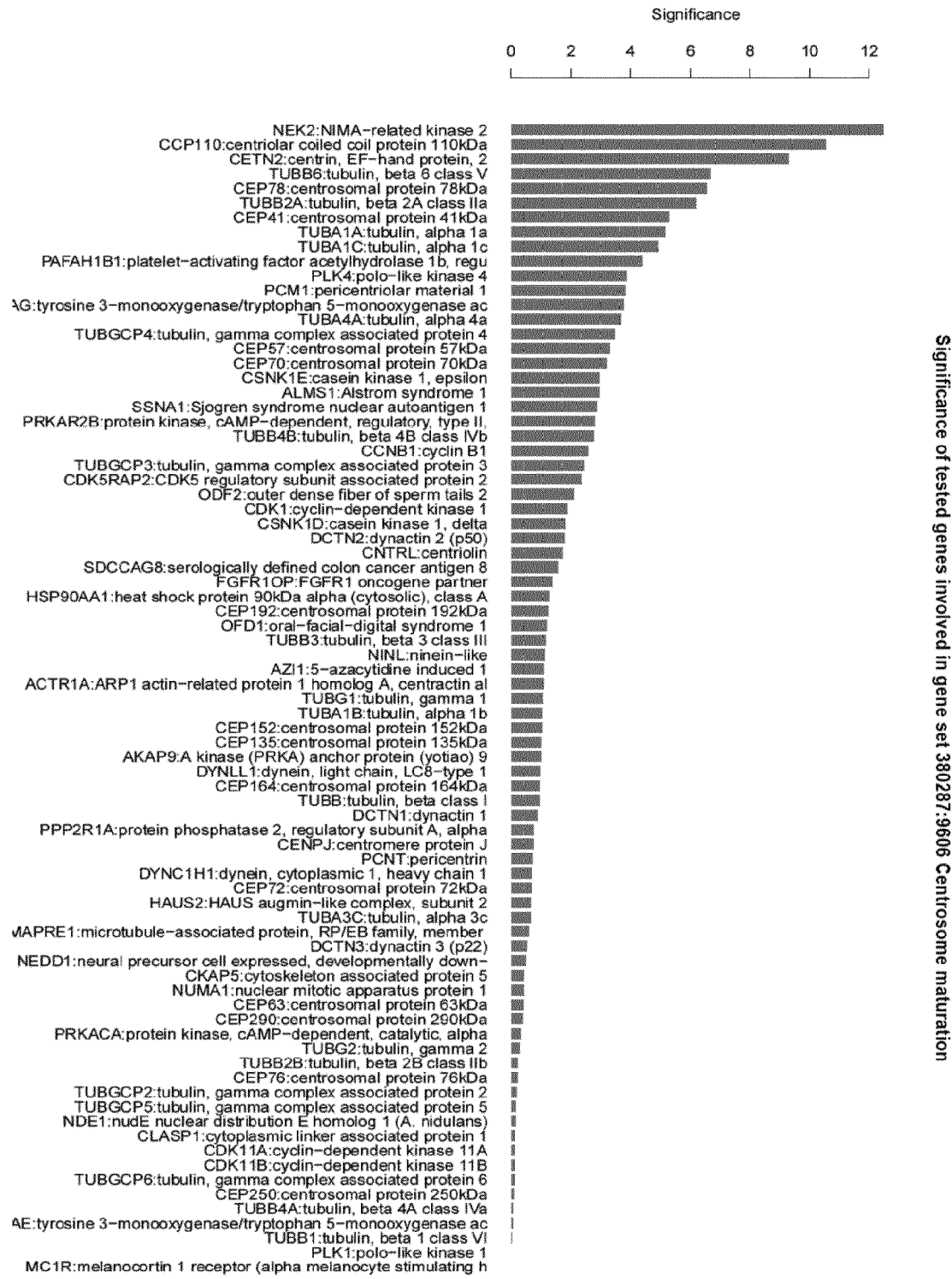
Figure 5:
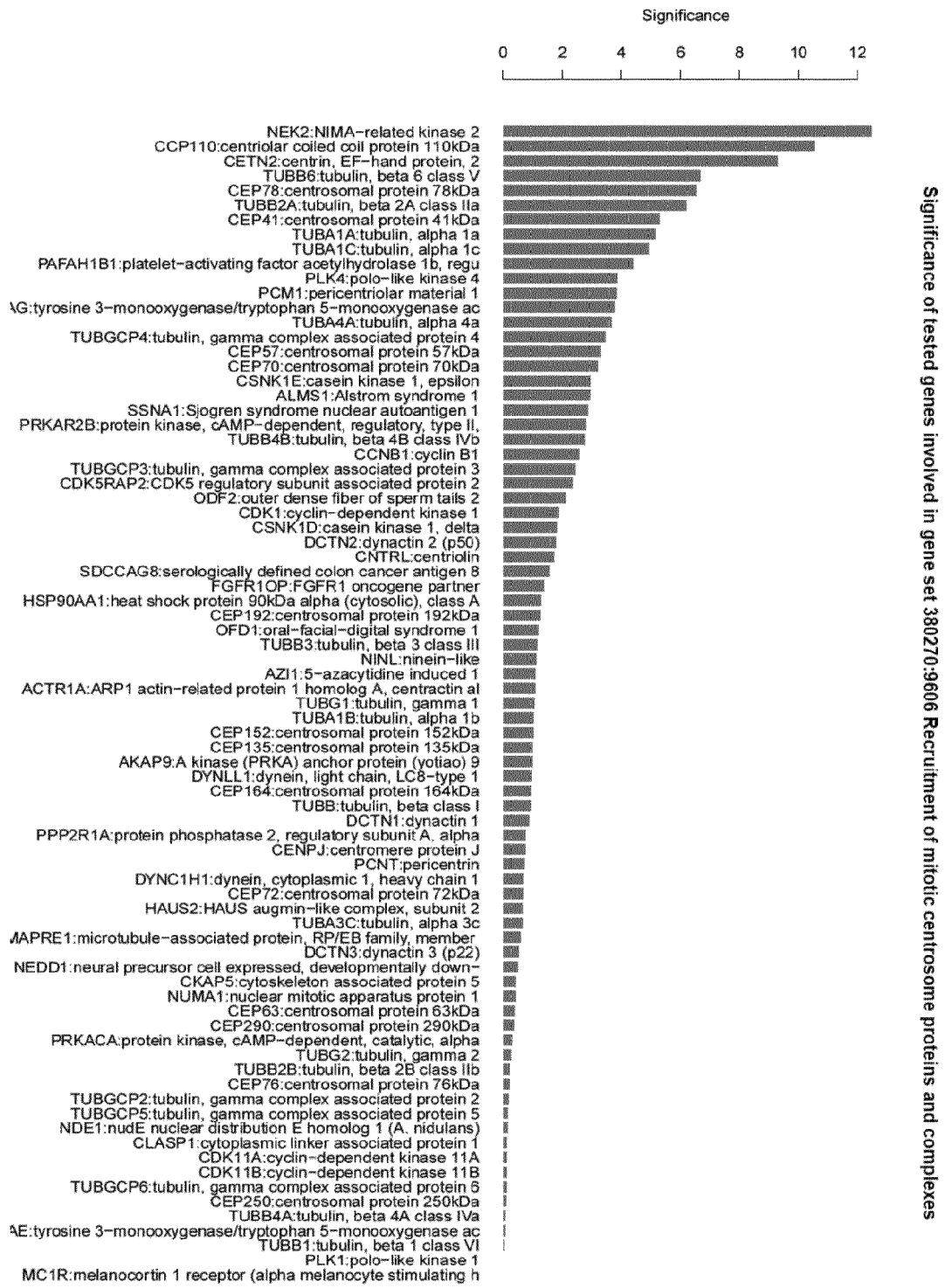

FIG. 5: boxplots illustrating the significance of differentially expressed ciliary genes upon shRNA mediated knockdown of FAM25 (R2R1) gene expression.

Figure 6:
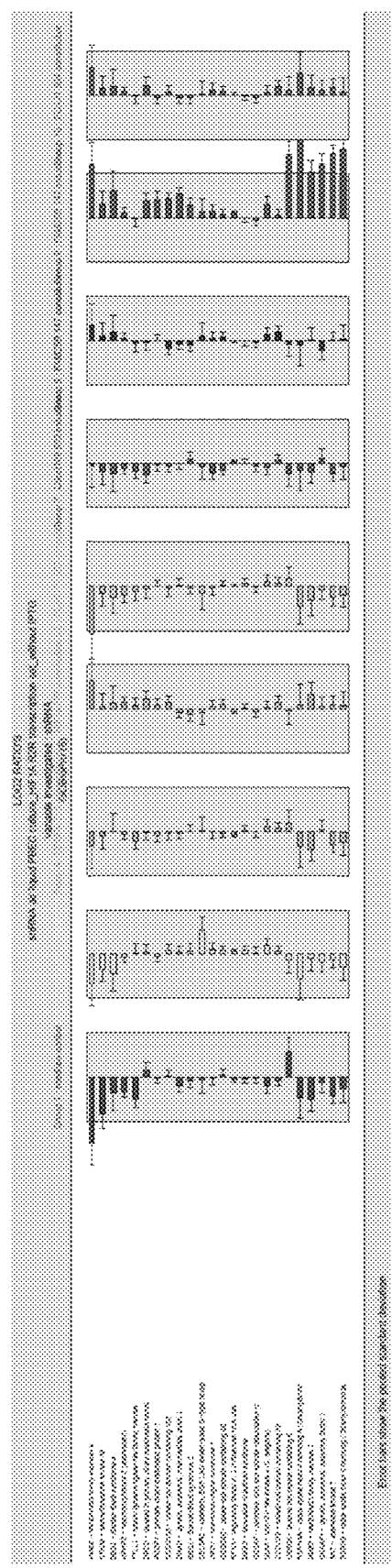

FIG. 6: $Log_2$ Ratio plot illustrating the upregulation of ciliary genes (ciliary movement) caused by shRNA mediated downregulation of FAM25 (R2R1) gene expression.

Figure 7:
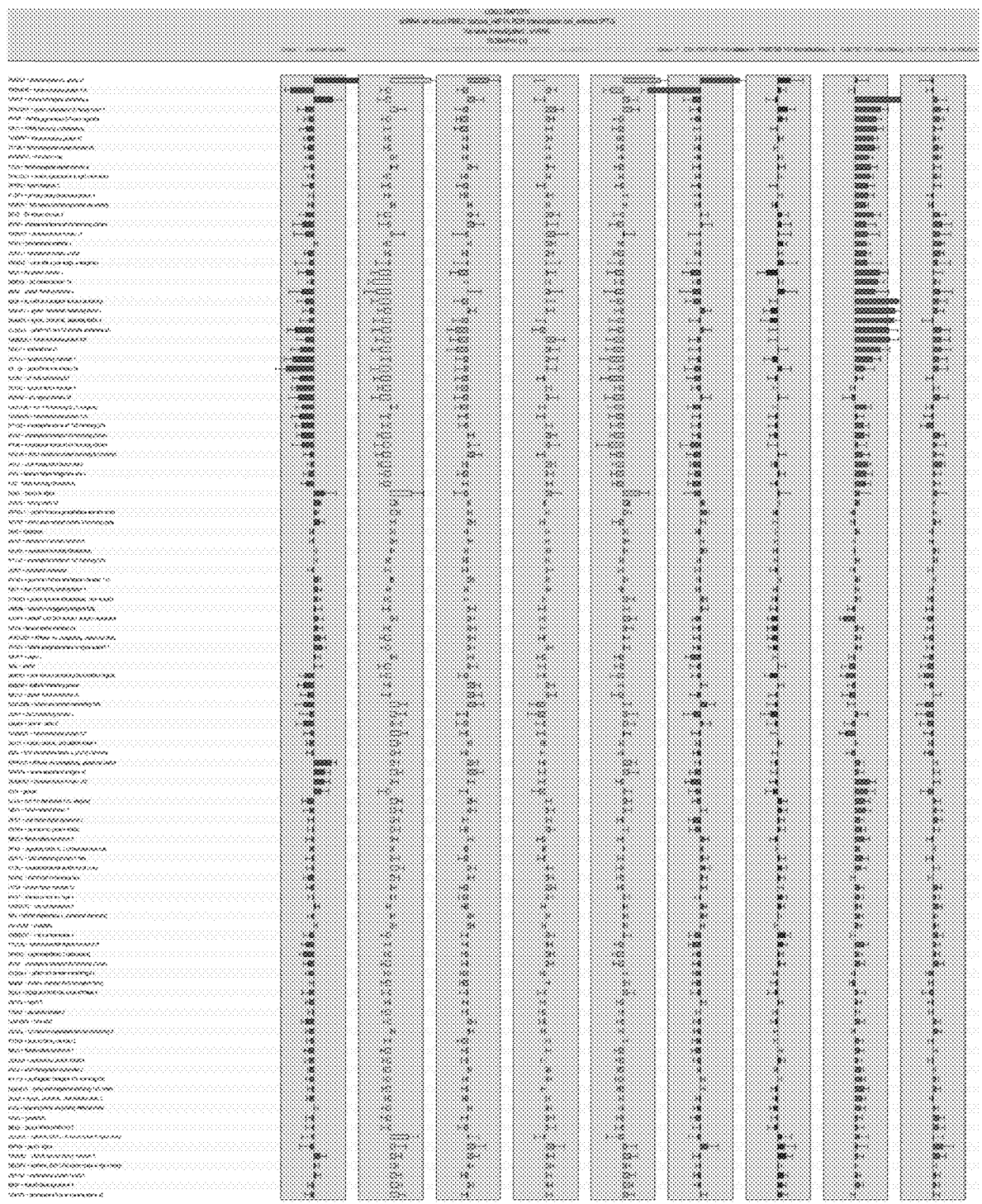

FIG. 7: Log 2 Ratio plot illustrating the upregulation of ciliary genes (cilium morphogenesis) caused by shRNA mediated downregulation of FAM25 (R2R1) gene expression.

Figure 8:
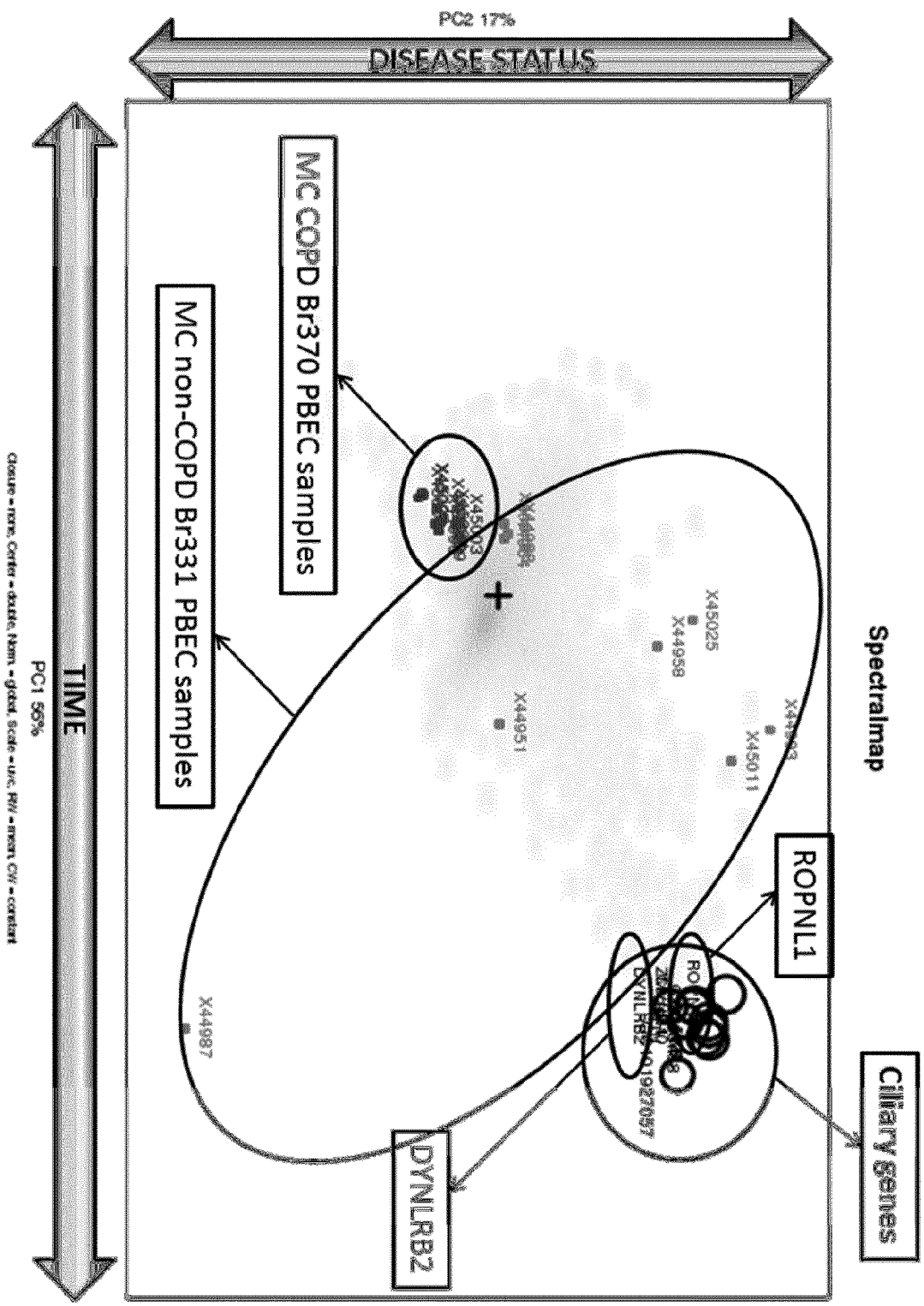

FIG. 8. Spectral map analysis with first principal component (PC1 on X-axis) and second principal component (PC2 on Y-axis).

Figure 9:
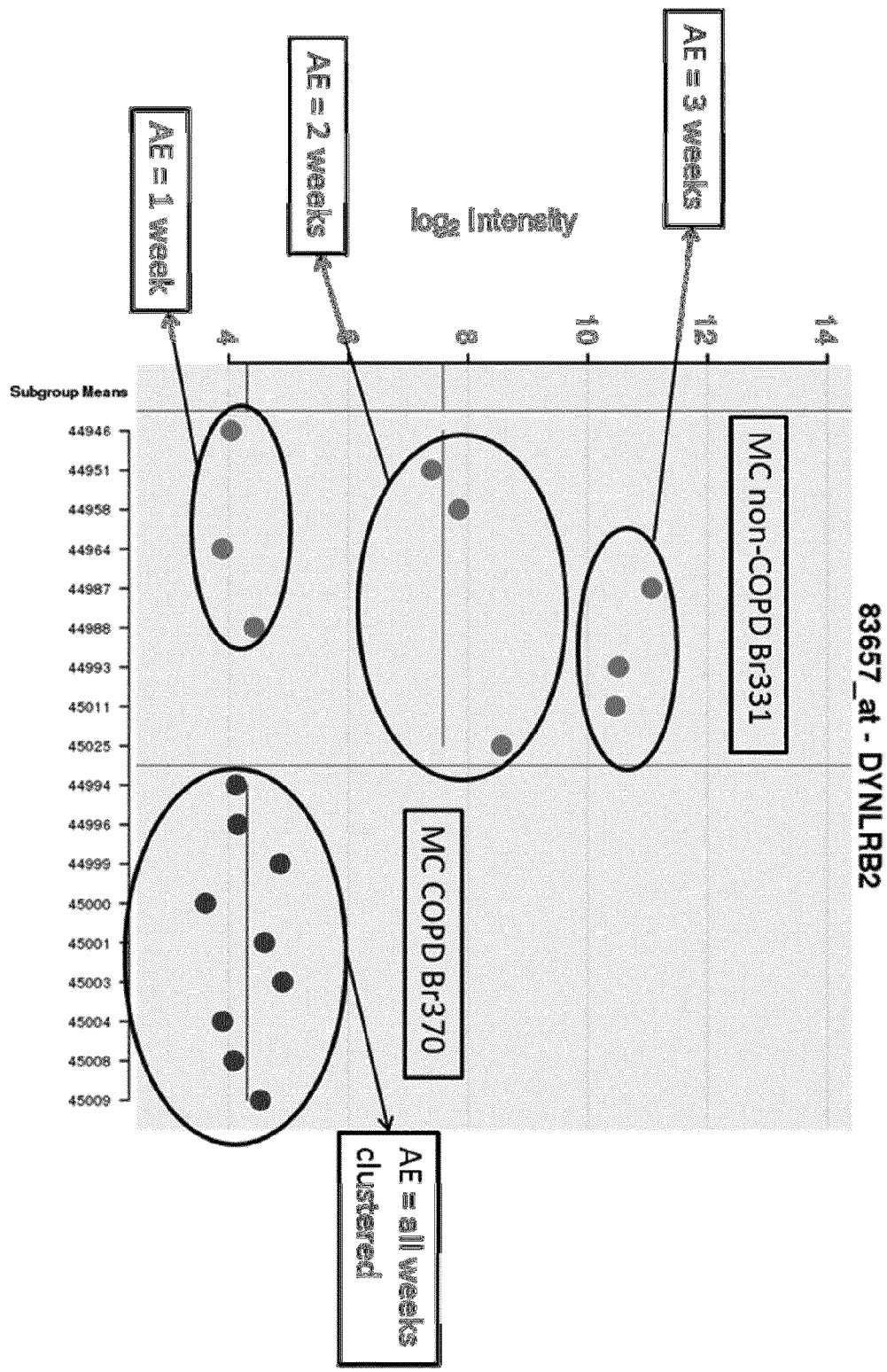

FIG. 9: DYNLRB2 gene expression profile, MC PBECs, non-COPD (Br331) versus COPD (Br370) donor.

Figure 10:
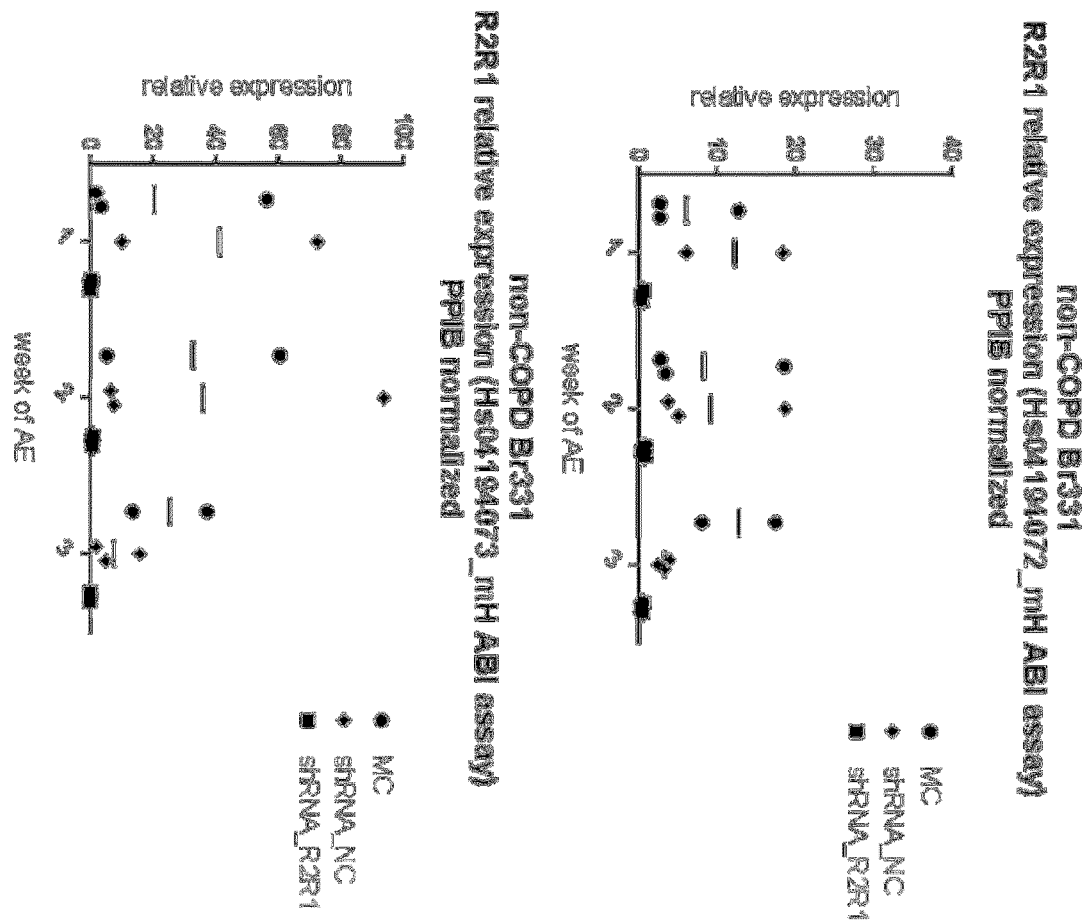
Figure 10:
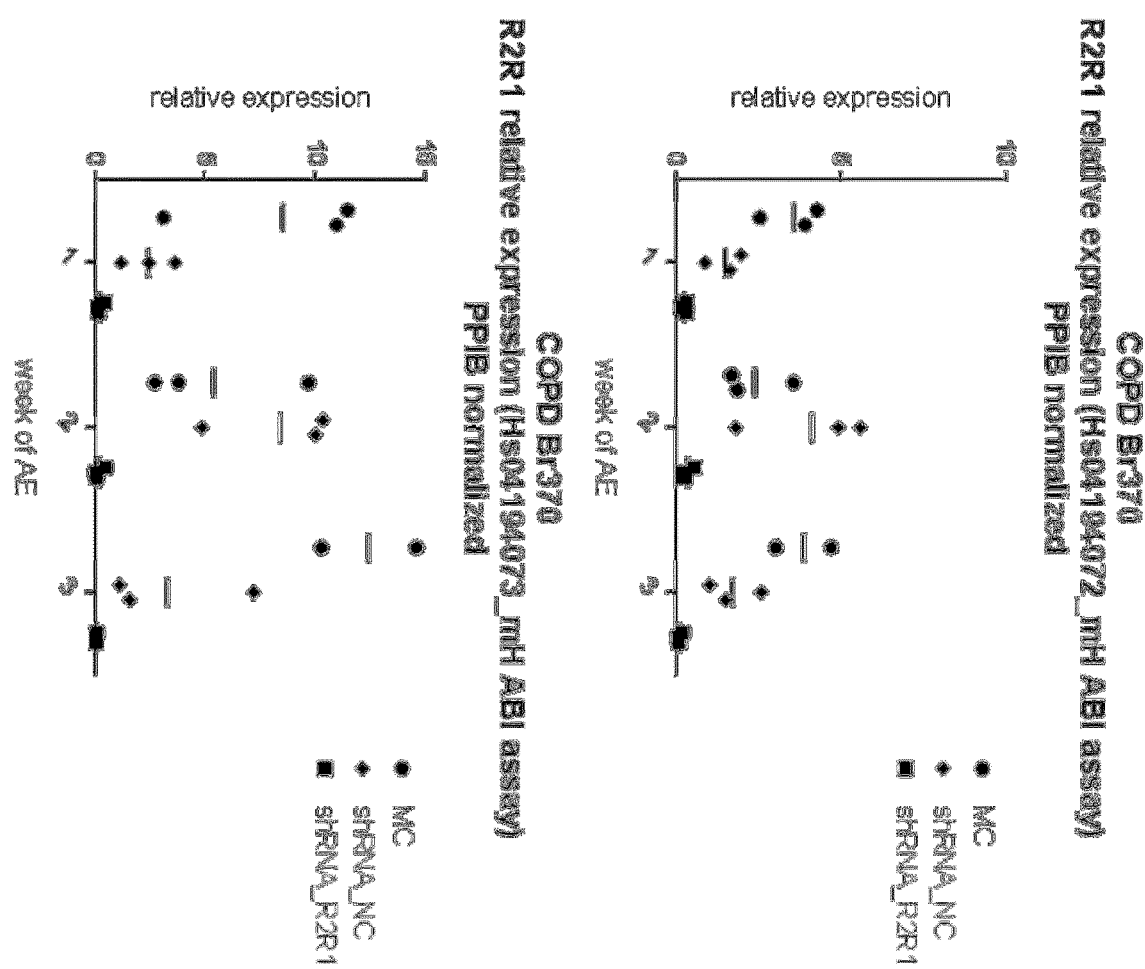

FIG. 10: RTqPCR of R2R1 gene expression (Assay ABI Hs04194072_mH and Assay ABI Hs04194073_mH) upon constitutive expression of shRNA_R2R1 in non-COPD Br331 PBECs and COPD Br370 PBECs.

Figure 11:
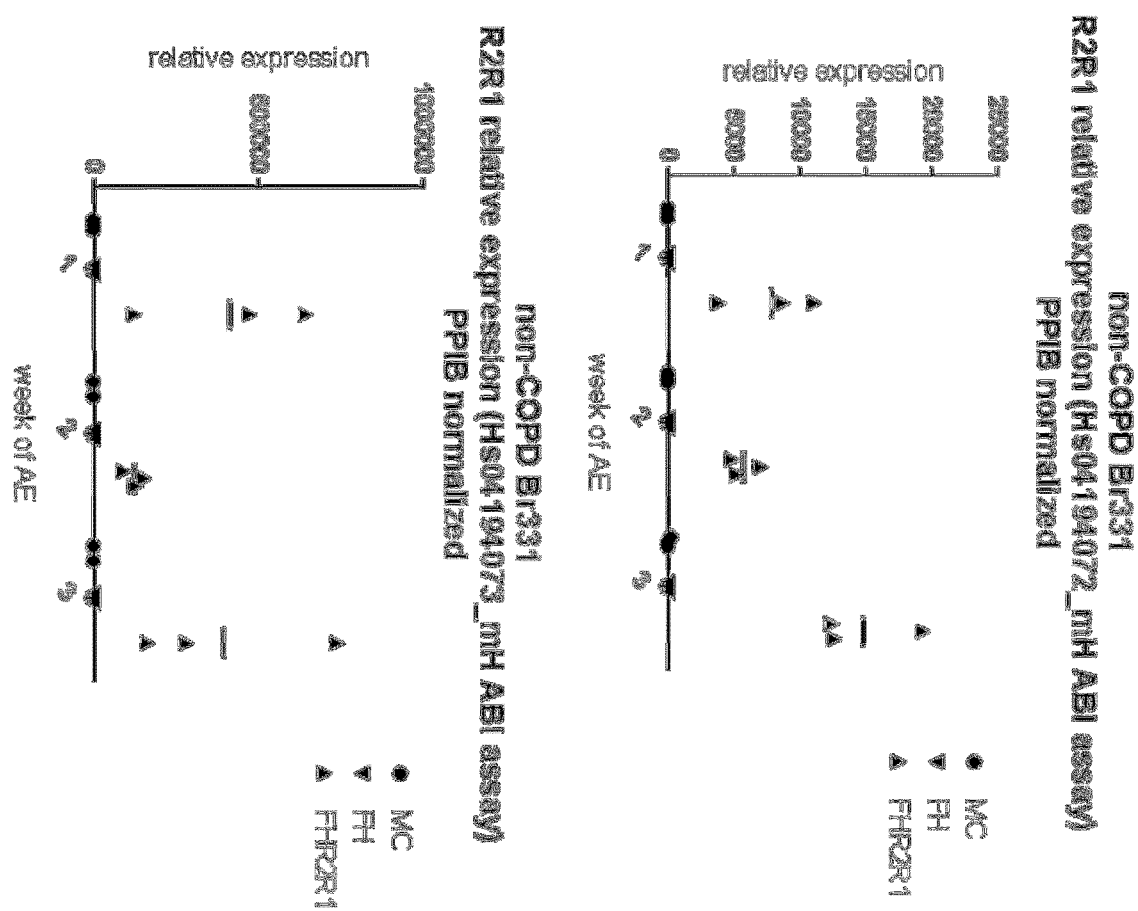
Figure 11:
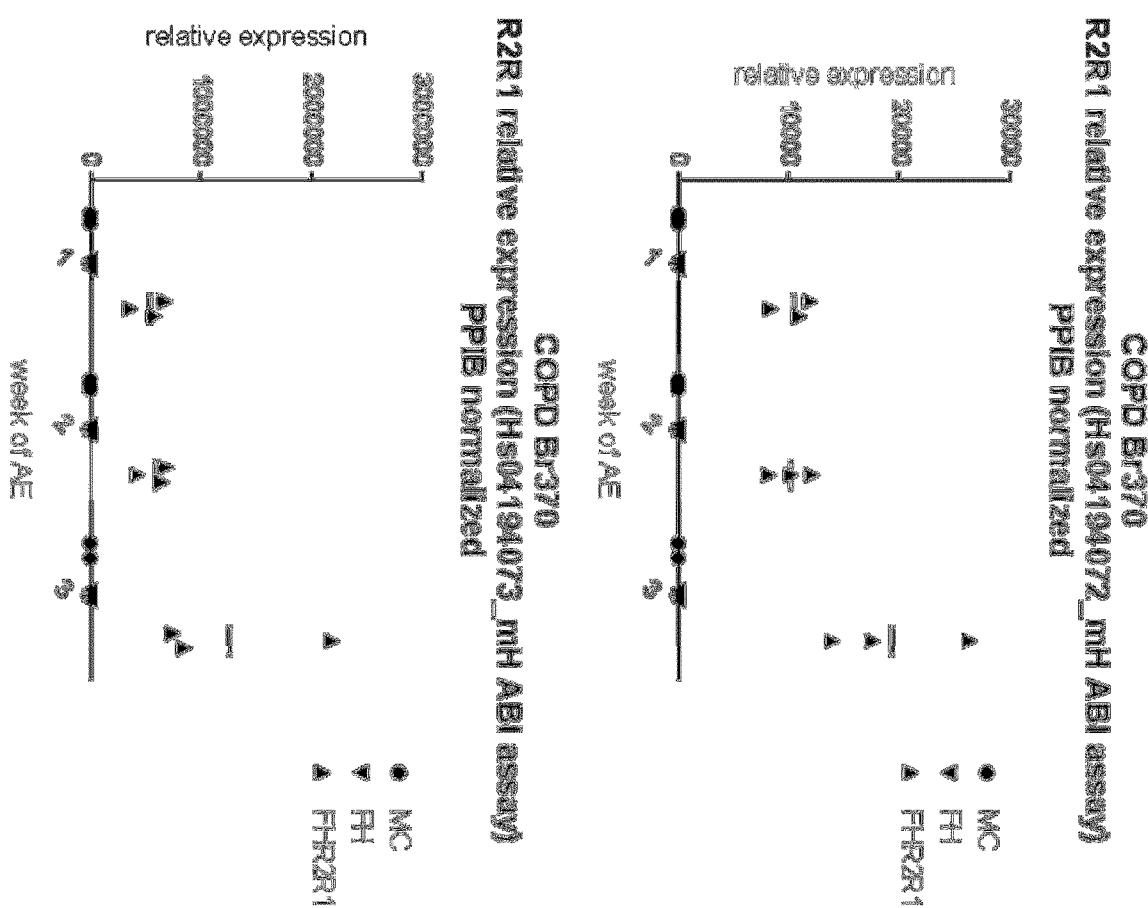

FIG. 11: RTqPCR of R2R1 gene expression (Assay ABI Hs04194072_mH and Assay ABI Hs04194073_mH) upon constitutive expression of FHR2R1 in non-COPD Br331 PBECs and COPD Br370 PBECs.

Figure 12:
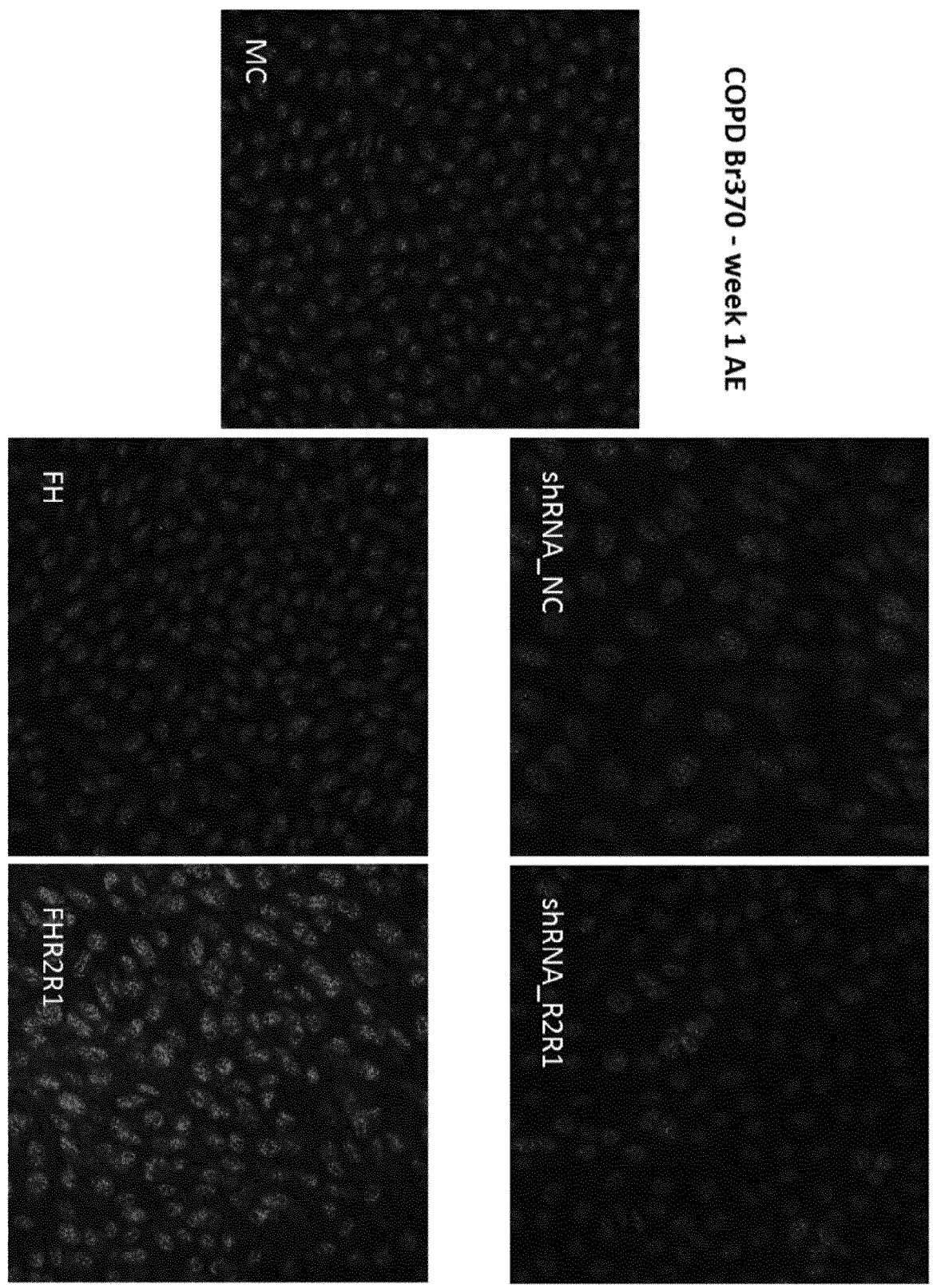

FIG. 12: Fluorescence pattern in COPD Br370 PBECs at week 1 of Air Exposure.

Figure 13:
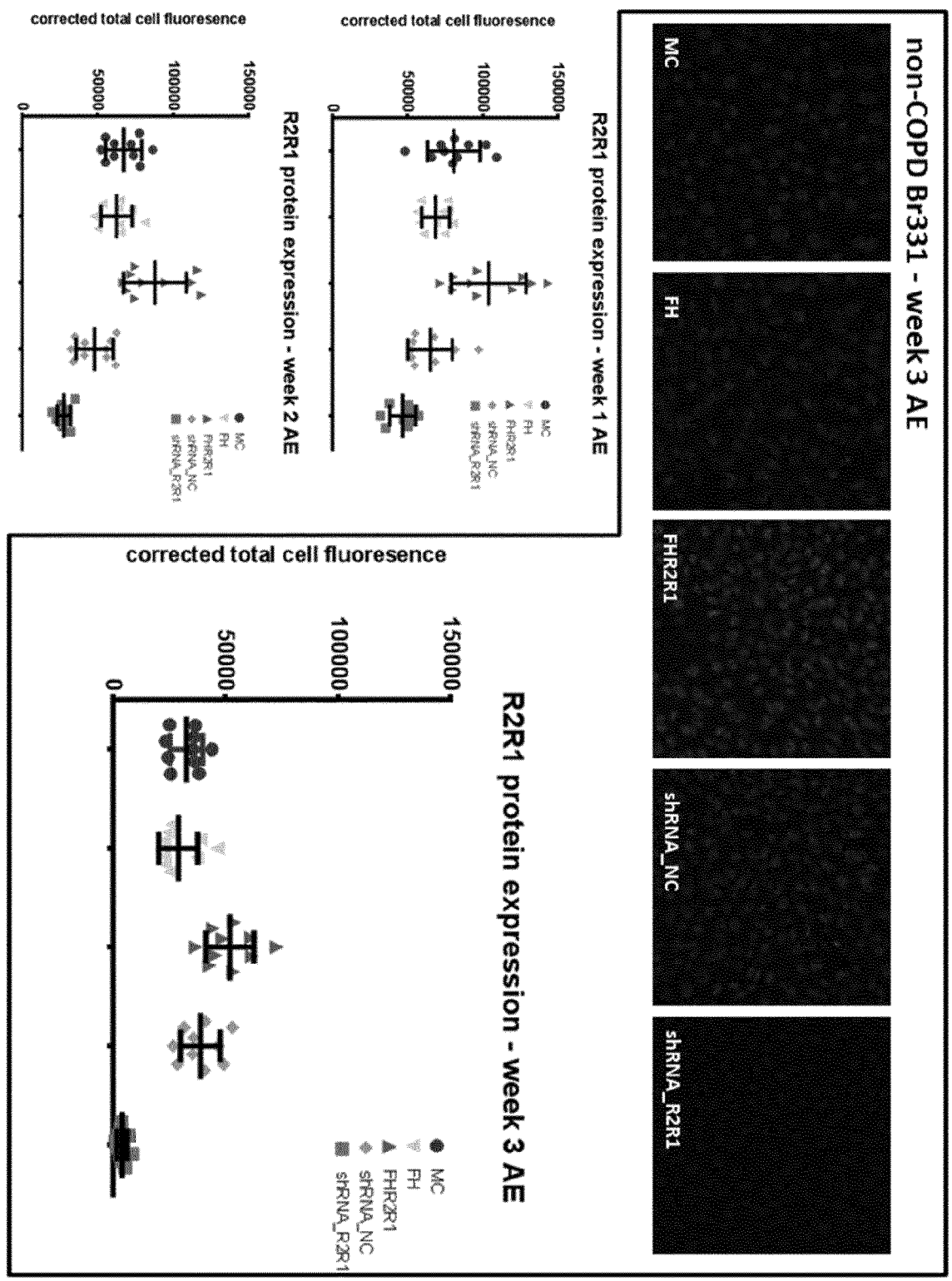

FIG. 13: Corrected Total Cell Fluorescence (CTCF) as a measure of R2R1 protein expression in non-COPD Br331 PBECs at week 1, 2 and 3 of Air Exposure.

Figure 14:
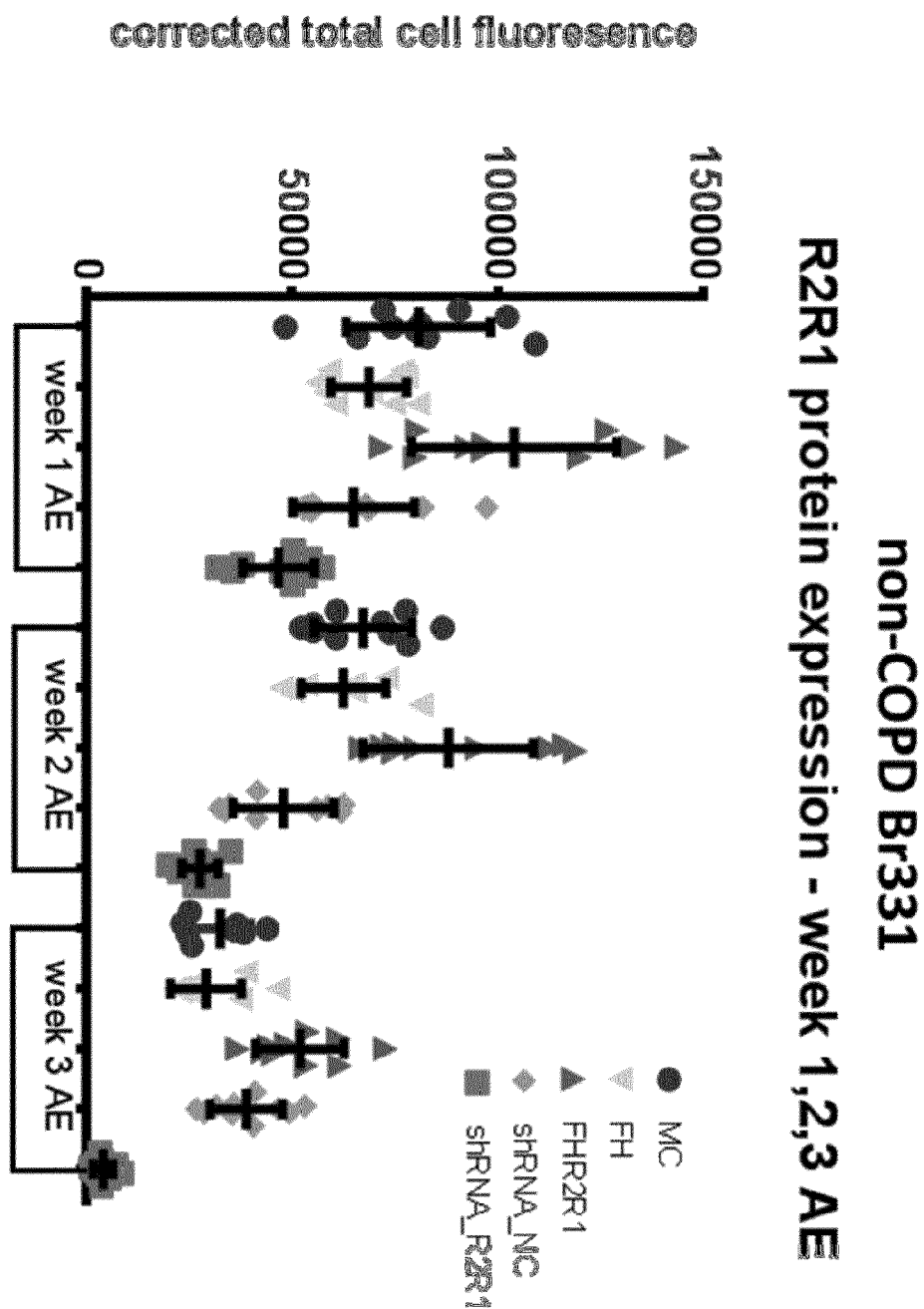

FIG. 14: Corrected Total Cell Fluorescence (CTCF) as a measure of R2R1 protein expression in non-COPD Br331 PBECs at week 1, 2 and 3 of Air Exposure summarized in one graph.

Figure 15:
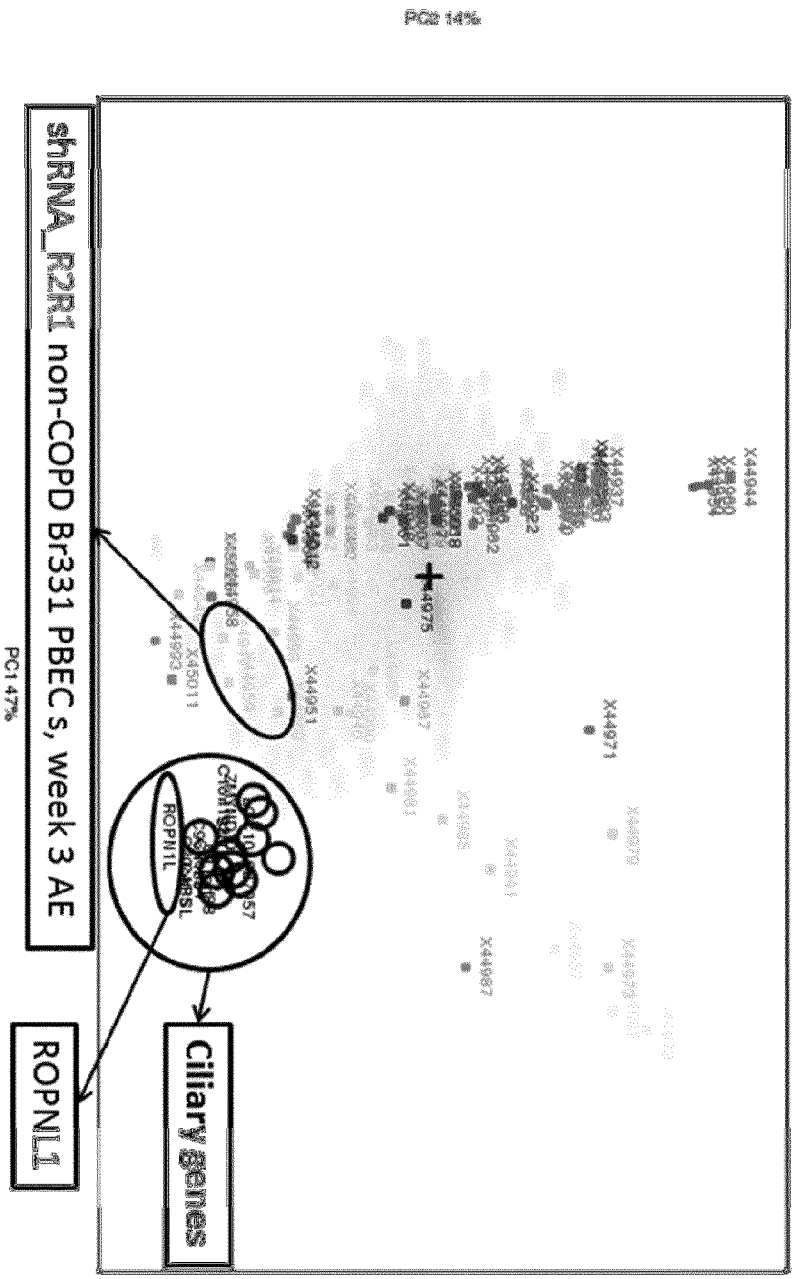

FIG. 15: SPM analysis of gene expression levels of all samples of the experiment.

Figure 16:
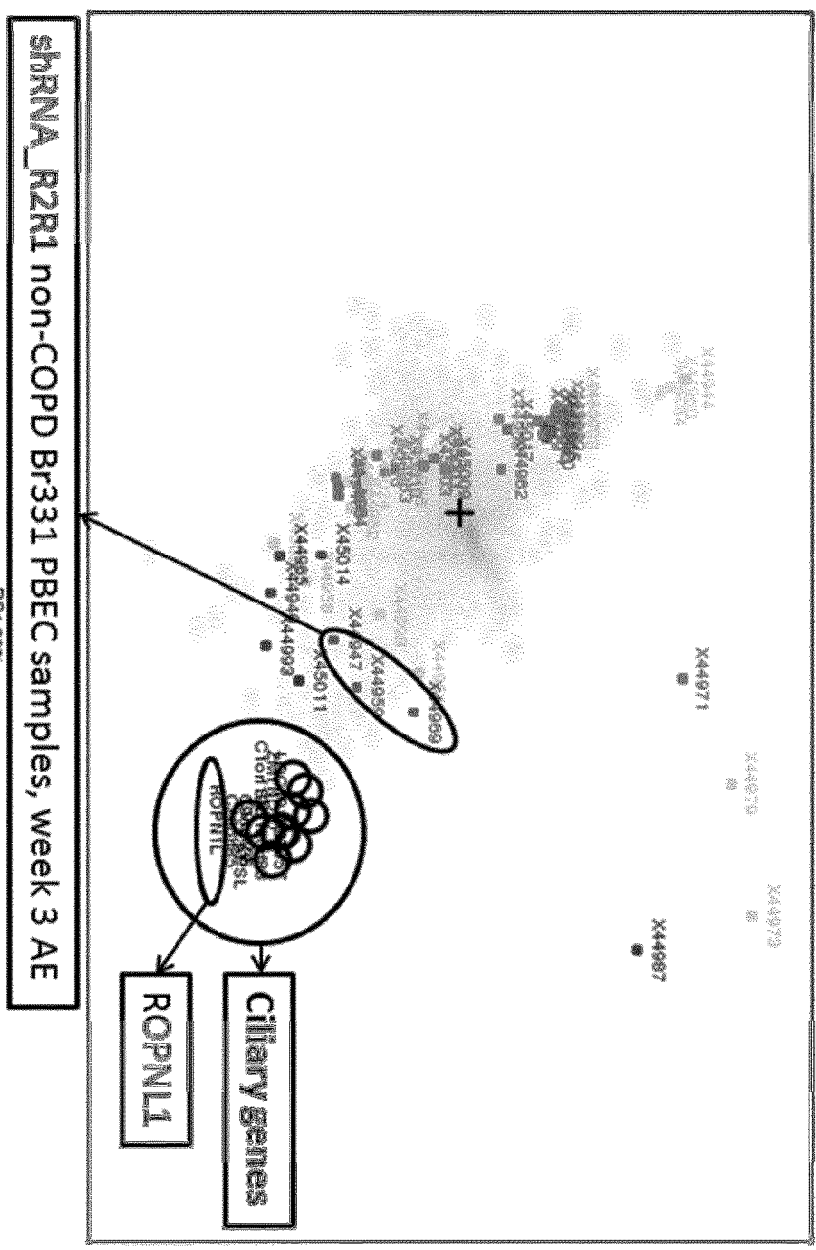

FIG. 16: SPM analysis of gene expression levels of the subset of R2R1 'downregulation' conditions.

Figure 17:
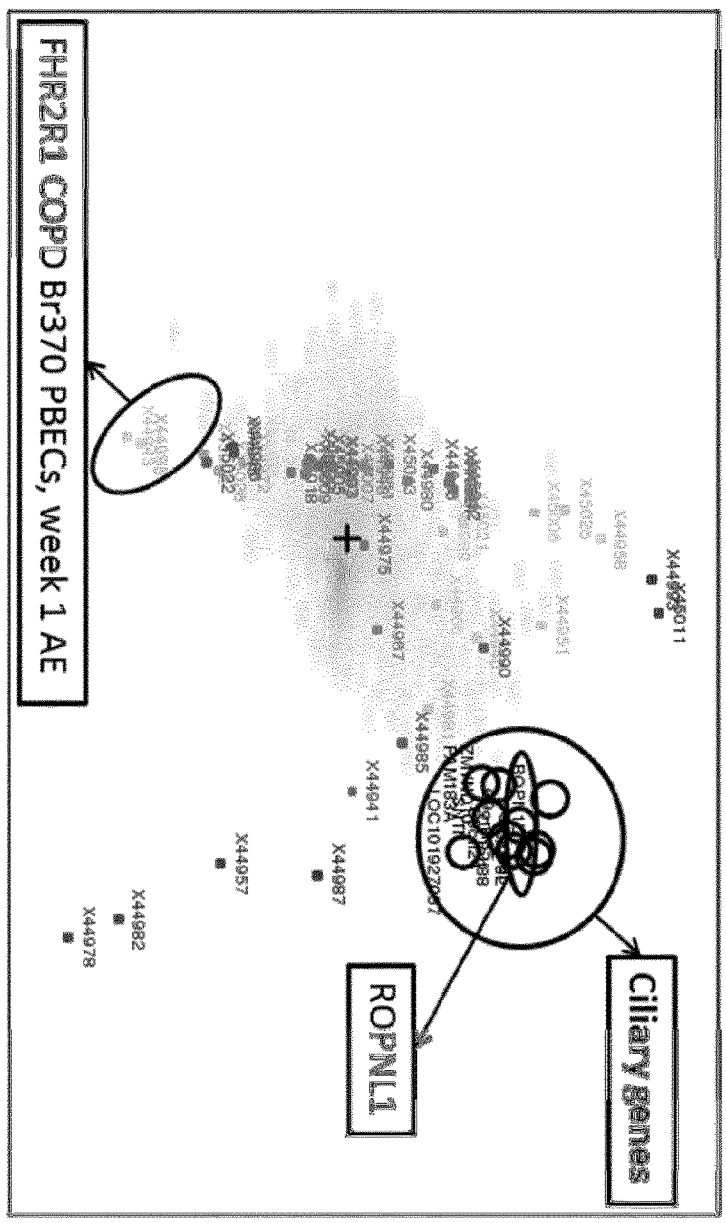

FIG. 17: SPM analysis of gene expression levels of the subset of R2R1 'upregulation' conditions.

Figure 18:
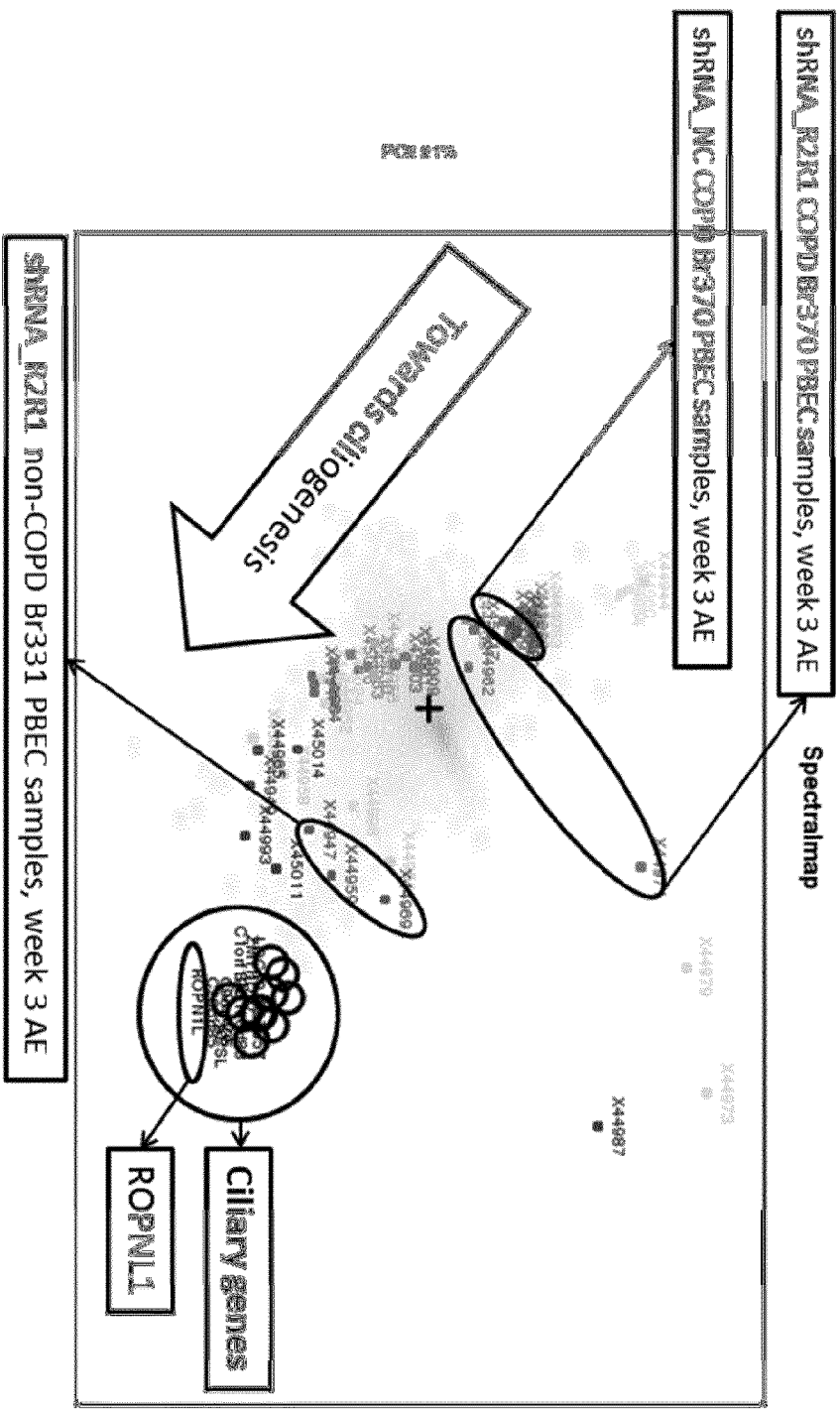

FIG. 18: SPM analysis of gene expression levels of all samples of the experiment.

Figure 19:
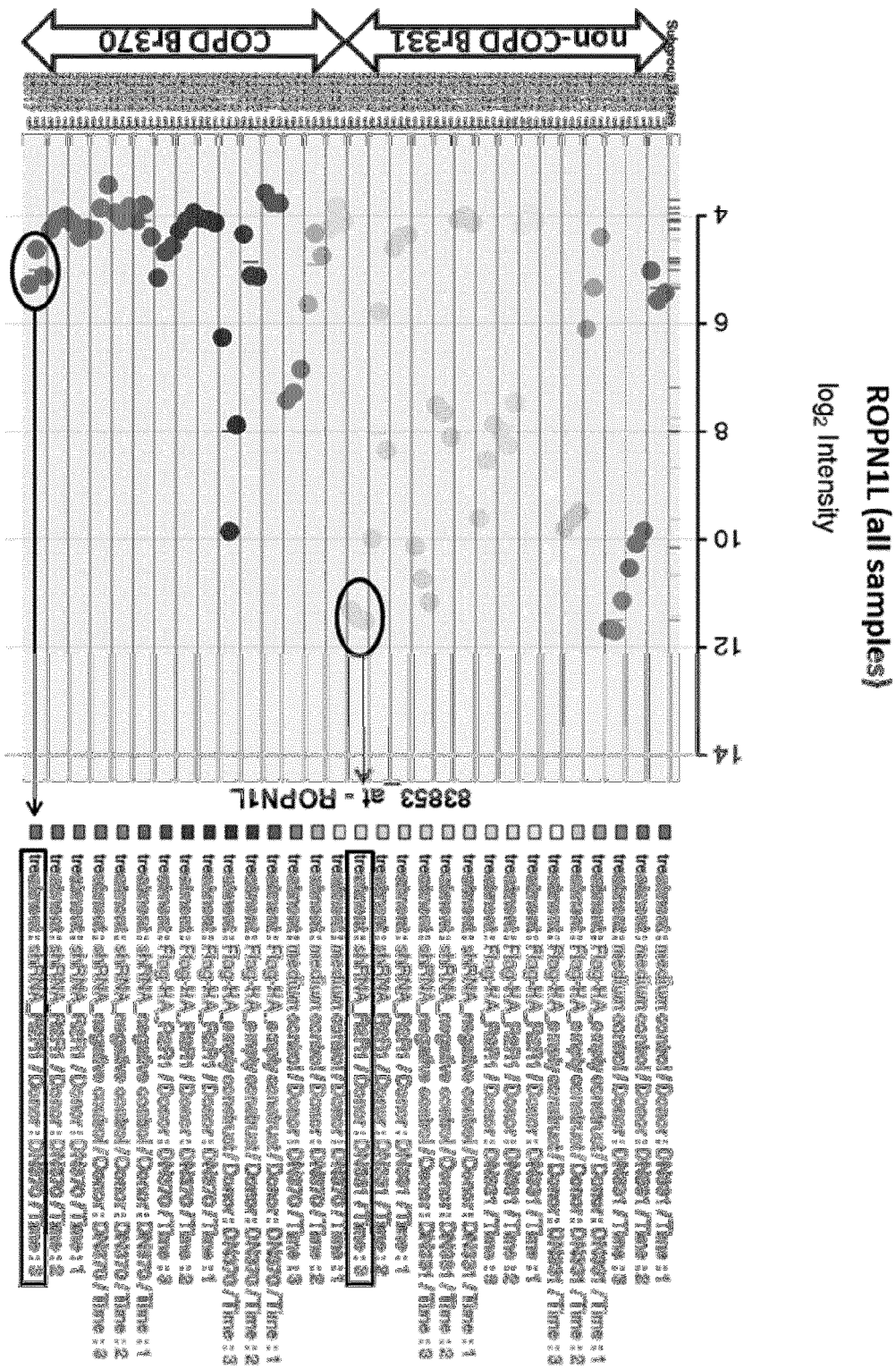

FIG. 19: $Log_2$ intensity plot illustrating upregulation of ROPN1L expression upon downregulation of R2R1 gene expression.

Figure 20:
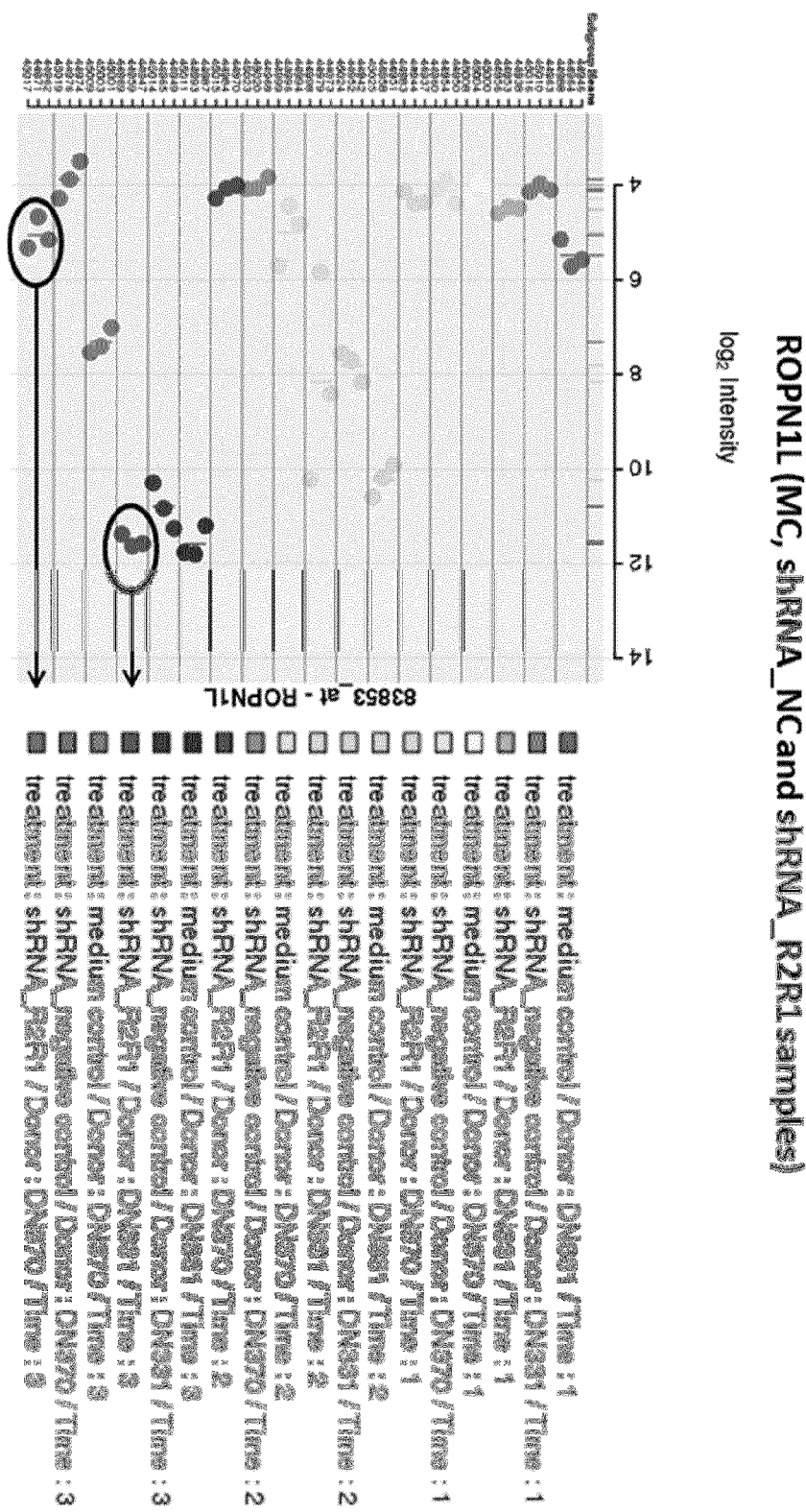

FIG. 20: $Log_2$ intensity plot illustrating upregulation of ROPN1L expression upon downregulation of R2R1 gene expression.

Figure 21:
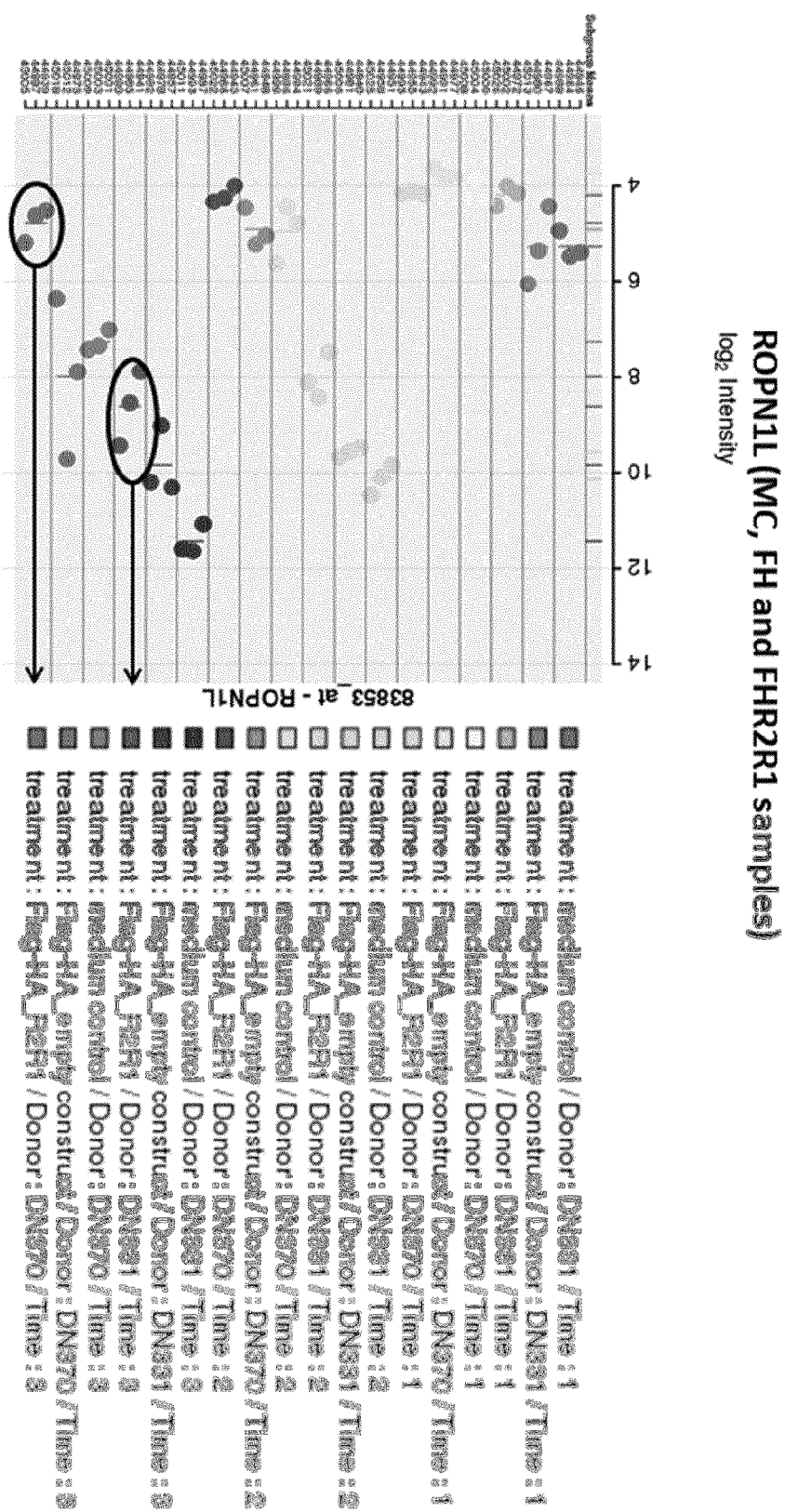

FIG. 21: $Log_2$ intensity plot illustrating downregulation of ROPN1L expression upon upregulation of R2R1 gene expression.

Figure 22:
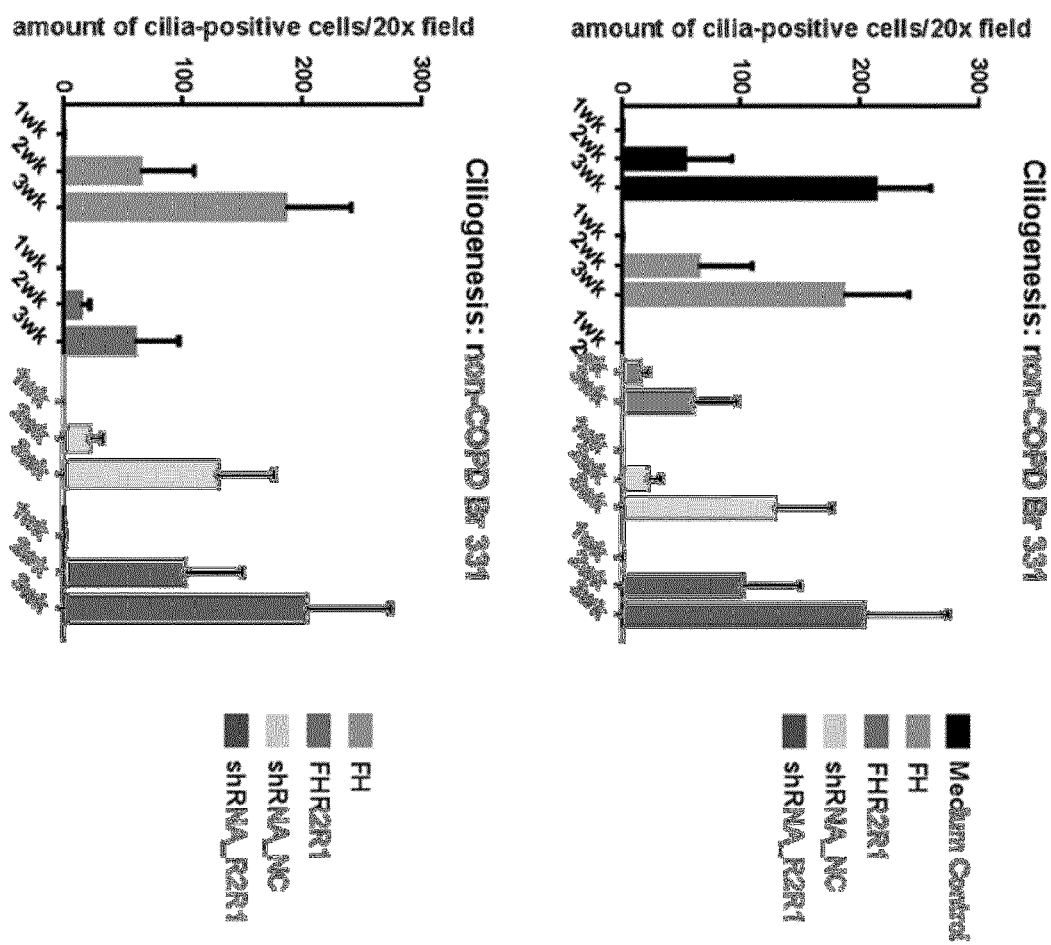

FIG. 22: number of ciliated cells non-COPD Br331.

Figure 23:
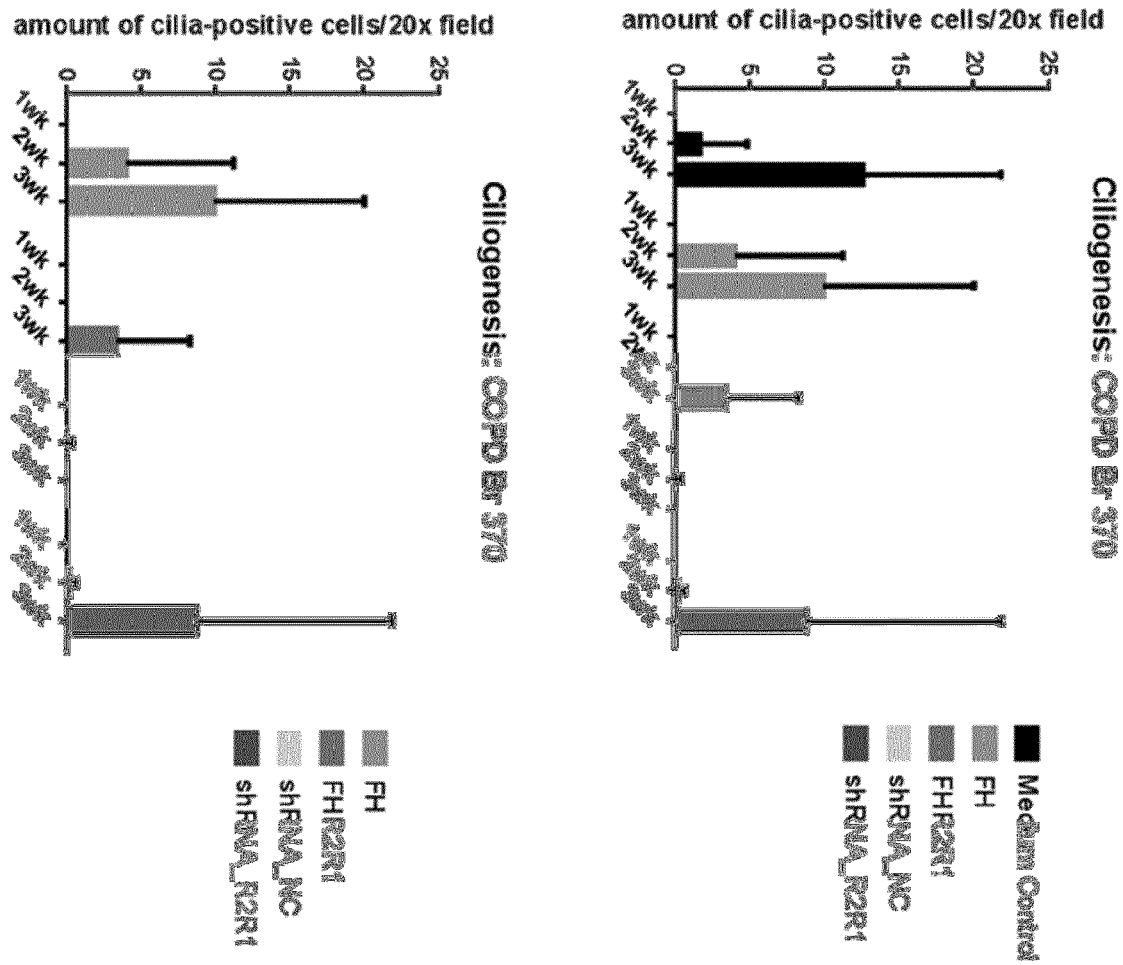

FIG. 23: number of ciliated cells COPD Br370.

Figure 24:
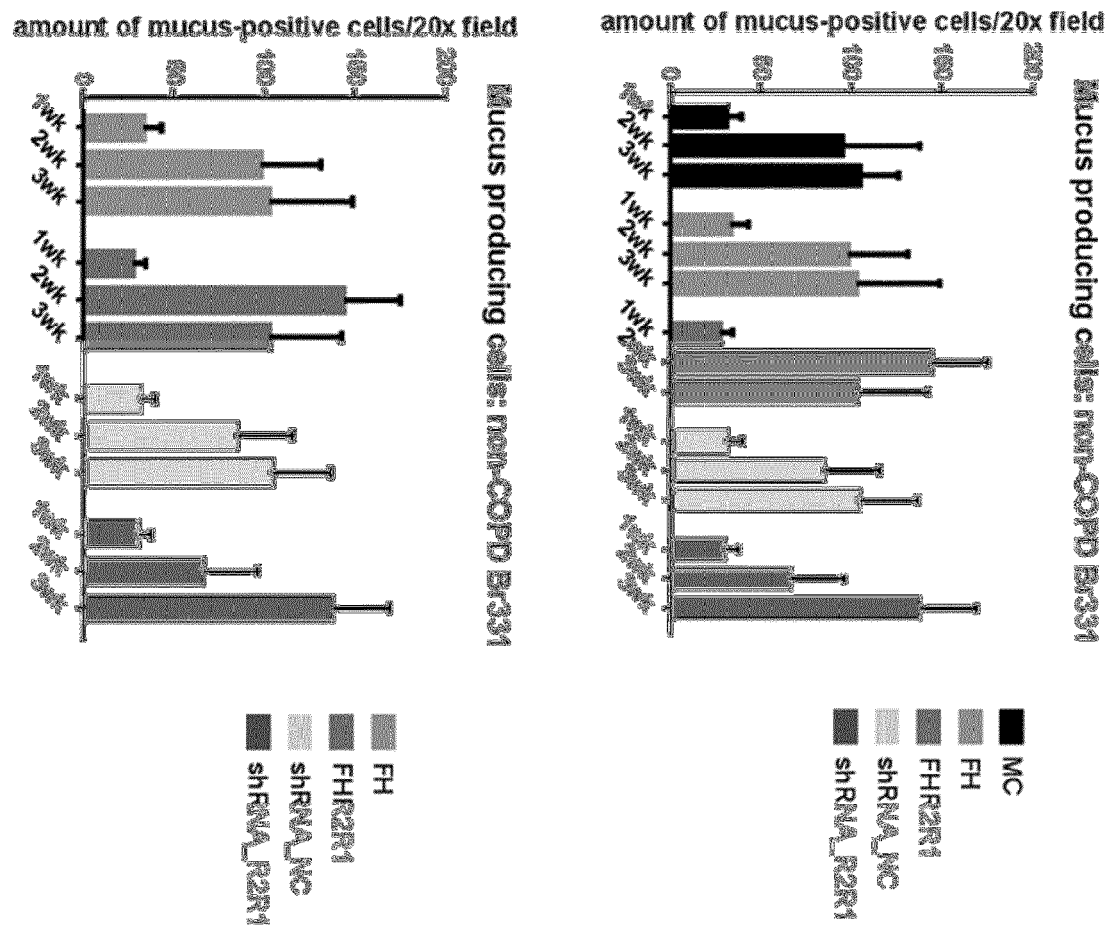

FIG. 24: number of mucus producing cells non-COPD Br331.

Figure 25:
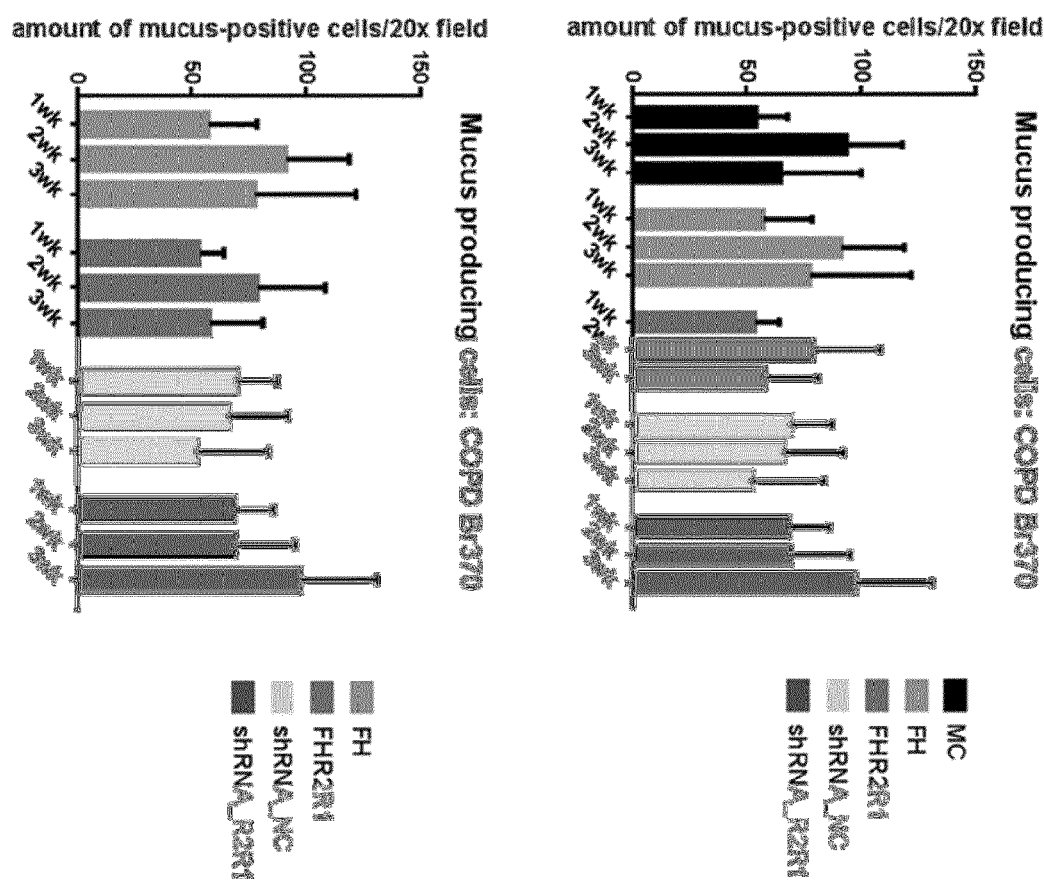

FIG. 25: number of mucus producing cells non-COPD Br331.

Figure 26:
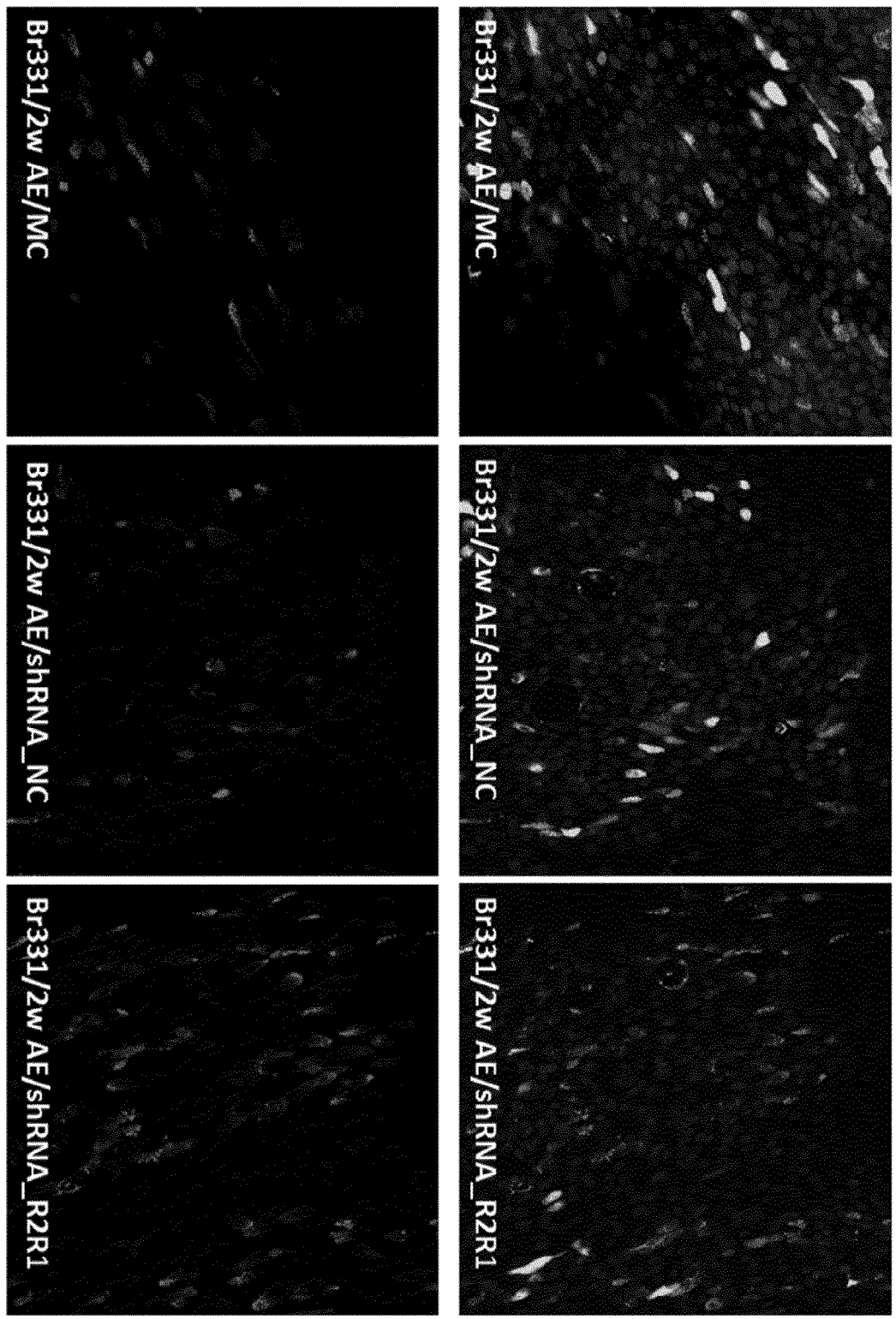

FIG. 26: illustration of staining of non-COPD Br331/2w AE/MC, shRNA_NC, shRNA_R2R1.

Figure 27:
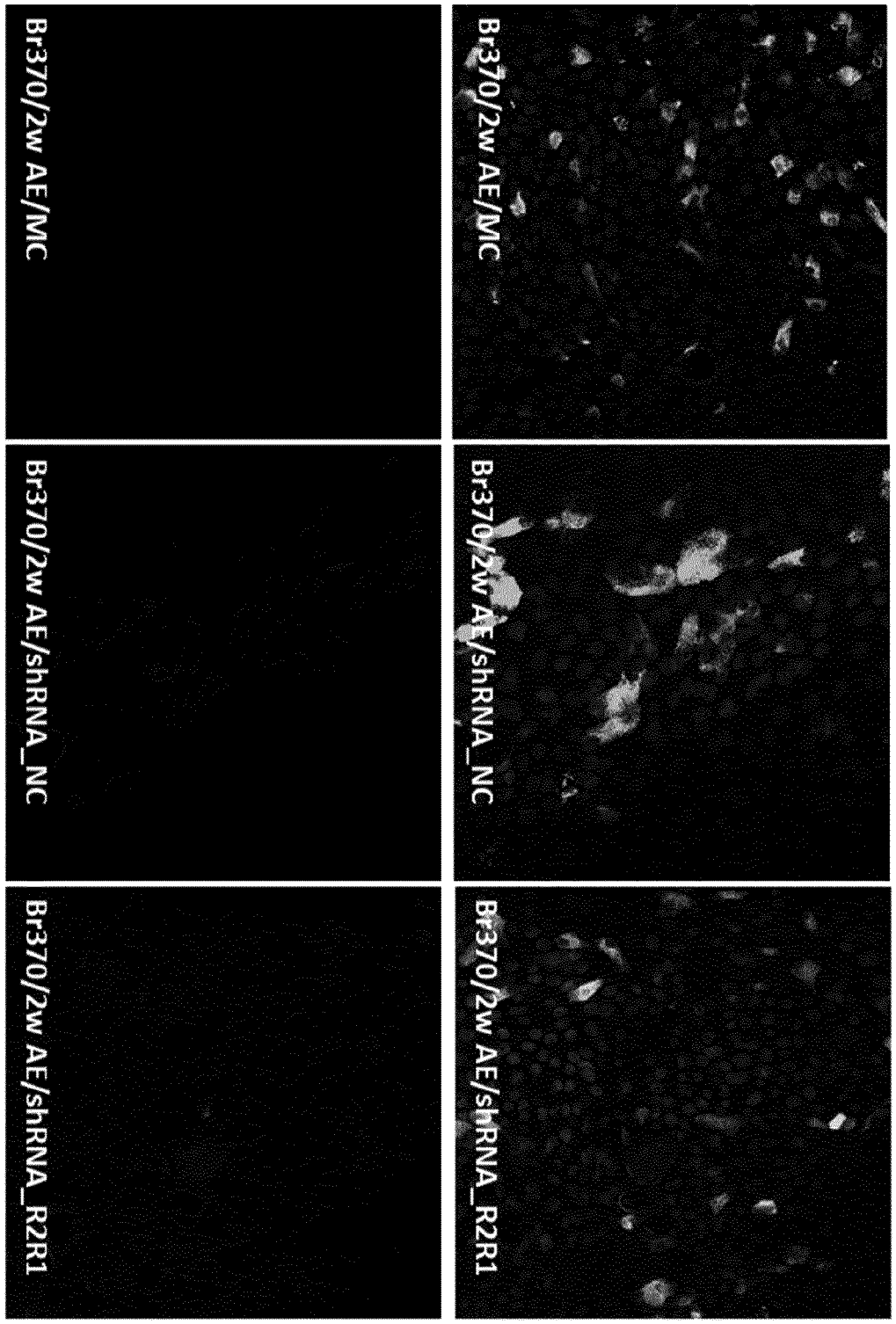

FIG. 27: illustration of staining of COPD Br370/2w AE/MC, shRNA_NC, shRNA_R2R1.

Figure 28:
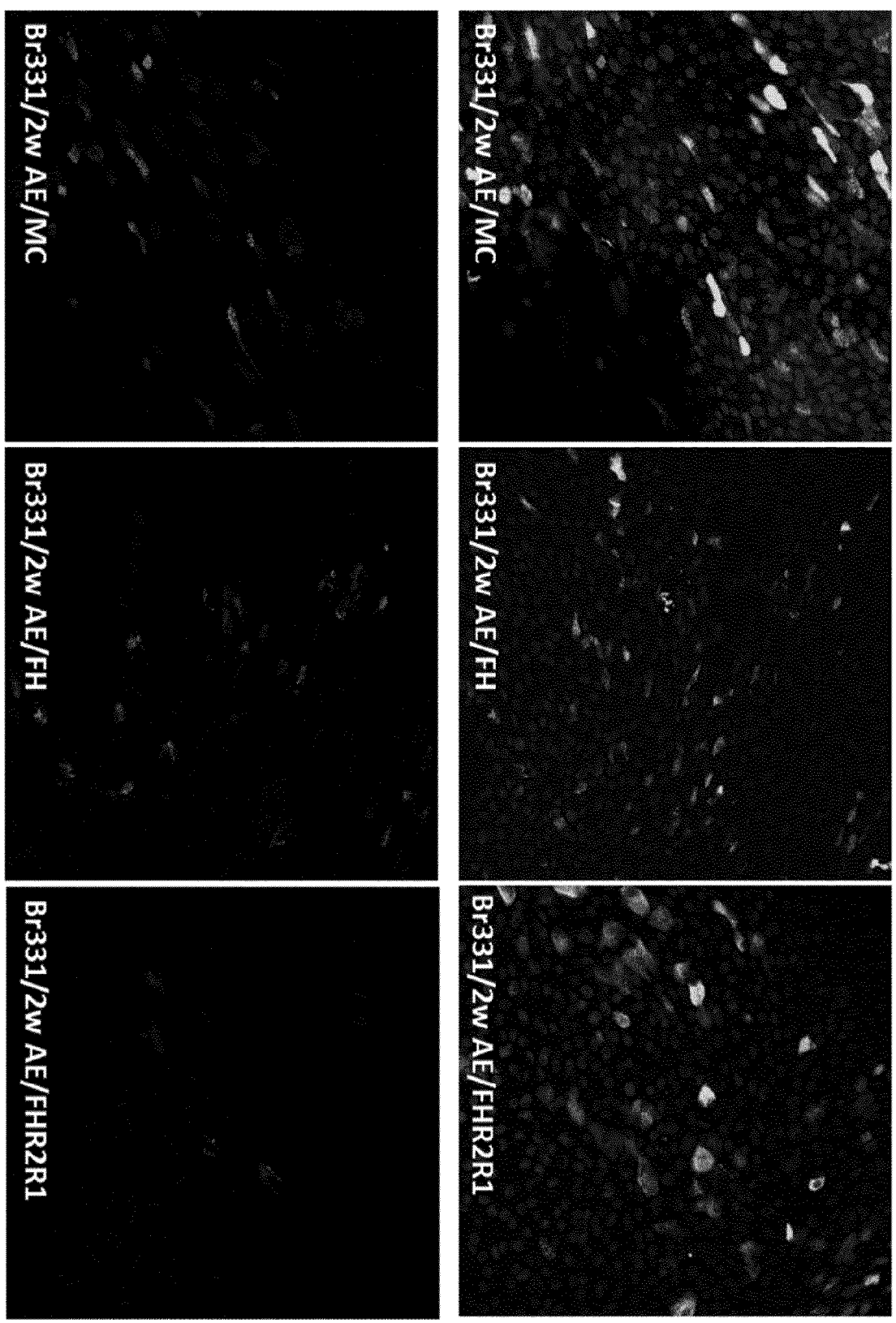

FIG. 28: illustration of staining of non-COPD Br331/2w AE/MC, FH, FHR2R1.

Figure 29:
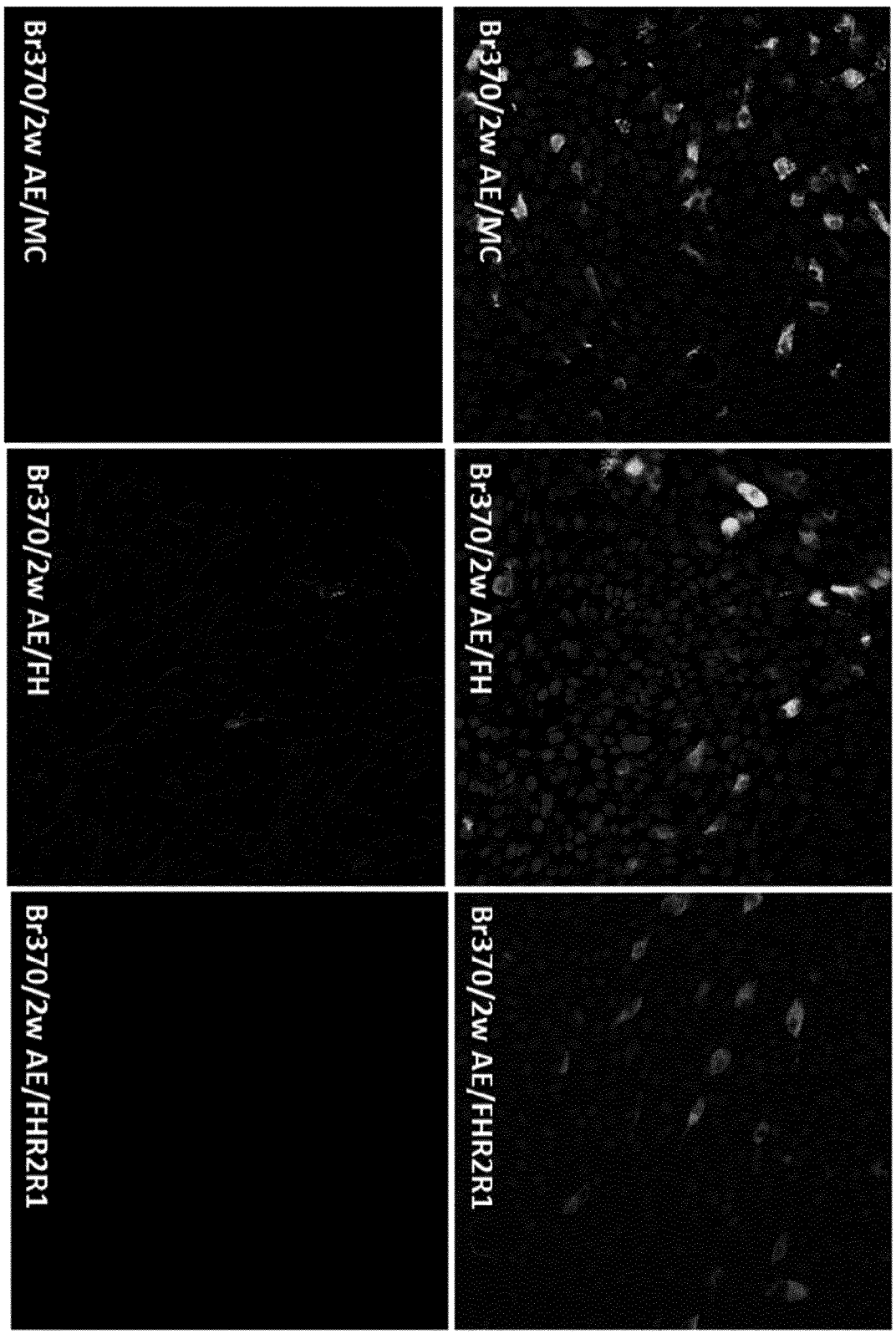

FIG. 29: illustration of staining of CORD Br370/2w AE/MC, FH, FHR2R1.

Figure 30:
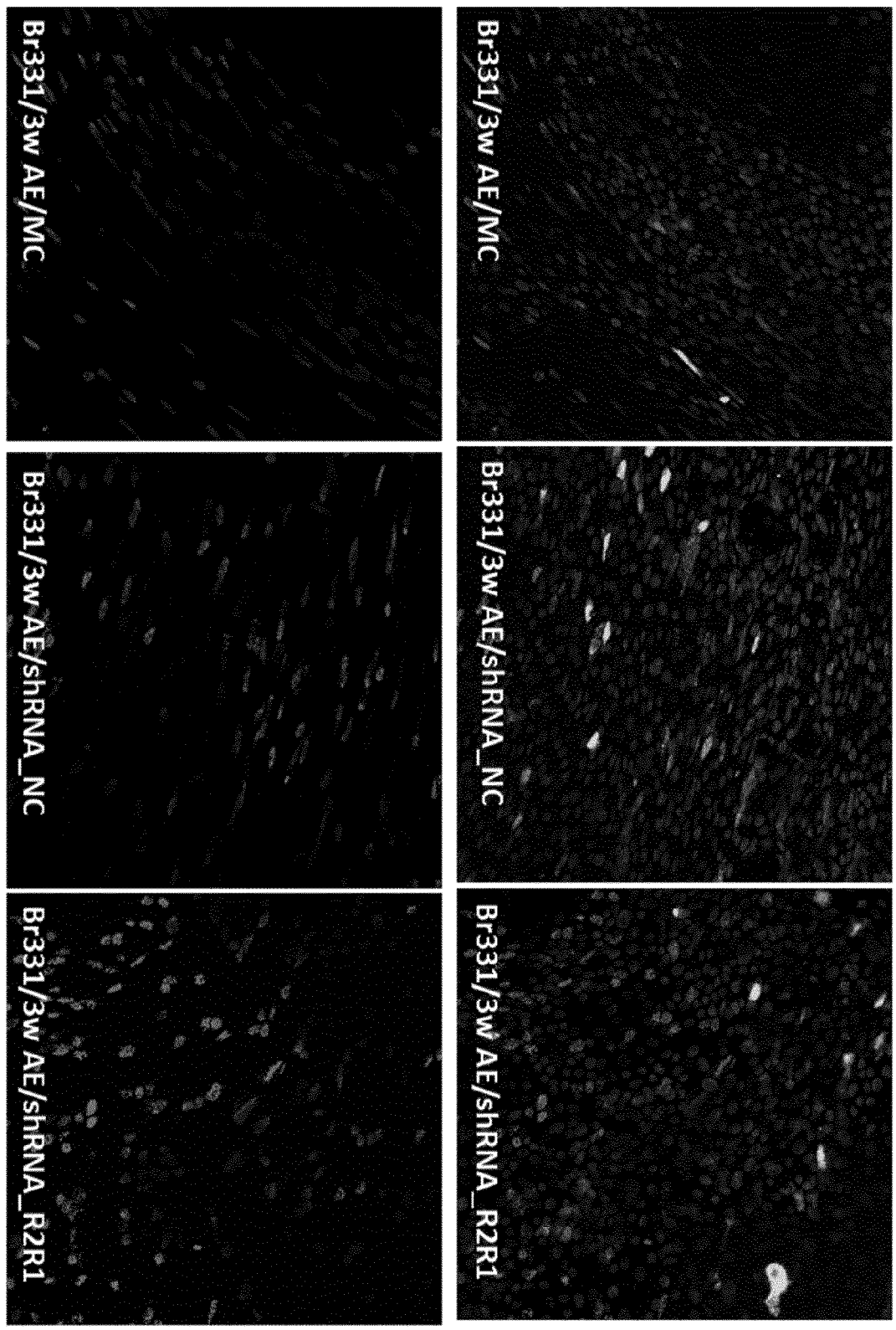

FIG. 30: illustration of staining of non-COPD Br331/3w AE/MC, shRNA_NC, shRNA_R2R1.

Figure 31:
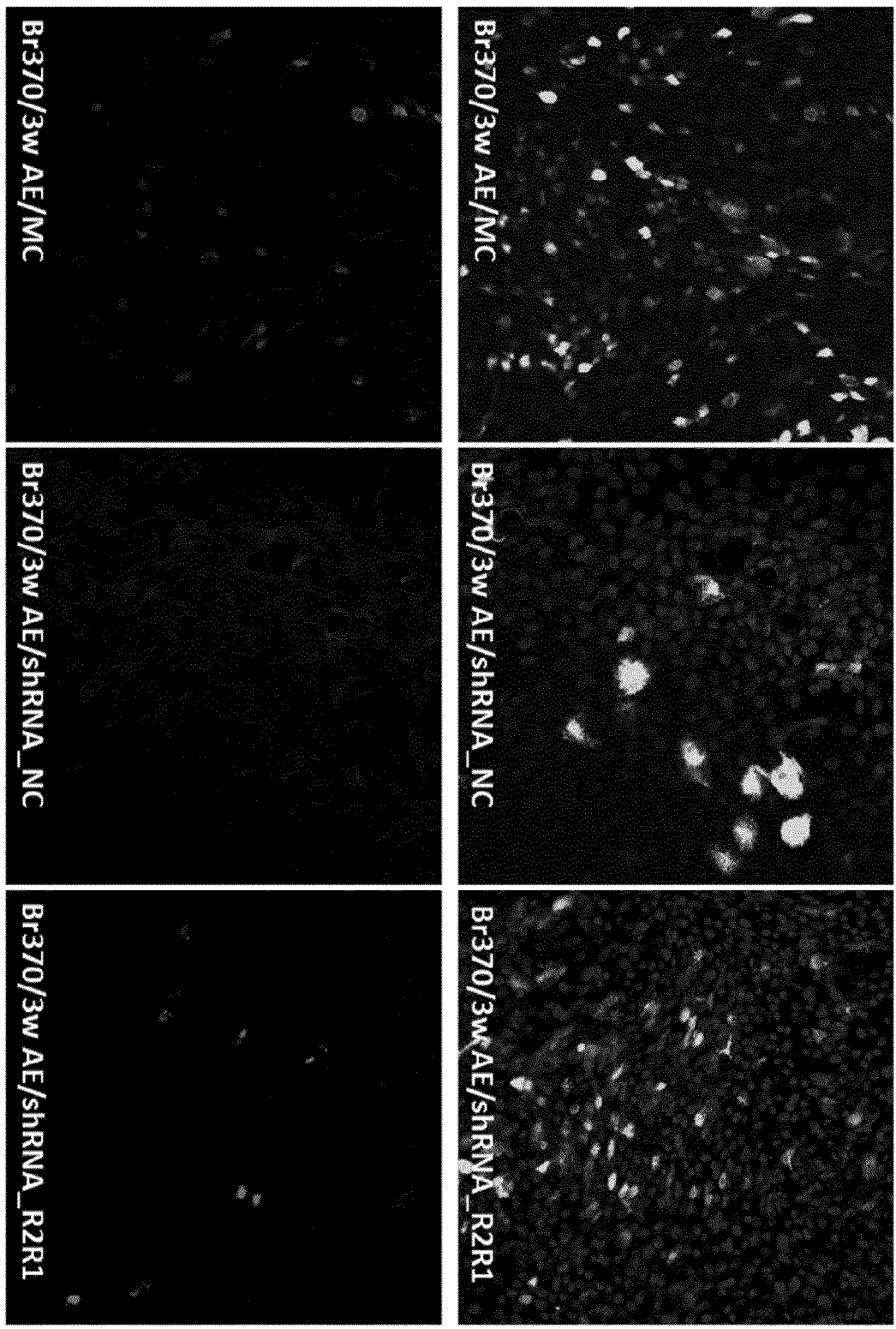

FIG. 31: illustration of staining of COPD Br370/3w AE/MC, shRNA_NC, shRNA_R2R1.

Figure 32:
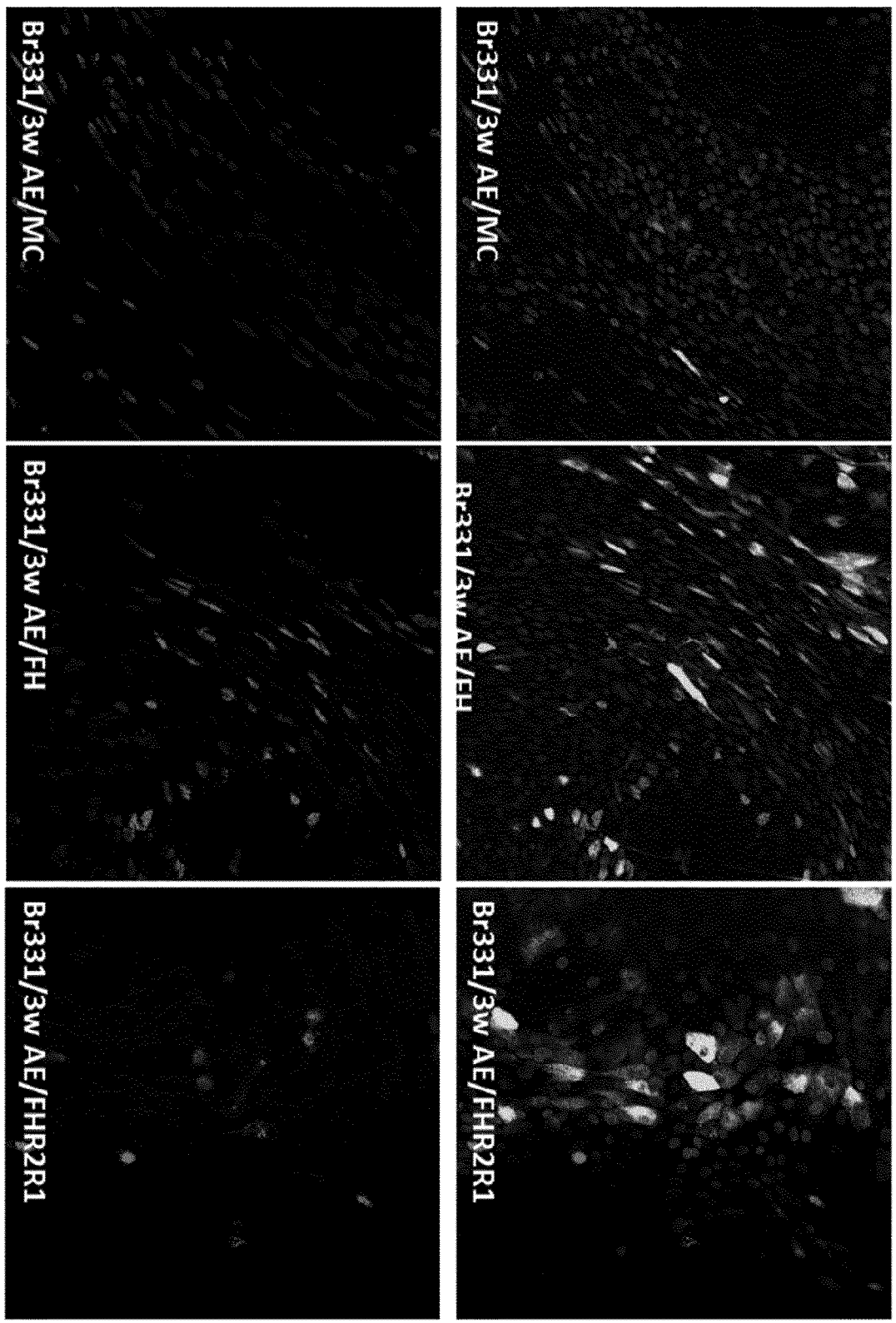

FIG. 32: illustration of staining of non-COPD Br331/3w AE/MC, FH, FHR2R1.

Figure 33:
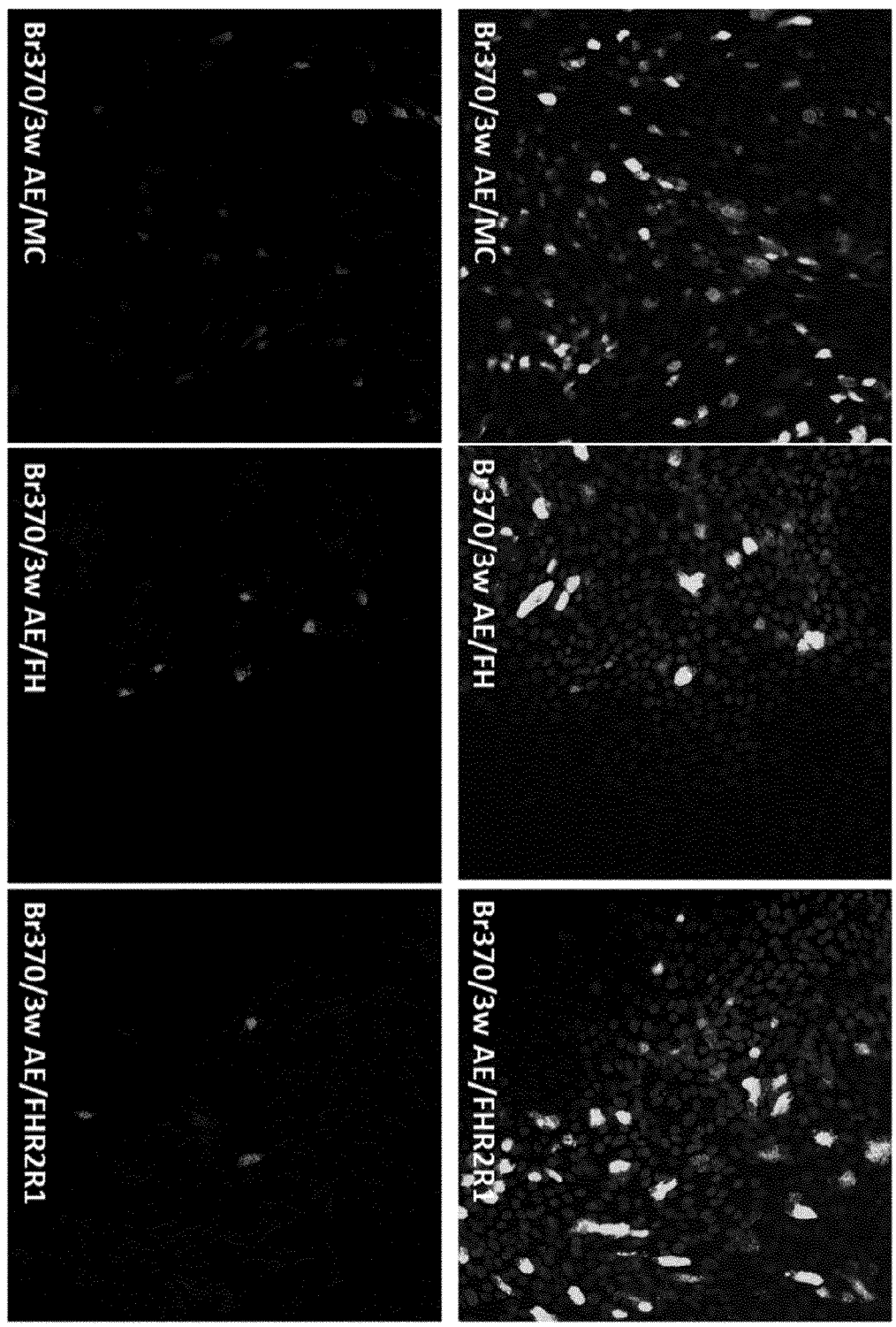

FIG. 33: illustration of staining of COPD Br370/3w AE/MC, FH, FHR2R1.

EXAMPLE 1

1.1: Binding of R2R1 Proteins (FAM25 Protein Family) to Polycomb Group PRC1 (Through Subunit RNF2) and Trithorax Group TrxG-MLL (Through Subunits DPY-30 and ASH2L) Chromatin Binding/Remodelling Complexes is an On/Off Switch for Ciliogenesis in the Human Pulmonary Bronchial Epithelium.

R2R1 is essential for maintenance and regeneration of the pulmonary epithelium, more particular the basal cell program. Experiments in submerged Primary Bronchial Epithelial Cells (PBECs) uncovered this function. The submerged culture conditions are characterized by rapid cell proliferation of undifferentiated PBECs. Hence, submerged culture conditions are ideal for the study of basal cells ('the stem cells of the human bronchial pulmonary ('airway') epithelium.

Follow-up experiments were performed in order to study the function of $R2R^1$ in differentiating/differentiated PBECs. PBECs were grown in Air Liquid Interface ('ALI') conditions. shRNA mediated knockdown of R2R1 gene expression in PBECs grown in ALI conditions revealed in two independent experiments the complementary function of $R2R^1$ in differentiation of human bronchial epithelial cells. The effect of constitutively and inducibly expressed shRNA 'FAM25 147' (=TRCN0000284147, also referred to as shRNA_R2R1) directed against R2R1 expression is demonstrated in FIGS. 4-7.

1.2: Knockdown of the Expression of R2R1 Leads to Profound Upregulation of the Ciliogenesis or Ciliary Gene Expression Program.

The ciliary gene expression program encompasses the structural and motor/movement proteins of the motile cilium. It follows that R2R1 controls the gateway between basal cell and ciliated cell. The function of R2R1 is 'symmetric': specifically, in the presence $R2R^1$ the basal cell program is executed, in absence of R2R1 the ciliated cell program is initiated. The symmetry is basal cell↔ciliated cell (see FIG. 1). It should be noted that there is no evidence for a symmetry basal cell↔mucous producing cell, a finding with important therapeutic consequences.

Loss of ciliated cells leads to inefficient mucociliary clearance in patients suffering from COPD. This is in fact the pathological hallmark of COPD: the abnormal bronchial epithelium (loss of ciliated cells, squamous differentiation and basal cell hyperplasia) is unable to clear the airways of mucus, bacteria, viruses and debris. This ineffective clearance mechanism will cause severe symptoms (coughing, bronchopulmonary infections, inefficient gas exchange in the lung . . . ), resulting in a high mortality rate.

PBECs grown in ALI conditions were found to exhibit a persisting downregulation of the ciliary gene expression program. This phenomenon was observed in PBECs from multiple donors in two independent experiments.

A comparison was made between the transcriptional effect of COPD disease status and shRNA mediated knockdown of R2R1 in PBECs (ALI culture conditions), see FIG. 3. The left upper quadrant highlights the effect of R2R1 on ciliogenesis and COPD). Genes that are differentially expressed because of shRNA mediated knockdown of R2R1 in PBECs (ALI conditions) are displayed along the Y-axis. Genes that are upregulated because of R2R1 knockdown will appear above the zero on the Y-axis. Genes that are differentially expressed (COPD versus non-COPD status) are displayed along the X-axis. Genes that are downregulated because of COPD disease status will appear on the left of the zero on the X-axis. The left upper quadrant will represent now the intersection between genes that are upregulated because of R2R1 knockdown and genes that are downregulated because of COPD. The majority of this gene set is involved in ciliogenesis.

1.3: Investigating the Mechanism of Action by which R2R1 Exerts this Gateway Function (Basal Cell⇔Ciliated Cell).

Ciliogenesis requires the production of many ciliary proteins. The simultaneous expression of these multiple genes has to be tightly regulated. Consequently, this regulation has to act as an on/off switch.

We identified RNF2, the core component of the PRC1 complex, as a R2R1 binding partner in two independent yeast two hybrid (Y2H) experiment (first experiment: 7 hits, 4 being RNF2—second experiment 4 hits, 1 being RNF2). DPY-30, a constituent of the TrxG-MLL complex, was identified as another binding partner (⅐ hits, in the first Y2H experiment). Finally, SF3B2 (¼ hits in the second Y2H experiment) completes the set of chromatin binding partners.

The interaction between R2R1 and PRC1/TrxG proteins was confirmed in an in vitro Translation System (1-Step CHO High-Yield IVT Kit, Thermo Scientific). An N-terminal HA-tagged R2R1 construct (in pT7CFE1 vector) was co-expressed with different permutations of N-terminal FLAG-tagged PcG and TrxG constructs (in pT7CFE1 vector). Co-immunoprecipitation was performed with EZview™ Red Anti-HA Affinity Gel (Sigma Aldrich) in order to bind R2R1 and any associated proteins in the reaction mixture. The bound proteins were analyzed by SDS-PAGE and western-blotted with Monoclonal ANTI-FLAG® M2 antibody (Sigma Aldrich).

The different permutations are described in the table below (N-term=N-terminal):

| 1 |
|---|
| Magic Mark Protein Standard |

| 2 |
|---|
| N-term DPY-30 |
| N-term R2R1 |

| 3 |
|---|
| N-term DPY-30 |
| N-term ASH2L |
| N-term KMT2D |
| N-term R2R1 |

| 4 |
|---|
| N-term RNF2 |
| N-term RYBP |
| N-term KMT2D |
| N-term R2R1 |

| 5 |
|---|
| N-term RNF2 |
| N-term PCGF4 (BMI1) |
| N-term RYBP |
| N-term R2R1 |

FIG. 2 demonstrates the co-immunoprecipitation of R2R1 and different PRC1/TrxG proteins using different permutations. RNF2 binds R2R1 more strongly in a non-canonical permutation of the PRC1 complex (in the presence of KMT2D (MLL4) and RYBP, lane 4) in comparison with a canonical form of the PRC1 complex (lane 5). ASH2L is a clear binding partner of R2R1 (lane 3) in a permutation containing the TrxG-MLL proteins KMT2D (MLL4), DPY-30 and ASH2L. ASH2L and DPY-30 are known reciprocal binding partners and essential subunits of TrxG-MLL complexes. Finally, putative heterodimerization between R2R1 and DPY-30 is demonstrated in the permutation of the protein mixture containing only R2R1 and DPY-30.

It follows that the transcriptional effect (many genes are controlled by $R2R^1$ at the same time) is caused by changing the binding properties of chromatin remodelers, PRC1 being the most striking complex. PRC1 is known to interchange its components resulting in canonical and non-canonical complexes. The effect of PRC1 on chromatin (H2A ubiquitylation, recruiting PRC2 and aiding PRC2 in its repressive function) is determined by its different component proteins. However, RNF2 is always present in the PRC1 complex.

Hence we've found a well-defined non-canonical function of PRC1. This function is determined by the binding of $R2R^1$ to the PRC1 complex. R2R1 binding to PRC1 is a gateway to ciliogenesis. Furthermore, R2R1 interacts with the chromatin-modifying TrxG-MLL complex (Trithorax group or TrxG) through DPY-30 and ASH2L. In contrast to PRC1, TrxG maintains active gene expression by H3K4 methylation. The interplay of Polycomb group and Trithorax group proteins maintains a well-defined set of genes in an active or repressed state. Therefore, R2R1 has a profound effect on chromatin domains and gene expression by its binding to Polycomb group (PcG) PRC1 and TrxG proteins. A peptide derived from the R2R1 protein, a protein (partly) similar to R2R1, or a small molecule interacting with the R2R1-RNF2 and/or R2R1-DPY-30/ASH2L binding site can restore ciliogenesis in patients suffering from COPD.

It is necessary to demonstrate that the R2R1 protein controls the set of genes that are responsible for ciliogenesis in human PBECs. Stated otherwise, we have to show evidence that R2R1 binds specific DNA sequences (promoters or enhancers) of genes that regulate or support ciliogenesis.

R2R1-binding sites in the genome of human PBECs were identified in CHIP-Seq experiments (Chromatin Immunoprecipitation followed by Next Generation Sequencing of enriched DNA fragments). N-terminal FLAG-HA tandem epitope-R2R1 protein and N-21 wo 2017/085225 PCT/EP2016/078075 terminal FLAG-HA tandem epitope-only protein were constitutively expressed (lentiviral transduction) in human PBECs that were grown in All conditions. Chromatin-constituting genomic DNA and proteins were crosslinked by DSG (disuccinimidyl glutarate) and formaldehyde. The chromatin was sonicated to the appropriate size (~200 bp) and immunoprecipitated with EZview™ Red Anti-HA Affinity Gel (Sigma Aldrich) in order to bind FLAG-HA-tandem epitope-only and FLAG-HA tandem epitope-R2R1 associated genomic DNA fragments. Subsequently, a library for Next Generation Sequencing (NGS) was prepared from these DNA fragments (after protein de-crosslinking and digestion) and sequenced at a depth of at least 40×10⁶ reads. The set of (~3000) R2R1-binding sites was obtained by comparing (EaSeq, hypertext transfer protocol:easeq.net) the enrichment of binding sites in FLAGHA tandem epitope-R2R1 libraries over binding sites in FLAG-HA tandem epitope-only 'control' libraries. Reproducibility was assessed and demonstrated by performing technical and biological duplicates (donors Br331 and Br363).

First, analysis of the set of R2R1-binding sites reveals that R2R1 binds the promoter sites of TP73 and FOXJ, the master transcription factors that stimulate the production of motile cilia. Furthermore, R2R1 also binds the promoter sites of genes coding for components of the centrosomal/basal body machinery of the cilium (CROCC, CCDC41, CEP131, CEP164, CEP170, CEP170B, CEP192 etc.). Finally, other master regulators (transcription factors, miR-NAs, chromatin modifiers and the like) of ciliogenesis and epithelial differentiation were also identified (FUZ, FGFR1, MIR34AHG, ARID1B, JARID2, YY1, KDM2A, KDM2B, KDM4B, KDM6B, KMT2A, KMT5B, SETD1A . . . ). Thus, the invention may relate to compounds (for example the R2R1 based compounds described herein) capable of modulating, binding to or associating with, genes coding for components of the centrosomal/basal body machinery of the cilium and/or regulators of ciliogenesis and epithelial differentiation.

Exemplary DNA sequences of R2R1-binding sites are shown below.

TP73
>hg19_dna range = chr1:3607302-3607501 5'pad = 0 3'pad = 0 strand = + repeatMasking = none
GTTCCCCAGCATCCTCGGCTCCTGCCTCACTAGCTGCGGAGCCTCTCCCG

CTCGGTCCACGCTGCCGGGCGGCCACGACCGTGACCCTTCCCCTCGGGCC

GCCCAGATCCATGCCTCGTCCCACGGGACACCAGTTCCCTGGCGTGTGCA

GACCCCCCGGCGCCTACCATGCTGTACGTCGGTGACCCCGCACGGCACCT

FOXJ1
>hg19_dna range = chr17:74118677-74118876 5'pad = 0 3'pad = 0 strand = + repeatMasking = none
GCGGAGGCAGAGCGGCCCTGGGGCCCCGGCGTCAGCTGAGGTTGCACTGT

GTTTGGAGAGGAGCCTCGGAGGGGTGGGCTGCCTGGCAGCAGTGGCCTGG

GGGCCGCAAATGAGGAGGGTGCAGTGCCTTGGGCAGTAAATTAGAAGACA

CAGGCTGCTGGCTGGGGCGGGAGGGCACAGGGAAGCCCTGCCCGGGAGC

FUZ
>hg19_dna range = chr19:50308793-50308992 5'pad = 0 3'pad = 0 strand = + repeatMasking = none
CGGGACTTCCTGACGCCCCCGCTGCTGTCCGTGCGCTTCCGGTGAGTCAG

GTACGGCGCGGCCGGTGGGCGGAGCCTCCGGGGTGAGGGGCGGGGCCTAA

TGGAGCCTCCCTTTCACCTCATCAGGTACGGTGGCGCCCCCAGGCCCTC

ACCCTGAAGCTCCCAGTGACCATCAACAAGTTCTTCCAGCCCACCGAGAT

FUZ
>hg19_dna range = chr19:50304563-50304762 5'pad = 0 3'pad = 0 strand = + repeatMasking = none
ATCCTAGGGAGGGGCACCTCTCGAGGGGGTTTCTGGGAGAGGGCAGTGGA

ACCTGGCCCCGCTGACACCCACTCCTGCACACAGCCCCCCAGTGCAGTTC

TCCCTGCTCCACTCCAAGTTCCATCTGTGCAGCGTGGCCACGCGGGCGCT

GCTGCTGTCCACCTACATCAAGTTCATCAACCTCTTCCCCGAGACCAAGG

CROCC
>hg19_dna range = chr1:17266175-17266468 5'pad = 0 3'pad = 0 strand = + repeatMasking = none
CCCAGGGAGGTGAGGGCTCAGAGGGTGGCGAGGGCACATAGGAGGGGAGC

GGAAGCCTGGCTCTCAGGCCTAGGCCCCTATCCTGCCCCAGGCCAGGTCC

AGGCCCTGGACCCCGCCTAGCGTAGGCTAGTGTGTATCCCTGGAACCAGA

AGAGAGTAGGTGGCTCTGGAGGCCTCTCAGGCCCCCCCAGACTCTGTGAC

CCCCCACACCCCAGGACATGCGTGGGCGCTATGAGGCAAGCCAGGACCTA

CTGGGCACCCTGCGGAAGCAGCTTAGCGACAGCGAGAGCGAGCG

CROCC
>hg19_dna range = chr1:17239197-17239454 5'pad = 0 3'pad = 0 strand = + repeatMasking = none
TCCAGGGACTGGCTGTGCATACTGGCAGATGTCAGTCAGCCCTCCTGCAG

TTGGGCCAGGGACACCTCAGGGAAACTGTGACCTTCCTTCCAATCTTGGT

AACATCACCCTTCCACCCCAAATCCCAGGGAATGGCCCGAATCTCTCCTG

ACAAACAGCTCTCAGCCCTGGTCCAGGCCACAGTCTTGCTTGCACCGGGC

CGGGTTTCAGAGCCCGAAGGGCACACTGGCAGCCTTTAGTGCAGTGTTTC

AGATGTCA

CROCC
>hg19_dna range = chr1:17249731-17249930 5'pad = 0 3'pad = 0 strand = + repeatMasking = none
GTGGCGCACACGGTGTAGTTATGTGGCTTGAGGATCTGGGAAAGGCACAC

TCAGTTGCAGCTGGTGTGCTGGCGTGTGGCGTTTTGGTGCTCTAACCATT

GTCTGTGTTCAACTCCCAAGCTACAGACGGGCCCCCTCCTTGGGAGCGCC

AGGGATGTTGGCGCCCTGGAGCCCCAGACAGGGAGAGACTCAGAGGGCCC

CROCCP2 (CROCC region)
>hg19_dna range = chr1:16949769-16950030 5'pad = 0 3'pad = 0 strand = + repeatMasking = none
CGACTACAGGGAATGGAAATGGTATAGCCATCATCTAAAAACCATCTCCC

GGGTTGGAAACCCACCAGCATTTCCCTTCCTGGTTCTGTCTGGCTCAGGT

GTACATGGACAGGAAAATTAATTTCCATGACCCAAGTAGGTGCTTAGTTA

ATGTTAGATGAGCAGAAAGAAGCCCTGAGTTCAGAGATTCGATGGGGAAC

GGTGCAGGGAAGTGGGGCTCGGATTCTGGGGCCAAGAGAGTCATCTGAAA

ACCACAGAGAAC

CROCCP3 (CROCC region)
>hg19_dna range = chr1:16825373-16825572 5'pad = 0 3'pad = 0 strand = + repeatMasking = none
AGGGGACCCCGACCGGCGGAGGGACGGCTGCGCCCTGCAGGCCGCTGCGC

CCAGGCAGGCCTCTGCGCCCGGGCAGGCCTCGGCCTCCTGTCGCGCCCCC

GGCCCGCGACAATCCGGGCAGGATGGGCGGCAGGACGCGGAGGGGCATCT

GCGGAGCCCGTCGGGAACGCCCTCTTGGCTTCCGGTGCCGGGCAGCGGCG

-continued

CEP131
>hg19_dna range = chr17:79196529-79196728 5'pad =
0 3'pad = 0 strand = + repeatMasking = none
TGCGCCCTGCAACCCCCTCCCTTGCCCGGGCCCCCCTCACCTGCGCGGGC

CGGGGGCGCAGCCGCGAAGCCTGCCTGGCGCGCGGGGCCTGCAGATTCGG

CCGGCGGGGAGGGGATGCGGAACCAGTCGCGCCCAAACCTCGGGTCGGCG

ACCTGGCGCCCCGCCACCCCCAACACTGCCCCGAGGCCCGGTGACAATGA

CEP164
>hg19_dna range = chr11:117198627-117198826 5'
pad = 0 3'pad = 0 strand = + repeatMasking = none
GTTGGGTGGCGTTGGGGGAGCTGCGCCTCGCCCAGAGCCTCGCCCGGAGC

CTCGCCCGGAGCCTTCCGGGGTGGGGGATAGTTGAGGACCTCATCGAGGG

AGGGGTTGGGCGGCGGGGAAGGGAGCGAGCGTGGCGGGGGACCCGAGGCA

CGCTCTCGAGCCAACGAGCGTGATGCGCTCGAGTGTGGGCGGGGACTGAG

CEP170
>hg19_dna range = chr1:243418128-243418414 5'
pad = 0 3'pad = 0 strand = + repeatMasking = none
AAGCCCCGGGTCCCAGGCGGGCAGAGGGTGGGGGTGGCGGCGCCGCGCGG

AGCACCCGGGAAGCGCCCCCTTCGCGGTCCAGCCCCGCACCCCCGCCCCG

CGGCGGGCGGCGCCCGAGTCCTCGCCGCAAACCCGAGGAGCAGGATGTGG

AAAGCAGCCGCGGCGGTGGCTGCGGCTGCGGCGCCTACACCGAGCAGCCG

ATCGCATCACTTACCCCTTACCGTGGAGAGAGGGACCGGACGGGGGAGGC

GGGGCGCGTCGCGTCCCGTGAGTCTCTCGCACGCCGT

CEP170B
>hg19_dna range = chr14:105331641-105331930 5'
pad = 0 3'pad = 0 strand = + repeatMasking = none
CGCTCTGCCGTGGGCTCGGCCCGGGCTGCCACGAGCGTGCGGGCCTCGCC

GGGCATGTCCTAGGCGGCGGCCCCGCCCAGCGCTCGGCCGGGCGGGCGGG

CGGGCGCGAGGGCAGGGACCGAGCCGGGCCGAGCTGGGGAACAAGCCGGG

GACCAAGCCGGGGACCAAGCCGGGGACTAAGGCGAGCCGGAGACCGAGCC

CGAACAGCAGGTAGGACGCGCCGGCCCAGCGCTGGCCGCGGCCCGGGCCT

CCCATCGCCCGCACCTGCACGGCTGTGGGGTCTCACGGGG

CEP170B
>hg19_dna range = chr14:105333102-105333301 5'
pad = 0 3'pad = 0 strand = + repeatMasking = none
AGACCTTGGGCGTGGGCACTGGGCAAAGTAGGGACAAGGAGCCACTCACT

CCTCTGCCTGGCACCCTCATGTGGTGTGGCCCTGCCCTCAGGATGCACTC

AGCCCGGCAGCCTCCCCTTCTCCTCTGCTCCACTGGGCCTCAGCTGCTGT

CATCCCTGTCCTGGGTTATTGTCCTCACTTCTTGACTGGCCTCCTGAGTC

CEP170B
>hg19_dna range = chr14:105332644-105332843 5'
pad = 0 3'pad = 0 strand = + repeatMasking = none
GGGCCGCGGCAGGTGATGGCAGAGGGTGAGGCCTAGGAGGGCTGGCTGGG

GGCCGGAGGTGCAATGGTGGGGTAGGCCCTGCCCGATAGAGCACCCTGTG

GTCTCCCCCAGCAGCCCTAGGGAGGGTGGGGCTGTAGAGGCCTCCTGGAG

GCTTTGCTGTCTGGGGCTGCAGGGTCATCGAAGTGCCAGCCCCTTGGCCT

CEP170B
>hg19_dna range = chr14:105341395-105341594 5'
pad = 0 3'pad = 0 strand = + repeatMasking = none
TGGTGTTTCATGACGGTGCCCTGTGGTGGGGCAGTGATGGCCAGCTGCCA

GGGTGGCCTGCACGTGGCAGGCTAAGAGTGACCAGCCTGAGGGGCCCAGG

CTCTCACCTGGGAGACTGAGAAGCCGTGCTGGCACTCAGGAGGGACTTCC

AGCTCCTAGTCGTGTGGGTTGCAGGCCGTCCTGTCCCAGGGCTGGGGGAC

CEP192
>hg19_dna range = chr18:12991416-12991615 5'
pad = 0 3'pad = 0 strand = + repeatMasking = none
GAAGTCGGGGACGCGGGCTCGGTGAGGGGGGACGCTGGTGCCTCGGCCTG

CGCCTAGGCGGGAGGCAGACGCATGCACCTTTGGCCTACGTTTCGGCTGC

CGGACCGACGGGACAGTGACGGTTGGGCCGGGTGGGGGCGCAGGCTGTGG

GGCGGCCTCAGGGCGCGAGCAAGGGGACTGCCGCGCTTCCCGCGCCTCTG

CCDC41
>hg19_dna range = chr12:94853729-94853928 5'
pad = 0 3'pad = 0 strand = + repeatMasking = none
TTGGCCCAGCCGGCACGCGAAGCAGGAAGTCCCACCCCCCACGCCGACGTC

ACCCACGCCACCGACGCCGGTTGCTGCCGGAGCCGTTAGAGGGAGGAGAC

AAACGAACCGAGGCGGGAGCGGCCACGGGTGACAGCGGCAGCGGCGGGGC

CGGGCTGCGCTCCCGAAGGCGTTCCTGGAGGGCCCTGGGATGGACTCAGA

MIR34AHG
>hg19_dna range = chr1:9242327-9242526 5'pad = 0
3'pad = 0 strand = + repeatMasking = none
ACCGACGGGACAGCGGCATCTCCTCCACCTGAAAAGGAAAGAGGACCAGG

TGGGGGCCAGGCAGGGCGCATGAAGGCGGCGCCAGCACCGCGCGATCCGA

ATCACGTCGGTGCGGGGAGGGGTCGGAGCCTGGCCTCGGCCTAGGGCGC

AGATGCGGTGCGCACCGCAGGGGGGCGGCGTGGGGTGCGGGGCCAGTCC

DNA sequences of the exemplary R2R1-binding sites are characterized by a high GC (base) content. Indeed, analysis of the base content of the whole set of R2R1-binding sites (~3000 sites) shows that the GC content exceeds the AT content: G&C bases represent ≥66% of the base content of the genomic R2R1-binding sites. Motif discovery in the R2R1-binding sites using Regulatory Sequence Analysis Tools (RSAT, hypertext transfer protocol:rsat.sb-roscoff.fr) reveals highly specific GC-motifs. These motifs reoccur independently of the motif discovery method in RSAT (calculation of oligonucleotide occurrences in a set of sequences leading to detection of overrepresented oligonucleotides, calculation of the positional distribution of oligonucleotides in a set of sequences leading to detection of those which significantly differ from a homogeneous distribution and detection of overrepresented spaced dyads in a set of DNA sequences with a dyad being a pair of oligonucleotides of the same size—definitions provided by RSAT server: hypertext transfer protocol:rsat.sb-roscoff.fr). Recurrent GCC (CGG) patterns are obvious in the discovered motifs. In general, a high GC content and repetitive stretches of GC nucleotides are characteristic of CpG islands (CGIs). These CGIs are currently thought to comprise the genomic binding sites of PeG (Polycomb Response Elements or PREs) and TrxG complexes (Trithorax Response Elements or TREs), also referred to as PREs in general. It follows that we have established another link to Polycomb function: R2R1 represents a PRE-recognition element. This has special significance for PeG complexes: in contrast to TrxG complexes, no universal PRE-recognition element has been identified in PeG complexes.

EXAMPLE 2

2.1: Restoration of Ciliogenesis in COPD Donor-Derived PBECs in ALI Conditions First we must determine that ciliogenesis due to the absence of R2R[1] isn't limited to PBECs derived from non-COPD donors. Therefore we have to establish that:
(a) The expression of R2R1 can be reliably up- or downregulated in PBECs from a COPD and non-COPD donor.
(b) The expression of the R2R1 protein is related to the expression of the R2R1 (transcript).
(c) Knockdown of R2R1 expression triggers the ciliary gene expression program in PBECs from a COPD and non-COPD donor. Conversely, upregulation of R2R1 expression leads to suppression of the ciliary transcriptome.
(d) The transcriptomic changes need to be mirrored in the cellular phenotype.

The ciliogenesis transcriptome should lead to an increase in the number of ciliated cells in ALI cultures of COPD-derived PBECs.

The following experiment demonstrates points 2.1 (a), 2.1 (b), 2.1 (c) and 2.1 (d) above.

PBECs derived from a non-COPD donor (Br331) and a COPD donor (Br370) were grown in ALI conditions. Transcriptomic and cellular phenotypic analyses are performed at 1, 2 and 3 weeks of Air Exposure (AE). Each condition was performed in triplicate.

The different conditions are:
(i) MC (Medium Control) is the cell population growing without any intervention.
(ii) Downregulation of R2R1 expression in PBECs is achieved by constitutive expression (lentiviral transduction) of FAM25 147=TRCN0000284147 (referred to as shRNA_R2R1). PBECs constitutively expressing scrambled shRNA (referred to as shRNA_NC) are the negative control cells in this condition.
(iii) Upregulation of R2R1 expression is achieved by constitutive expression of an N-terminal FLAG-HA tandem epitope-R2R1 (referred to as FHR2R1) construct (lentiviral transduction). PBECs expressing constitutively the FLAG-HA tandem epitope-only construct (referred to as FH) are the negative control cells in this condition.
iv) Donor: non-COPD (Br331) and COPD (Br370)
(v) Time: PBECs are harvested at 1, 2 and 3 weeks of AE (Air Exposure)

2.2: Br370 (COPD) PBECs Exhibit a Persisting Downregulation of the Ciliary Gene Expression Program Over Time.

The hypothesis is that (1) ciliogenesis should become progressively apparent over time in the gene expression profile of PBECs in ALI culture. We also hypothesise that (2) the ciliogenesis transcriptome should lag in Br370 (COPD) PBECs in comparison to Br331 (non-COPD) PBECs.

Analysis of the gene expression program in MC PBECs (PBECs that are not lentivirally transduced) will prove or disprove our hypothesis.

Spectral Map (SPM) analysis confirms our hypothesis. Spectral Map Analysis (see FIG. 8) provides an unbiased identification of the predominant clusters of genes and subjects that are present in the data set. This unsupervised analysis of gene expression data reveals that gene expression changes during time (week of Air Exposure) account for the largest variation (56%) in the data set. This variation is graphically well represented in the first principal component (X-axis or $PC_1$) of a spectral map. The second largest variation in the data set (17%) can be explained by disease status (COPD versus non-COPD). This variation is represented in the second principal component (Y-axis or $PC_2$). Genes displaying the strongest expression changes lie at the extremes of the X and Y axis.

The subset of genes responsible for the biggest differential expression changes consists completely of ciliary genes (see FIG. 8).

DYNLRB2 and ROPNL1 are highlighted as exemplary ciliary genes. As expected, this subset lies indeed at the extreme of the X-axis ($PC_1$, the variation accounted for by time). This confirms the first (1) part of our hypothesis.

Subsequently, superposition of the different MC PBECs samples on the spectral map shows their distribution along the first two principal components. We observe now that the COPD (Br370) and non-COPD (Br331) groups are clearly separated according to their ciliary gene expression program along $PC_1$ and $PC_2$. Non-COPD Br331 PBECs cluster the closest to the subset of ciliary genes. COPD Br370 PBECs cluster at the opposite end of the subset of ciliary genes. This proves the second part (2) of our hypothesis. As a matter of example, we include the gene expression profile of DYNLRB2 (see FIG. 9). This independent supervised univariate (gene-by-gene) analysis confirms the effect of COPD versus non-COPD origin (Br370 versus Br331). Non-COPD Br331 PBECs harvested at the first time point (AE week=1) show the lowest level of DYNLRB2 expression. Conversely, non-COPD Br331 PBECs harvested at the third time point (AE week=3) display a very high level of DYNLRB2 expression. COPD Br370 PBECs poorly express this exemplary gene.

2:3: The Expression of R2R1 can be Reliably Up- or Downregulated in PBECs from a COPD and Non-COPD Donor.

RTqPCR of R2R[1] gene expression (Assay ABI Hs04194072_mH and Assay ABI Hs04194073_mH) demonstrates complete downregulation (knockout) upon constitutive expression of shRNA_R2R[1] in non-COPD Br331 PBECs and COPD Br370 PBECs (see FIG. 10). Conversely, RTqPCR of R2R[1] gene expression (Assay ABI Hs04194072_mH and Assay ABI Hs04194073_mH) shows >$10^4$ upregulation upon constitutive expression of FHR2R1 in non-COPD Br331 PBECs and COPD Br370 PBECs (see FIG. 11). The data are represented in scatter dot plots (line at mean). The RTqPCR data prove that R2R[1] expression can be up- or downregulated in a very profound, significant and reliable manner.

2:4: The Expression of the R2R1 Protein is Related to the Expression of the R2R1 (Transcript).

Total R2R[1] protein content in the nucleus is assessed by the following procedure. PBECs are immunohistochemically stained with 1/500 Anti-FAM25A antibody (Abcam ab177969). Secondary antibody staining is performed with 1/1500 Goat anti-Rabbit IgG (H+L) Secondary Antibody, Alexa Fluor® 594 conjugate (Thermo-Fisher Scientific A-11037). Using Image J (hypertext transfer protocol: rsbweb.nih.gov/ij/index.html), the Corrected Total Cell Fluorescence is determined (CTCF) in 10 fields at 20× magnification. CTCF is used as an assessment of total R2R1 protein content in the nucleus. FIG. 12 illustrates the characteristic fluorescence pattern of the different conditions (MC, FH, FHR2R1, shRNA_NC and shRNA_R2R1) at a given time point of Air Exposure. The scatter dot plot (line at mean with SD) shows the fluorescence pattern of COPD Br370 PBECs at week 1 of Air Exposure (AE). FIG. 13 demonstrates the sequence over time of fluorescence pattern in non-COPD Br331 PBECs. FIG. 14 summarizes the 3 different time points of FIG. 13 in one graphical representation.

The CTCF data prove that up- or downregulation of R2R¹ gene expression is followed by up- or downregulation of R2R¹ protein expression in the nucleus. Furthermore, the nuclear localization of the R2R¹ protein is consistent with the R2R¹-PcG and R2R¹-TrxG interaction.

2.5: Knockdown of R2R¹ Expression Triggers the Ciliary Gene Expression Program in PBECs from a COPD and Non-COPD Donor. Conversely, Upregulation of R2R¹ Expression Leads to Suppression of the Ciliary Transcriptome.

To demonstrate point 2.5, we performed an unsupervised analysis (SPM) of gene expression levels of all the samples of the experiment. The set of all samples consists of the conditions MC, FH, FHR2R1, shRNA_NC and shRNA_R2R¹ at 1, 2 and 3 weeks of Air Exposure in non-COPD Br331 and COPD Br370 PBECs. Results show that the subset of genes responsible for the biggest differential expression changes consists completely of ciliary genes (see FIG. 15). Furthermore, the same holds true for the subsets of R2R¹ 'downregulation' (samples MC, shRNA_NC, shRNA_R2R¹) and R2R¹ 'upregulation' conditions (samples MC, FH, FHR2R¹) (FIG. 16 and FIG. 17 respectively). The exemplary ROPN1L gene is highlighted in each SPM graph.

Upon closer inspection, we observe that samples with downregulated R2R¹ expression cluster more closely to the ciliary gene cluster in FIGS. 15 and 16. For example, the non-COPD Br331 shRNA_R2R¹ (week 3 of AE) samples are located very closely to the ciliary gene cluster. The reverse holds true for the upregulation of R2R1 gene expression: samples with upregulated R2R¹ expression ('FHR2R¹ samples') are located at a greater distance from the ciliary gene cluster on the XY-axis. For example, the COPD Br370 FHR2R¹ (week 1 of AE) samples are located at the opposite end of the ciliary gene cluster. The effect of R2R¹ knockdown on ciliogenesis in COPD Br370 PBECs isn't readily apparent on the SPM graphs of FIGS. 15, 16 and 17. However, further analysis reveals that knockdown of R2R¹ gene expression in Br370 PBECs leads to a position nearer to the ciliary gene cluster on the XY-axis (FIG. 18). This unsupervised analysis points to 'resurgence of ciliogenesis' in COPD PBECs.

Finally, gene-by-gene analysis (LIMMA) confirms the effect of R2R1 knockdown on ciliogenesis in COPD Br370 PBECs. The $\log_2$ intensity plots of exemplary ROPN1L gene expression (FIGS. 19, 20 and 21) illustrate 'resurgence of ciliogenesis' in COPD Br370 PBECs.

2:6: Transcriptomic Changes should be Mirrored in the Cellular Phenotype. The Ciliogenesis Transcriptome should Lead to an Increase in the Number of Ciliated Cells in ALI Cultures of COPD-Derived PBECs.

In order to reverse the COPD phenotype, more ciliated cells need to be present. Therefore, we have to prove that upregulation of ciliary gene expression is accompanied by an increase in the number of ciliated cells.

PBECs (grown concomitantly in the experiments described above) are immunohistochemically stained:
DAPI: staining of nuclei
Staining of mucus producing cells: anti-MUCSAC Antibody (45M1)+Chicken anti-Mouse IgG (H+L) Secondary Antibody, Alexa Fluor® 488 conjugate
Staining of ciliated cells: Monoclonal Anti-Acetylated Tubulin antibody (clone 6-11B-1)+Goat anti-Mouse IgG (H+L) Secondary Antibody, Alexa Fluor® 594 conjugate Stained cells are counted in 10 fields (20× magnification). The scatter dot plots (line at mean with SD) illustrate that downregulation of R2R1 expression (shRNA_R2R1) leads to an increase in the number of ciliated non-COPD (Br331) and COPD (Br370) PBECs (see FIG. 22). The reverse also holds true: upregulation of R2R1 expression leads to disappearance of the ciliated cell population (see FIG. 23). The negative control condition for shRNA_R2R1 mediated knockdown is the expression of negative control shRNA_NC. The negative control condition for FHR2R1 expression is the expression of the FH-tag only construct.

Changes in R2R1 expression don't lead to changes in the number of mucus producing cells (see FIGS. 24, 25). This is of paramount importance as an increase in the number of mucus producing cells would worsen the disease symptoms. In fact, non-COPD Br331 and COPD Br370 PBECs produce the same number of mucus producing cells at week 3 of AE (whatever the condition). This underscores again the fact that defective ciliogenesis is a principal driver of the COPD phenotype.

For illustrative purposes, FIGS. 26, 27, 28 and 29 are included. The top row in each figure shows the triple staining (blue: nuclei, green: mucus producing cells, red: ciliated cells) of PBECs. The bottom row only displays the ciliated cells (red) of the same field of the top row.

The invention claimed is:

1. A method of treating diseases and/or conditions of the pulmonary system and/or airways caused by a loss of ciliogenesis, said method comprising administering to a subject in need thereof a therapeutically effective amount of a compound comprising an antisense oligonucleotide or an RNAi type inhibitor that reduces, inhibits and/or ablates the expression, function and/or activity of the R2R1 gene, thereby treating the diseases and/or conditions of the pulmonary system and/or airways caused by a loss of ciliogenesis.

2. The method of claim 1, wherein the compound is an antisense oligonucleotide.

3. The method of claim 1, wherein the compound comprises a sequence of SEQ ID NO: 1, 2, 3 or 4 or a fragment thereof.

4. The method of claim 1, wherein the compound is an antisense oligonucleotide which reduces the expression of the R2R1 gene.

5. The method of claim 1, wherein the disease and/or condition is chronic obstructive pulmonary disorder (COPD).

* * * * *

SEQUENCE LISTING

```
<160> NUMBER OF SEQ ID NOS: 25

<210> SEQ ID NO 1
<211> LENGTH: 425
<212> TYPE: DNA
<213> ORGANISM: Mus musculus

<400> SEQUENCE: 1
acactgacac ggaccgaagg agtggaaaaa gctttacctg tcactgtctg ctgccatacg      60
atgctgggag gcctggggaa gctggcggcc gagggcctgg cccaccgcac agagaaagcc     120
actgggggag cagttcacgc agtggaagag gtggtgagcg aggtggtggg ccacgccaag     180
gaggttggag agaagaccat taatgacgcc ctaaagaaag cccaagaatc aggagacagg     240
gtggtgaagg aggtcactga gaaggtcacc cacaccatca ctgatgctgt tacccatgcg     300
```

```
gcagaaggcc tgggaagact gggacagtga gcctgcctac cagcatggct ggcccttcct    360
gaaggtcaat aaagagtgtg aaacgtgaaa aaaaaaaaa aataacaaa aaaaaaaaa       420 aaaaa                                                                425
```

<210> SEQ ID NO 2
<211> LENGTH: 267
<212> TYPE: DNA
<213> ORGANISM: Mus musculus

<400> SEQUENCE: 2

```
atgctgggag cctggggaa gctggcggcc gagggcctgg cccaccgcac agagaaagcc     60 actggggag cagttcacgc agtggaagag gtggtgagcg aggtggtggg ccacgccaag    120
gaggttggag agaagaccat taatgacgcc ctaaagaaag cccaagaatc aggagacagg   180
gtggtgaagg aggtcactga aaggtcacc cacaccatca ctgatgctgt tacccatgcg    240
gcagaaggcc tgggaagact gggacag                                        267
```

<210> SEQ ID NO 3
<211> LENGTH: 342
<212> TYPE: DNA
<213> ORGANISM: Homo sapiens

<400> SEQUENCE: 3

```
actgtctgct gccacacgat gctgggaggc ctggggaagc tggctgccga aggcctggcc    60
caccgcaccg agaaggccac cgagggagcc attcatgccg tggaagaagt ggtgaaggag   120
gtggtgggac acgccaagga gactggagag aaagccattg ctgaagccat aaagaaagcc   180
caagagtcag gggacaaaaa gatgaaggaa atcactgaga cagtgaccaa cacagtcaca   240
aatgccatca cccatgcagc agagagtctg gacaaacttg gacagtgagt gcacctgcta   300
ccacggccct tccccagtct caataaaaag ccatgacatg tg                       342
```

<210> SEQ ID NO 4
<211> LENGTH: 267
<212> TYPE: DNA
<213> ORGANISM: Homo sapiens

<400> SEQUENCE: 4

```
atgctgggag cctggggaa gctggctgcc gaaggcctgg cccaccgcac cgagaaggcc     60
accgagggag ccattcatgc cgtggaagaa gtggtgaagg aggtggtggg acacgccaag   120
gagactggag agaaagccat tgctgaagcc ataaagaaag cccaagagtc aggggacaaa   180
aagatgaagg aaatcactga gacagtgacc aacacagtca caaatgccat cacccatgca   240
gcagagagtc tggacaaact tggacag                                        267
```

<210> SEQ ID NO 5
<211> LENGTH: 89
<212> TYPE: PRT
<213> ORGANISM: Mus musculus

<400> SEQUENCE: 5

```
Met Leu Gly Gly Leu Gly Lys Leu Ala Ala Glu Gly Leu Ala His Arg
1               5                   10                  15

Thr Glu Lys Ala Thr Gly Gly Ala Val His Ala Val Glu Glu Val Val
                20                  25                  30

Ser Glu Val Val Gly His Ala Lys Glu Val Gly Glu Lys Thr Ile Asn
        35                  40                  45
```

Asp Ala Leu Lys Lys Ala Gln Glu Ser Gly Asp Arg Val Val Lys Glu
            50                  55                  60

Val Thr Glu Lys Val Thr His Thr Ile Thr Asp Ala Val Thr His Ala
65                  70                  75                  80

Ala Glu Gly Leu Gly Arg Leu Gly Gln
                85

<210> SEQ ID NO 6
<211> LENGTH: 89
<212> TYPE: PRT
<213> ORGANISM: Homo sapiens

<400> SEQUENCE: 6

Met Leu Gly Gly Leu Gly Lys Leu Ala Ala Glu Gly Leu Ala His Arg
1               5                   10                  15

Thr Glu Lys Ala Thr Glu Gly Ala Ile His Ala Val Glu Glu Val Val
            20                  25                  30

Lys Glu Val Val Gly His Ala Lys Glu Thr Gly Glu Lys Ala Ile Ala
        35                  40                  45

Glu Ala Ile Lys Lys Ala Gln Glu Ser Gly Asp Lys Lys Met Lys Glu
    50                  55                  60

Ile Thr Glu Thr Val Thr Asn Thr Val Thr Asn Ala Ile Thr His Ala
65                  70                  75                  80

Ala Glu Ser Leu Asp Lys Leu Gly Gln
                85

<210> SEQ ID NO 7
<211> LENGTH: 200
<212> TYPE: DNA
<213> ORGANISM: Homo sapiens

<400> SEQUENCE: 7
gttccccagc atcctcggct cctgcctcac tagctgcgga gcctctcccg ctcggtccac      60
gctgccgggc ggccacgacc gtgacccttc ccctcgggcc gcccagatcc atgcctcgtc     120
ccacgggaca ccagttccct ggcgtgtgca gaccccccgg cgcctaccat gctgtacgtc     180
ggtgaccccg cacggcacct                                                 200

<210> SEQ ID NO 8
<211> LENGTH: 200
<212> TYPE: DNA
<213> ORGANISM: Homo sapiens

<400> SEQUENCE: 8
gcggaggcag agcggccctg ggccccggc gtcagctgag gttgcactgt gtttggagag       60
gagcctcgga ggggtgggct gcctggcagc agtggcctgg gggccgcaaa tgaggagggt     120
gcagtgcctt gggcagtaaa ttagaagaca caggctgctg gctgggggcg ggagggcaca     180
gggaagccct gcccgggagc                                                 200

<210> SEQ ID NO 9
<211> LENGTH: 200
<212> TYPE: DNA
<213> ORGANISM: Homo sapiens

<400> SEQUENCE: 9
cgggacttcc tgacgccccc gctgctgtcc gtgcgcttcc ggtgagtcag gtacggcgcg      60
gccggtgggc ggagcctccg gggtgagggg cggggcctaa tggagcctcc ctttcacctc     120
atcaggtacg gtggcgcccc ccaggccctc accctgaagc tcccagtgac catcaacaag    180
ttcttccagc ccaccgagat                                                200

<210> SEQ ID NO 10
<211> LENGTH: 200
<212> TYPE: DNA
<213> ORGANISM: Homo sapiens

<400> SEQUENCE: 10
atcctaggga ggggcacctc tcgagggggt ttctgggaga gggcagtgga acctggcccc    60
gctgacaccc actcctgcac acagcccccc agtgcagttc ccctgctcc actccaagtt    120 ccatctgtgc agcgtggcca cgcgggcgct gctgctgtcc acctacatca agttcatcaa    180
cctcttcccc gagaccaagg                                                200

<210> SEQ ID NO 11
<211> LENGTH: 294
<212> TYPE: DNA
<213> ORGANISM: Homo sapiens

<400> SEQUENCE: 11
cccagggagg tgagggctca gagggtggcg agggcacata ggaggggagc ggaagcctgg    60
ctctcaggcc taggcccta tcctgcccca ggccaggtcc aggccctgga ccccgcctag    120
cgtaggctag tgtgtatccc tggaaccaga agagagtagg tggctctgga ggcctctcag    180 gccccccag actctgtgac cccccacacc ccaggacatg cgtgggcgct atgaggcaag    240
ccaggaccta ctgggcaccc tgcggaagca gcttagcgac agcgagagcg agcg          294

<210> SEQ ID NO 12
<211> LENGTH: 258
<212> TYPE: DNA
<213> ORGANISM: Homo sapiens

<400> SEQUENCE: 12
tccagggact ggctgtgcat actggcagat gtcagtcagc cctcctgcag ttgggccagg    60
gacacctcag ggaaactgtg accttccttc caatcttggt aacatcaccc ttccacccca    120
aatcccaggg aatggcccga atctctcctg acaaacagct ctcagccctg gtccaggcca    180
cagtcttgct tgcaccgggc cgggtttcag agcccgaagg gcacactggc agcctttagt    240
gcagtgtttc agatgtca                                                  258

<210> SEQ ID NO 13
<211> LENGTH: 200
<212> TYPE: DNA
<213> ORGANISM: Homo sapiens

<400> SEQUENCE: 13
gtggcgcaca cggtgtagtt atgtggcttg aggatctggg aaaggcacac tcagttgcag    60
ctggtgtgct ggcgtgtggc gttttggtgc tctaaccatt gtctgtgttc aactcccaag    120
ctacagacgg gccccctcct tgggagcgcc agggatgttg gcgccctgga gccccagaca    180
gggagagact cagagggccc                                                200

<210> SEQ ID NO 14
<211> LENGTH: 262
<212> TYPE: DNA
<213> ORGANISM: Homo sapiens

<400> SEQUENCE: 14

```
cgactacagg gaatggaaat ggtatagcca tcatctaaaa accatctccc gggttggaaa    60
cccaccagca tttcccttcc tggttctgtc tggctcaggt gtacatggac aggaaaatta   120
atttccatga cccaagtagg tgcttagtta atgttagatg agcagaaaga agccctgagt   180
tcagagattc gatggggaac ggtgcaggga agtggggctc ggattctggg gccaagagag   240
tcatctgaaa accacagaga ac                                            262

<210> SEQ ID NO 15
<211> LENGTH: 200
<212> TYPE: DNA
<213> ORGANISM: Homo sapiens

<400> SEQUENCE: 15
aggggacccc gaccggcgga gggacggctg cgccctgcag gccgctgcgc ccaggcaggc    60
ctctgcgccc gggcaggcct cggcctcctg tcgcgccccc ggcccgcgac aatccgggca   120
ggatgggcgg caggacgcgg agggcatct gcggagcccg tcgggaacgc cctcttggct   180
tccggtgccg ggcagcggcg                                              200

<210> SEQ ID NO 16
<211> LENGTH: 200
<212> TYPE: DNA
<213> ORGANISM: Homo sapiens

<400> SEQUENCE: 16
tgcgccctgc aaccccctcc cttgcccggg ccccccctcac ctgcgcgggc cgggggcgca    60
gccgcgaagc ctgcctggcg cgcggggcct gcagattcgg ccggcgggga ggggatgcgg   120
aaccagtcgc gcccaaacct cgggtcggcg acctggcgcc ccgccacccc caacactgcc   180
ccgaggcccg gtgacaatga                                              200

<210> SEQ ID NO 17
<211> LENGTH: 200
<212> TYPE: DNA
<213> ORGANISM: Homo sapiens

<400> SEQUENCE: 17
gttgggtggc gttgggggag ctgcgcctcg cccagagcct cgcccggagc ctcgcccgga    60
gccttccggg gtgggggata gttgaggacc tcatcgaggg aggggttggg cggcggggaa   120
gggagcgagc gtggcggggg acccgaggca cgctctcgag ccaacgagcg tgatgcgctc   180
gagtgtgggc ggggactgag                                              200

<210> SEQ ID NO 18
<211> LENGTH: 287
<212> TYPE: DNA
<213> ORGANISM: Homo sapiens

<400> SEQUENCE: 18
aagccccggg tcccaggcgg gcagagggtg ggggtggcgg cgccgcgcgg agcacccggg    60
aagcgccccc ttcgcggtcc agccccgcac ccccgccccg cggcgggcgg cgcccgagtc   120
ctcgccgcaa acccgaggag caggatgtgg aaagcagccg cggcggtggc tgcggctgcg   180
gcgcctacac cgagcagccg atcgcatcac ttacccctta ccgtggagag agggaccgga   240
cgggggaggc ggggcgcgtc gcgtcccgtg agtctctcgc acgccgt                287

<210> SEQ ID NO 19
```

```
<211> LENGTH: 290
<212> TYPE: DNA
<213> ORGANISM: Homo sapiens

<400> SEQUENCE: 19
cgctctgccg tgggctcggc ccgggctgcc acgagcgtgc gggcctcgcc gggcatgtcc      60
taggcggcgg ccccgcccag cgctcggccg ggcgggcggg cggcgcgag ggcagggacc     120 gagccgggcc gagctgggga acaagccggg gaccaagccg gggaccaagc cggggactaa    180
ggcgagccgg agaccgagcc cgaacagcag gtaggacgcg ccgcccagc gctggccgcg     240 gcccgggcct cccatcgccc gcacctgcac ggctgtgggg tctcacgggg              290

<210> SEQ ID NO 20
<211> LENGTH: 200
<212> TYPE: DNA
<213> ORGANISM: Homo sapiens

<400> SEQUENCE: 20
agaccttggg cgtgggcact gggcaaagta gggacaagga gccactcact cctctgcctg     60
gcaccctcat gtggtgtggc cctgccctca ggatgcactc agcccggcag cctcccttc    120 tcctctgctc cactgggcct cagctgctgt catccctgtc ctgggttatt gtcctcactt    180
cttgactggc ctcctgagtc                                              200

<210> SEQ ID NO 21
<211> LENGTH: 200
<212> TYPE: DNA
<213> ORGANISM: Homo sapiens

<400> SEQUENCE: 21
gggccgcggc aggtgatggc agagggtgag gcctaggagg gctggctggg ggccggaggt     60
gcaatggtgg ggtaggccct gcccgataga gcaccctgtg gtctccccca gcagccctag    120
ggagggtggg gctgtagagg cctcctggag gctttgctgt ctggggctgc agggtcatcg    180
aagtgccagc cccttggcct                                              200

<210> SEQ ID NO 22
<211> LENGTH: 200
<212> TYPE: DNA
<213> ORGANISM: Homo sapiens

<400> SEQUENCE: 22
tggtgtttca tgacggtgcc ctgtggtggg gcagtgatgg ccagctgcca gggtggcctg     60
cacgtggcag gctaagagtg accagcctga ggggcccagg ctctcacctg ggagactgag    120
aagccgtgct ggcactcagg agggacttcc agctcctagt cgtgtgggtt gcaggccgtc    180
ctgtcccagg gctgggggac                                              200

<210> SEQ ID NO 23
<211> LENGTH: 200
<212> TYPE: DNA
<213> ORGANISM: Homo sapiens

<400> SEQUENCE: 23
gaagtcgggg acgcgggctc ggtgaggggg gacgctggtg cctcggcctg cgcctaggcg     60
ggaggcagac gcatgcacct ttggcctacg tttcggctgc cggaccgacg ggacagtgac    120
ggttgggccg ggtgggggcg caggctgtgg ggcggcctca gggcgcgagc aaggggactg    180
ccgcgcttcc cgcgcctctg                                              200
```

```
<210> SEQ ID NO 24
<211> LENGTH: 200
<212> TYPE: DNA
<213> ORGANISM: Homo sapiens

<400> SEQUENCE: 24
ttggcccagc ggcacgcgaa gcaggaagtc ccacccccca cgccgacgtc acccacgcca      60
ccgacgccgg ttgctgccgg agccgttaga gggaggagac aaacgaaccg aggcgggagc     120
ggccacgggt gacagcggca gcggcggggc cgggctgcgc tcccgaaggc gttcctggag     180
ggccctggga tggactcaga                                                 200

<210> SEQ ID NO 25
<211> LENGTH: 199
<212> TYPE: DNA
<213> ORGANISM: Homo sapiens

<400> SEQUENCE: 25
accgacggga cagcggcatc tcctccacct gaaaaggaaa gaggaccagg tggggggccag    60 gcagggcgca tgaaggcggc gccagcaccg cgcgatccga atcacgtcgg tgcgggggag    120
gggtcggagc ctggcctcgg cctagggcgc agatgcggtg cgcaccgcag gggggcggcg    180
tggggtgcgg ggccagtcc                                                199
```

UNITED STATES PATENT AND TRADEMARK OFFICE
CERTIFICATE OF CORRECTION

| | |
|---|---|
| PATENT NO. | : 11,077,131 B2 |
| APPLICATION NO. | : 15/776668 |
| DATED | : August 3, 2021 |
| INVENTOR(S) | : Ronald Karel Louisa Van Brempt |

It is certified that error appears in the above-identified patent and that said Letters Patent is hereby corrected as shown below:

In the Claims

Column 36, Lines 31-42, should read:

-- 2. The method of claim 1, wherein the compound interferes with, prevents or inhibits binding between native or wild type R2R1 and PRC1 and/or TrxG-MLL and/or a component or subunit of either.

3. The method of claim 1, wherein the compound is an antisense oligonucleotide.

4. The method of claim 1, wherein the compound comprises a sequence of SEQ ID NO: 1, 2, 3 or 4 or a fragment thereof.

5. The method of claim 1, wherein the compound is an antisense oligonucleotide which reduces the expression of R2R1 gene.

6. The method of claim 1, wherein the disease and/or condition is chronic obstructive pulmonary disorder (COPD). --

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*